(12) United States Patent
Cleary et al.

(10) Patent No.: US 8,399,248 B2
(45) Date of Patent: Mar. 19, 2013

(54) METHODS OF USING MIR34 AS A BIOMARKER FOR TP53 FUNCTIONAL STATUS

(75) Inventors: Michele A. Cleary, Jamison, PA (US); Aimee L. Jackson, Carlsbad, CA (US); Peter S. Linsley, Encinitas, CA (US); Julja Burchard, San Francisco, CA (US); Lee P. Lim, San Francisco, CA (US); Jill F. Magnus, Seattle, WA (US); Lin He, Berkeley, CA (US); Xingyue He, Cambridge, MA (US); Scott W. Lowe, Cold Spring Harbor, NY (US); Gregory J. Hannon, Hungtington, NY (US)

(73) Assignee: Merck Sharp & Dohme Corp., Rahway, NJ (US)

(*) Notice: Subject to any disclaimer, the term of this patent is extended or adjusted under 35 U.S.C. 154(b) by 135 days.

(21) Appl. No.: 12/598,563

(22) PCT Filed: May 5, 2008

(86) PCT No.: PCT/US2008/062681
§ 371 (c)(1),
(2), (4) Date: Dec. 14, 2010

(87) PCT Pub. No.: WO2008/137862
PCT Pub. Date: Nov. 13, 2008

(65) Prior Publication Data
US 2011/0105583 A1  May 5, 2011

Related U.S. Application Data

(60) Provisional application No. 60/927,621, filed on May 3, 2007.

(51) Int. Cl.
*C12N 15/85* (2006.01)
*C07H 21/04* (2006.01)
*C07H 21/02* (2006.01)
(52) U.S. Cl. .................. 435/325; 536/23.1; 536/24.5
(58) Field of Classification Search .................. None
See application file for complete search history.

(56) References Cited

U.S. PATENT DOCUMENTS

| 7,655,785 B1* | 2/2010 | Bentwich ............... 536/24.1 |
| 2002/0177568 A1* | 11/2002 | Stinchcomb et al. ........... 514/44 |
| 2005/0182005 A1 | 8/2005 | Tuschi |
| 2006/0003322 A1 | 1/2006 | Bentwich |
| 2006/0009409 A1 | 1/2006 | Woolf |
| 2007/0032441 A1 | 2/2007 | McSwiggen |
| 2007/0050146 A1 | 3/2007 | Bentwich |

FOREIGN PATENT DOCUMENTS

| WO | 2005018534 A2 | 3/2005 |
| WO | 2005/118806 A2 | 12/2005 |
| WO | 2007056826 A1 | 5/2007 |
| WO | 2008137867 A2 | 5/2008 |
| WO | 2008/088858 A2 | 7/2008 |
| WO | 2008088858 A2 | 7/2008 |
| WO | 2008/104974 A2 | 9/2008 |
| WO | 2008104974 A2 | 9/2008 |

OTHER PUBLICATIONS

Murchison, E.P., "Dicer in Mammary Tumor Stem Cell Maintenance," Annual Summary Report, Cold Spring Harbor Laboratory, Mar. 2007, <http://64.233.179.104/scholar?hl=en&lr=&q=cache:-9x03_AHXZgJ:handle.dtic.mil/100.2/ADA469955+mir-34+and+p53+status> [retrieved Nov. 16, 2008], 10 pages.
Xi, Y., et al., "Differentially Regulated Micro-RNAs and Actively Translated Messenger RNA Transcripts by Tumor Suppressor p53 in Colon Cancer," Clinical Cancer Research 12(7):2014-2024, Apr. 2006.
International Search Report dated Dec. 12, 2008, issued in corresponding International Application No. PCT/US2008/062681, filed May 5, 2008.
He et al., "A MicroRNA Component of the p53 Tumour Suppressor Network," Nature, 447(7148):1130-1134, Jun. 2007.
International Search Report, issued in related International Application No. PCT/US2008/062689, filed May 5, 2008.
Jackson et al., "Widespread siRNA 'Off-Target' Transcript Silencing mediated by Seed Region Sequence Complementarity," RNA, 12(7):1179-1187, Jul. 2006.
Khvorova et al., "Functional siRNAs and miRNAs Exhibit Stand Bias," Cell, 115(2):209-216, Oct. 2003.
Lim et al., "Microarray Analysis Shows that Some MicroRNAs Downregulate Large Numbers of Target mRNAs," Nature, 443(7027): 769-773, Feb. 2005.
Matranga et al., "Passenger-Strand Cleavage Facilitates Assembly of siRNA into Ago2-Containing RNAi Enzyme Complexes," Cell 123(4): 607-620, Nov. 18, 2008.
Schwarz et al., "Asymmetry in the Assembly of the RNAi Enzyme Complex," Cell, 115(2): 199-208, Oct. 2003.
Silva et al., "Second-Generation shRNA Libraries Covering the Mouse and Human Genomes," Nature Genetics, 37 (11): 1281-1288, Nov. 2005.

* cited by examiner

*Primary Examiner* — Amy Bowman
(74) *Attorney, Agent, or Firm* — Christensen O'Connor Johnson Kindness PLLC

(57) ABSTRACT

In one aspect, the invention generally relates to use of miR-34 as a biomarker to estimate TP53 function in a cell. In another aspect, the invention generally relates to multiple uses of miR-34 and siRNAs functionally and structurally related to miR-34 for the treatment of cancer.

14 Claims, 3 Drawing Sheets

MiR-34 FAMILY SEED REGIONS
```
hsa-miR-34a    UGGCAGUGUCUUAGCUGGUUGU    SEQ ID NO:1
hsa-miR-34b    AGGCAGUGUCAUUAGCUGAUUG    SEQ ID NO:4
hsa-miR-34c    AGGCAGUGUAGUUAGCUGAUUG    SEQ ID NO:7
hsa-miR-449    UGGCAGUGUAUUGUUAGCUGGU    SEQ ID NO:29
```
*Fig.1.*
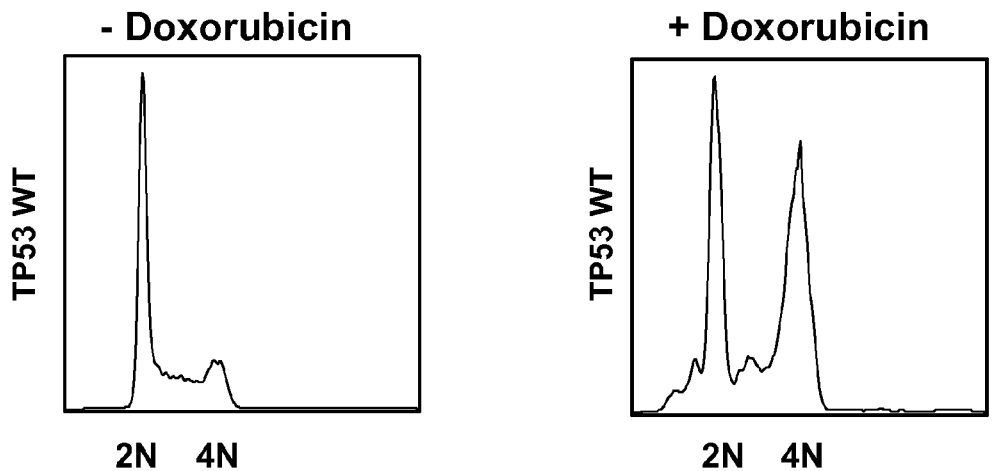
*Fig.2A.*          *Fig.2B.*
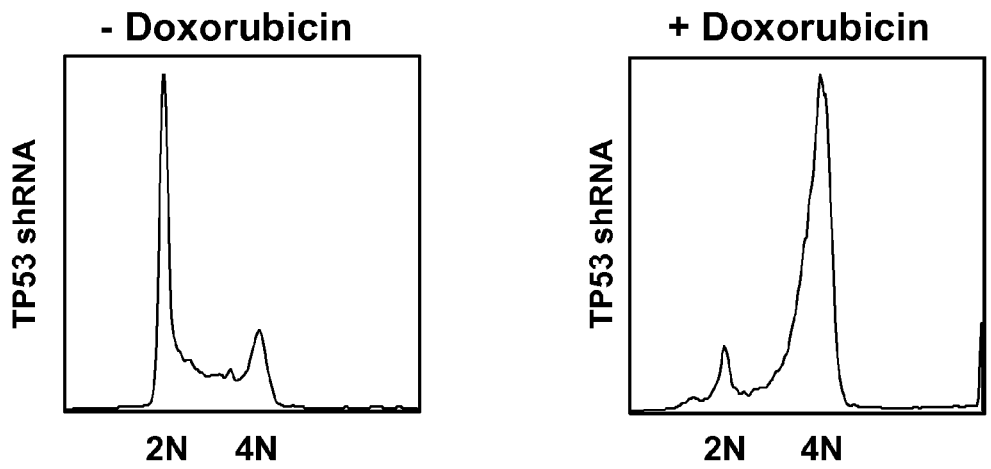
*Fig.2C.*          *Fig.2D.*

METHODS OF USING MIR34 AS A BIOMARKER FOR TP53 FUNCTIONAL STATUS

FIELD OF THE INVENTION

One aspect of the invention generally relates to use of miR-34 as a biomarker to estimate TP53 function in a cell. In a second aspect, the invention generally relates to multiple uses of miR-34 and siRNAs functionally and structurally related to miR-34 for the treatment of cancer.

BACKGROUND

The following is a discussion of relevant art pertaining to TP53 and RNAi. The discussion is provided only for understanding of the various embodiments of invention that follow. The summary and references cited throughout the specification herein are not an admission that any of the content below is prior art to the claimed invention.

The TP53 tumor suppressor is activated by protein stabilization following genotoxic stress. This activation can be induced by ultraviolet or ionizing radiation as well as a host of DNA-damaging chemotherapeutics such as doxorubicin (adriamycin), cisplatin, and bleomycin. Activation of TP53 leads to cell cycle arrest prior to entry into S phase and/or apoptosis. TP53 activation also initiates a number of DNA repair pathways (Fei and El'Deiry, 2003, *Oncogene* 22:5774-83). Mutations in TP53, which are present in about 50% of human cancers (Hollstein et al., 1991, *Science* 253:49-53), result in checkpoint defects and may contribute to uncontrolled cell proliferation, genomic instability, and accumulation of tumorigenic mutations (Prives and Hall, 1999, *J. Pathol.* 186:112-26). In the clinic, emphasis has been placed on identifying chemotherapeutics that are effective for both TP53-positive tumor cells and TP53-deficient tumor cells (Lowe et al., 1994, *Science* 266:807-810; Lacroix et al., 2006, *Endocrine-Related Cancer* 13:293-325; Levesque and Eastman, 2007, *Carcinogenesis* 28:13-20). Therefore, predicting TP53 pathway status in human tumors will be an important component for selecting an effective cancer therapeutic for a given cancer type.

Although DNA sequencing of TP53 can reveal inactivating mutations, the TP53 pathway can be inactivated by alternative mechanisms. For example, p19(ARF), which is encoded by the INK4a-ARF locus, inhibits cell proliferation by activating TP53 (Sherr et al., 2005, *Cold Spring Harbor Symp. Quant. Biol.* 70:129-37). Significantly, many human cancers exhibit deletion, silencing, or mutation of the INK4a-ARF locus. Other tumors over-express, or express aberrant splice forms of, MDM2, a key regulator of TP53 stability and transcriptional activity (Levav-Cohen et al., 2005, *Growth Factors* 23:183-92). TP53 pathway inactivation can also be caused by viral factors such as the human papilloma virus E6 protein, which binds to and targets TP53 for degradation. Therefore, predicting TP53 pathway integrity may not be straightforward in many patient tumors. Miller et al. (2005, *PNAS* 38:13550-55) developed a gene expression signature to predict TP53 pathway status of cancer patients and presented data showing the importance of TP53 pathway status in predicting clinical breast cancer behavior.

There is growing realization that miRNAs, in addition to functioning as regulators of development, can act as oncogenes and tumor suppressors (Akao et al., 2006, *Oncology Reports* 16:845-50; Esquela-Kerscher and Slack, 2006, *Nature Rev.*, 6:259-269; He et al., 2005, *Nature* 435:828-33) and that miRNA expression profiles can, under some circumstances, be used to diagnose and classify human cancers (Lu et al., 2005, *Nature* 435:834-38; Volinia et al., 2006, *PNAS* 103:2257-61; Yanaihara et al., 2006, *Cancer Cell* 9:189-198). Given the significance of TP53 in cancer and the importance of finding clinical biomarkers for TP53 status, there is need to identify RNA transcripts, including miRNAs, that are involved in regulation of the TP53 pathway.

SUMMARY

In one aspect, a method is provided for identifying an agent that modifies TP53 pathway activity in a subject. The method according to this aspect of the invention comprises (a) measuring the amount of miR-34 present in a first cell sample obtained from said subject that is not contacted with said agent; (b) contacting an agent with a second cell sample obtained from said subject; (c) measuring the amount of miR-34 present in said second cell sample; and (d) comparing said measured amount of miR-34 in said first population of cells to said measured amount of miR-34 in said second population of cells, wherein a difference in said measured amounts of miR-34 in said first population of cells compared to said second population of cells indicates that said agent modifies TP53 pathway activity in said subject.

In another aspect, a method is provided for classifying a cell sample from a subject as having an active TP53 pathway or an inactive TP53 pathway. The method according to this aspect of the invention comprises (a) obtaining a measured level of miR-34 present in a cell sample from said subject; and (b) comparing said obtained level of miR-34 with a baseline level of miR-34, wherein said baseline level of miR-34 correlates to a TP53 pathway activity status from TP53 pathway active cells or from TP53 pathway inactive cells; wherein said cell sample is classified as having an active TP53 pathway if said measured level of miR-34 is higher than said baseline level of miR-34 or said cell sample is classified as having an inactive TP53 pathway if said measured level of miR-34 is lower than said baseline level of miR-34.

In another aspect, a method is provided for inhibiting cell division of a mammalian cell. The method according this aspect of the invention comprises introducing into said cell an effective amount of a small interfering nucleic acid (siNA), wherein said siNA comprises a guide strand contiguous nucleotide sequence of at least 18 nucleotides, wherein said guide strand comprises a seed region consisting of nucleotide positions 1 to 12, wherein position 1 represents the 5' end of said guide strand and wherein said seed region comprises a nucleotide sequence of at least six contiguous nucleotides that is identical to six contiguous nucleotides within a sequence selected from the group consisting of SEQ ID NO:3, SEQ ID NO:6, SEQ ID NO:9, and SEQ ID NO:31.

In yet another aspect, a method is provided for treating a mammalian subject having a cancer. The method according to this aspect of the invention comprises (a) classifying a cancer cell sample from the subject as having an active TP53 pathway or an inactive TP53 pathway; and (b) treating a mammalian subject having an active TP53 pathway with a composition comprising a small interfering nucleic acid (siNA), wherein said siNA comprises a guide strand contiguous nucleotide sequence of at least 18 nucleotides, wherein said guide strand comprises a seed region consisting of nucleotide positions 1 to 12, wherein position 1 represents the 5' end of said guide strand and wherein said seed region comprises a nucleotide sequence of at least six contiguous nucleotides that is identical to six contiguous nucleotides within a sequence selected from the group consisting of SEQ ID NO:3, SEQ ID NO:6, SEQ ID NO:9, and SEQ ID NO:31.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows the RNA sequences of miR-34a, miR-34b, miR-34c, and miR-449 including corresponding "seed regions";

FIG. 2A is a histogram of cells with wildtype p53 showing the number of cells (Y axis) with a given DNA content (measured by fluorescence intensity, X axis);

FIG. 2B is a histogram of cells with wildtype p53 treated with doxorubicin showing the number of cells (Y axis) with a given DNA content (measured by fluorescence intensity, X axis);

FIG. 2C is a histogram of cells with wildtype p53 transfected with TP53 shRNA showing the number of cells (Y axis) with a given DNA content (measured by fluorescence intensity, X axis), FIG. 2D is a histogram of cells with wildtype p53 transfected with TP53 shRNA and treated with doxorubicin showing the number of cells (Y axis) with a given DNA content (measured by fluorescence intensity, X axis), showing that disruption of TP53 ablates the G0/G1 checkpoint following DNA damage;

DETAILED DESCRIPTION

Figure 3A:
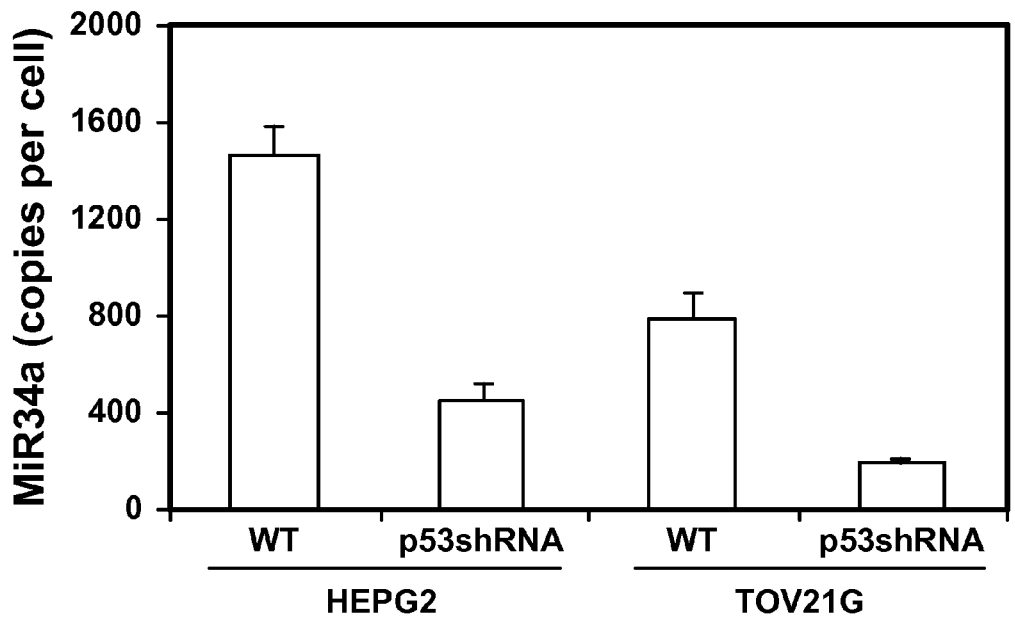
FIG. 3A graphically illustrates a comparison of miR-34a per cell copy number in a matched pair of cell lines HEPG2 or TOV21G either wild type (+) or deficient (−) for TP53 due to stable integration of a control vector or a vector expressing a TP53 shRNA, respectively, showing that miR-34 levels in a cell are correlated with TP53 status and can be induced by activation of TP53.

This section presents a detailed description of the many different aspects and embodiments that are representative of the inventions disclosed herein. This description is by way of several exemplary illustrations, of varying detail and specificity. Other features and advantages of these embodiments are apparent from the additional descriptions provided herein, including the different examples. The provided examples illustrate different components and methodology useful in practicing various embodiments of the invention. The examples are not intended to limit the claimed invention. Based on the present disclosure, the ordinary skilled artisan can identify and employ other components and methodology useful for practicing the present invention.

The present application claims priority from U.S. Provisional Application Ser. No. 60/927,621 filed on May 3, 2007, which is hereby incorporated by reference.

I. Definitions

Unless defined otherwise, all technical and scientific terms used herein have the meaning commonly understood by one of ordinary skill in the art to which this invention belongs. Practitioners are particularly directed to Sambrook et al. (1989) *Molecular Cloning: A Laboratory Manual,* 2d ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

It is contemplated that the use of the term "about" in the context of the present invention is to connote inherent problems with precise measurement of a specific element, characteristic, or other trait. Thus, the term "about," as used herein in the context of the claimed invention, simply refers to an amount or measurement that takes into account single or collective calibration and other standardized errors generally associated with determining that amount or measurement. For example, a concentration of "about" 100 mM of Tris can encompass an amount of 100 mM±0.5 mM, if 5 mM represents the collective error bars in arriving at that concentration. Thus, any measurement or amount referred to in this application can be used with the term "about" if that measurement or amount is susceptible to errors associated with calibration or measuring equipment, such as a scale, pipetteman, pipette, graduated cylinder, etc.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only, or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "approximately" or "about" in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

It is contemplated that any embodiment discussed in this specification can be implemented with respect to any method, kit, reagent, or composition of the invention, and vice versa. Furthermore, compositions of the invention can be used to achieve methods of the invention.

As used herein, the term "gene" has its meaning as understood in the art. However, it will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For clarity, the term gene generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid. In some cases, the gene includes regulatory sequences involved in transcription, or message production or composition. In other embodiments, the gene comprises transcribed sequences that encode for a protein, polypeptide or peptide. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof.

In particular embodiments, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

As used herein, the term "microRNA species", "microRNA", "miRNA", or "mi-R" refers to small, non-protein coding RNA molecules that are expressed in a diverse array of eukaryotes, including mammals. MicroRNA molecules typically have a length in the range of from 15 to 120 nucleotides, the size depending upon the specific microRNA species and the degree of intracellular processing. Mature, fully processed miRNAs are about 15 to 30, 15 to 25, or 20 to 30 nucleotides in length, and more often between about 16 to 24, 17 to 23, 18 to 22, 19 to 21, or 21 to 24 nucleotides in length. MicroRNAs include processed sequences as well as corresponding long primary transcripts (pri-miRNAs) and processed precursors (pre-miRNAs). Some microRNA molecules function in living cells to regulate gene expression via RNA interference. A representative set of microRNA species is described in the publicly available miRBase sequence database as described in Griffith-Jones et al., *Nucleic Acids Research* 32:D109-D111 (2004) and Griffith-Jones et al., *Nucleic Acids Research* 34:D140-D144 (2006), accessible on the World Wide Web at the Wellcome Trust Sanger Institute website.

As used herein, the term "microRNA family" refers to a group of microRNA species that share identity across at least 6 consecutive nucleotides within nucleotide positions 1 to 12 of the 5' end of the microRNA molecule, also referred to as the "seed region", as described in Brennecke, J. et al., PloS biol 3(3):pe85 (2005).

As used herein, the term "microRNA family member" refers to a microRNA species that is a member of a microRNA family.

As used herein, the term "RNA interference" or "RNAi" refers to the silencing or decreasing of gene expression by iRNA agents (e.g., siRNAs, miRNAs, shRNAs), via the process of sequence-specific, post-transcriptional gene silencing in animals and plants, initiated by an iRNA agent that has a seed region sequence in the iRNA guide strand that is complementary to a sequence of the silenced gene.

As used herein, the term an "iNA agent" (abbreviation for "interfering nucleic acid agent"), refers to an nucleic acid agent, for example RNA, or chemically modified RNA, which can down-regulate the expression of a target gene. While not wishing to be bound by theory, an iNA agent may act by one or more of a number of mechanisms, including post-transcriptional cleavage of a target mRNA, or pre-transcriptional or pre-translational mechanisms. An iNA agent can include a single strand (ss) or can include more than one strands, e.g., it can be a double stranded (ds) iNA agent.

As used herein, the term "single strand iRNA agent" or "ssRNA" is an iRNA agent which consists of a single molecule. It may include a duplexed region, formed by intra-strand pairing, e.g., it may be, or include, a hairpin or panhandle structure. The ssRNA agents of the present invention include transcripts that adopt stem-loop structures, such as shRNA, that are processed into a double stranded siRNA.

As used herein, the term "ds iNA agent" is a dsNA (double stranded nucleic acid (NA)) agent that includes two strands that are not covalently linked, in which interchain hybridization can form a region of duplex structure. The dsNA agents of the present invention include silencing dsNA molecules that are sufficiently short that they do not trigger the interferon response in mammalian cells.

As used herein, the term "siRNA" refers to a small interfering RNA. siRNA include short interfering RNA of about 15-60, 15-50, 15-50, or 15-40 (duplex) nucleotides in length, more typically about 15-30, 15-25, or 19-25 (duplex) nucleotides in length, and preferably about 20-24 or about 21-22 or 21-23 (duplex) nucleotides in length (e.g., each complementary sequence of the double stranded siRNA is 15-60, 15-50, 15-50, 15-40, 15-30, 15-25, or 19-25 nucleotides in length, preferably about 20-24 or about 21-22 or 21-23 nucleotides in length, preferably 19-21 nucleotides in length, and the double stranded siRNA is about 15-60, 15-50, 15-50, 15-40, 15-30, 15-25, or 19-25 base pairs in length, preferably about 20-24 or about 21-22 or 19-21 or 21-23 base pairs in length). siRNA duplexes may comprise 3' overhangs of about 1 to about 4 nucleotides, preferably of about 2 to about 3 nucleotides and 5' phosphate termini. In some embodiments, the siRNA lacks a terminal phosphate.

Non limiting examples of siRNA molecules of the invention may include a double-stranded polynucleotide molecule comprising self-complementary sense and antisense regions, wherein the antisense region comprises nucleotide sequence that is complementary to nucleotide sequence in a target nucleic acid molecule or a portion thereof (alternatively referred to as the guide region, or guide strand when the molecule contains two separate strands) and the sense region having nucleotide sequence corresponding to the target nucleic acid sequence or a portion thereof (also referred as the passenger region, or the passenger strand, when the molecule contains two separate strands). The siRNA can be assembled from two separate oligonucleotides, where one strand is the sense strand and the other is the antisense strand, wherein the antisense and sense strands are self-complementary (i.e., each strand comprises a nucleotide sequence that is complementary to the nucleotide sequence in the other strand; such as where the antisense strand and sense strand form a duplex or double stranded structure, for example wherein the double stranded region is about 18 to about 30, e.g., about 18, 19, 20, 21, 22, 23, 24, 25, 26, 27, 28, 29, or 30 base pairs); the antisense strand (guide strand) comprises nucleotide sequence that is complementary to nucleotide sequence in a target nucleic acid molecule or a portion thereof and the sense strand (passenger strand) comprises nucleotide sequence corresponding to the target nucleic acid sequence or a portion thereof (e.g., about 15 to about 25 nucleotides of the siRNA molecule are complementary to the target nucleic acid or a portion thereof). Typically, a short interfering RNA (siRNA) refers to a double-stranded RNA molecule of about 17 to about 29 base pairs in length, preferably from 19-21 base pairs, one strand of which is complementary to a target mRNA, that when added to a cell having the target mRNA, or produced in the cell in vivo, causes degradation of the target mRNA. Preferably the siRNA is perfectly complementary to the target mRNA. But it may have one or two mismatched base pairs.

Alternatively, the siRNA is assembled from a single oligonucleotide, where the self-complementary sense and antisense regions of the siRNA are linked by means of a nucleic acid based or non-nucleic acid-based linker(s). The siRNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof, and the sense region having nucleotide sequence corresponding to the target nucleic acid sequence or a portion thereof. The siRNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof, and the sense region having nucleotide sequence corresponding to the target nucleic acid sequence or a portion thereof, and wherein the circular polynucleotide can be processed either in vivo or in vitro to generate an active siRNA molecule capable of mediating RNAi. The siRNA can also comprise a single stranded polynucleotide having nucleotide sequence complementary to nucleotide sequence in a target nucleic acid molecule or a portion thereof (for example, where such siRNA molecule does not require the presence within the siRNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell* 110:563-574 and Schwarz et al., 2002, *Molecular Cell*, 10:537-568), or 5',3'-diphosphate. In certain embodiments, the siRNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siRNA molecules of the invention comprise nucleotide sequence that is complementary to nucleotide sequence of a target gene. In another embodiment, the siRNA molecule of the invention interacts with the nucleotide sequence of a target gene in a manner that causes inhibition of expression of the target gene.

As used herein, the siRNA molecules need not be limited to those molecules containing only RNA, but may further encompasses chemically-modified nucleotides and non-nucleotides. WO2005/078097; WO2005/0020521 and WO2003/070918 detail various chemical modifications to RNAi molecules, wherein the contents of each reference are hereby incorporated by reference in their entirety. In certain embodiments, for example, the short interfering nucleic acid molecules may lack 2'-hydroxy (2'-OH) containing nucleotides. The siRNA can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., 2002 *PNAS USA* 99:9942-7; Calegari et al., 2002, *PNAS USA* 99:14236; Byrom et al., 2003, *Ambion TechNotes* 10(1):4-6; Kawasaki et al., 2003, *Nucleic Acids Res.* 31:981-7; Knight and Bass, 2001, *Science* 293:2269-71; and Robertson et al., 1968, *J. Biol. Chem.* 243:82). The long dsRNA can encode for an entire gene transcript or a partial gene transcript.

As used herein, "percent modification" refers to the number of nucleotides in each strand of the siRNA, or in the collective dsRNA, that have been modified. Thus 19% modification of the antisense strand refers to the modification of up to 4 nucleotides/bp in a 21 nucleotide sequence (21 mer). 100% refers to a fully modified dsRNA. The extent of chemical modification will depend upon various factors well known to one skilled in the art. Such as, for example, target mRNA, off-target silencing, degree of endonuclease degradation, etc.

As used herein, the term "shRNA" or "short hairpin RNAs" refers to an RNA molecule that forms a stem-loop structure in physiological conditions, with a double-stranded stem of about 17 to about 29 base pairs in length, wherein one strand of the base-paired stem is complementary to the mRNA of a target gene. The loop of the shRNA stem-loop structure may be any suitable length that allows inactivation of the target gene in vivo. While the loop may be from 3 to 30 nucleotides in length, typically it is 1-10 nucleotides in length. The base paired stem may be perfectly base paired or may have 1 or 2 mismatched base pairs. The duplex portion may, but typically does not, contain one or more bulges consisting of one or more unpaired nucleotides. The shRNA may have non-base-paired 5' and 3' sequences extending from the base-paired stem. Typically, however, there is no 5' extension. The first nucleotide of the shRNA at the 5' end is a G, because this is the first nucleotide transcribed by polymerase III. If G is not present as the first base in the target sequence, a G may be added before the specific target sequence. The 5' G typically forms a portion of the base-paired stem. Typically, the 3' end of the shRNA is a poly U segment that is a transcription termination signal and does not form a base-paired structure. As described in the application and known to one skilled in the art, shRNAs are processed into siRNAs by the conserved cellular RNAi machinery. Thus shRNAs are precursors of siRNAs and are, in general, similarly capable of inhibiting expression of a target mRNA transcript. For the purpose of description, in certain embodiments, the shRNA constructs of the invention target one or more mRNAs that are targeted by miR-34a, miR-34b, miR-34c or miR-449. The strand of the shRNA that is antisense to the target gene transcript is also known as the "guide strand".

As used herein, the term "microRNA responsive target site" refers to a nucleic acid sequence ranging in size from about 5 to about 25 nucleotides (such as 5, 6, 7, 8, 9, 10, 11, 12, 13, 14, 15, 16, 17, 18, 19, 20, 21, 22, 23, 24, or 25 nucleotides) that is complementary, or essentially complementary, to at least a portion of a microRNA molecule. In some embodiments, the microRNA responsive target site comprises at least 6 consecutive nucleotides, at least 7 consecutive nucleotides, at least 8 consecutive nucleotides, or at least 9 nucleotides that are complementary to the seed region of a microRNA molecule (i.e., within nucleotide positions 1 to 12 of the 5' end of the microRNA molecule, referred to as the "seed region".

The phrase "inhibiting expression of a target gene" refers to the ability of an RNAi agent, such as an siRNA, to silence, reduce, or inhibit expression of a target gene. Said another way, to "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the RNAi agent. For example, an embodiment of the invention proposes inhibiting, down-regulating, or reducing expression of one or more TP53 pathway genes, by introduction of an miR-34a-like siRNA molecule, below the level observed for that TP53 pathway gene in a control cell to which an mi-34a-like siRNA molecule has not been introduced. In another embodiment, inhibition, down-regulation, or reduction contemplates inhibition of the target mRNA below the level observed in the presence of, for example, an siRNA molecule with scrambled sequences or with mismatches. In yet another embodiment, inhibition, down-regulation, or reduction of gene expression with a siRNA molecule of the instant invention is greater in the presence of the invention siRNA, e.g., siRNA that down-regulates one or more TP53 pathway gene mRNAs levels, than in its absence. In one embodiment, inhibition, down-regulation, or reduction of gene expression is associated with post transcriptional silencing, such as RNAi mediated cleavage of a target nucleic acid molecule (e.g. RNA) or inhibition of translation.

To examine the extent of gene silencing, a test sample (e.g., a biological sample from an organism of interest expressing the target gene(s) or a sample of cells in culture expressing the target gene(s)) is contacted with an siRNA that silences, reduces, or inhibits expression of the target gene(s). Expression of the target gene in the test sample is compared to expression of the target gene in a control sample (e.g., a biological sample from an organism of interest expressing the target gene or a sample of cells in culture expressing the target gene) that is not contacted with the siRNA. Control samples (i.e., samples expressing the target gene) are assigned a value of 100%. Silencing, inhibition, or reduction of expression of a target gene is achieved when the value of the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, e.g., examination of protein or mRNA levels using techniques known to those of skill in the art such as dot blots, northern blots, in situ hybridization, ELISA, microarray hybridization, immunoprecipitation, enzyme function, as well as phenotypic assays known to those of skill in the art.

An "effective amount" or "therapeutically effective amount" of an siRNA or an RNAi agent is an amount sufficient to produce the desired effect, e.g., inhibition of expression of a target sequence in comparison to the normal expression level detected in the absence of the siRNA or RNAi agent. Inhibition of expression of a target gene or target sequence by an siRNA or RNAi agent is achieved when the expression level of the target gene mRNA or protein is about 90%, 80%, 70%, 60%, 50%, 40%, 30%, 25%, 20%, 15%, 10%, 5%, or 0% relative to the expression level of the target gene mRNA or protein of a control sample.

As used herein, the term "isolated" in the context of an isolated nucleic acid molecule, is one which is altered or removed from the natural state through human intervention. For example, an RNA naturally present in a living animal is not "isolated." A synthetic RNA or dsRNA or microRNA molecule partially or completely separated from the coexisting materials of its natural state, is "isolated." Thus, an miRNA molecule which is deliberately delivered to or expressed in a cell is considered an "isolated" nucleic acid molecule.

By "modulate" is meant that the expression of the gene, or level of RNA molecule or equivalent RNA molecules encoding one or more proteins or protein subunits, or activity of one or more proteins or protein subunits is up-regulated or down-regulated, such that expression, level, or activity is greater than or less than that observed in the absence of the modulator. For example, the term "modulate" can mean "inhibit," but the use of the word "modulate" is not limited to this definition.

As used herein, "RNA" refers to a molecule comprising at least one ribonucleotide residue. The term "ribonucleotide" means a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of an RNAi agent or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the term "complementary" refers to nucleic acid sequences that are capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA.

As used herein, the term "essentially complementary" with reference to microRNA target sequences refers to microRNA target nucleic acid sequences that are longer than 8 nucleotides that are complementary (an exact match) to at least 8 consecutive nucleotides of the 5' portion of a microRNA molecule from nucleotide positions 1 to 12, (also referred to as the "seed region"), and are at least 65% complementary (such as at least 70%, at least 75%, at least 80%, at least 85%, at least 90%, at least 95%, or at least 96% identical) across the remainder of the microRNA target nucleic acid sequence as compared to a naturally occurring miR-34 family member. The comparison of sequences and determination of percent identity and similarity between two sequences can be accomplished using a mathematical algorithm of Karlin and Altschul (1990, *PNAS* 87:2264-2268), modified as in Karlin and Altschul (1993, *PNAS* 90:5873-5877). Such an algorithm is incorporated into the NBLAST and XBLAST programs of Altschul et al. (1990 *J. Mol. Biol.* 215:403-410).

As used herein, the term "gene" encompasses the meaning known to one of skill in the art, i.e., a nucleic acid (e.g., DNA or RNA) sequence that comprises coding sequences necessary for the production of an RNA and/or a polypeptide, or its precursor as well as noncoding sequences (untranslated regions) surrounding the 5' and 3' ends of the coding sequences. The term "gene" encompasses both cDNA and genomic forms of a gene. The term "gene" also encompasses nucleic acid sequences that comprise microRNAs and other non-protein encoding sequences, including, for example, transfer RNAs, ribosomal RNAs, etc. A functional polypeptide can be encoded by a full length coding sequence or by any portion of the coding sequence as long as the desired activity or functional properties (e.g., enzymatic activity, ligand binding, signal transduction, antigenic presentation) of the polypeptide are retained. The sequences which are located 5' of the coding region and which are present on the mRNA are referred to as 5' untranslated sequences ("5'UTR"). The sequences which are located 3' or downstream of the coding region and which are present on the mRNA are referred to as 3' untranslated sequences, or ("3'UTR").

The term "gene expression", as used herein, refers to the process of transcription and translation of a gene to produce a gene product, be it RNA or protein. Thus, modulation of gene expression may occur at any one or more of many levels, including transcription, post-transcriptional processing, translation, post-translational modification, and the like.

As used herein, the term "expression cassette" refers to a nucleic acid molecule which comprises at least one nucleic acid sequence that is to be expressed, along with its transcription and translational control sequences. The expression cassette typically includes restriction sites engineered to be present at the 5' and 3' ends such that the cassette can be easily inserted, removed, or replaced in a gene delivery vector. Changing the cassette will cause the gene delivery vector into which it is incorporated to direct the expression of a different sequence.

As used herein, the term "phenotype" encompasses the meaning known to one of skill in the art, including modulation of the expression of one or more genes, as measured by gene expression analysis or protein expression analysis.

As used herein, the term "proliferative disease" or "cancer" as used herein refers to any disease, condition, trait, genotype or phenotype characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia; AIDS related cancers such as Kaposi's sarcoma; breast cancers; bone cancers such as osteosarcoma, chondrosarcomas, Ewing's sarcoma, fibrosarcomas, giant cell tumors, adamantinomas, and chordomas; brain cancers such as meningiomas, glioblastomas, lower-grade astrocytomas, oligodendrocytomas, pituitary tumors, schwannomas, and metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and any other cancer or proliferative disease, condition, trait, genotype or phenotype that can respond to the modulation of disease-related gene expression in a cell or tissue, alone or in combination with other therapies.

As used herein, the term "source of biological knowledge" refers to information that describes the function (e.g., at molecular, cellular, and system levels), structure, pathological roles, toxicological implications, etc., of a multiplicity of genes. Various sources of biological knowledge can be used for the methods of the invention, including databases and information collected from public sources such as Locuslink, Unigene, SwissTrEMBL, etc., and organized into a relational database following the concept of the central dogma of molecular biology. In some embodiments, the annotation systems used by the Gene Ontology (GO) Consortium or similar systems are employed. GO is a dynamic controlled vocabulary for molecular biology which can be applied to all organisms. As knowledge of gene function is accumulating and changing, it is developed and maintained by the Gene Ontology™ Consortium (*Gene Ontology*: tool for the unification of biology. The Gene Ontology Consortium (2000), *Nature Genet.* 25:25-29)).

As used herein, the term to "inhibit the proliferation of a mammalian cell" means to kill the cell, or permanently or temporarily arrest the growth of the cell. Inhibition of a mammalian cell can be inferred if the number of such cells, either in an in vitro culture vessel, or in a subject, remains constant or decreases after administration of the compositions of the invention. An inhibition of tumor cell proliferation can also be inferred if the absolute number of such cells increases, but the rate of tumor growth decreases.

As used herein, the terms "measuring expression levels," "obtaining an expression level" and the like, include methods that quantify a gene expression level of, for example, a transcript of a gene, including microRNA (miRNA) or a protein encoded by a gene, as well as methods that determine whether a gene of interest is expressed at all. Thus, an assay which provides a "yes" or "no" result without necessarily providing quantification, of an amount of expression is an assay that "measures expression" as that term is used herein. Alternatively, a measured or obtained expression level may be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix (see for example, U.S. Pat. No. 5,569,588) nuclease protection, RT-PCR, microarray profiling, differential display, 2D gel electrophoresis, SELDI-TOF, ICAT, enzyme assay, antibody assay, and the like.

As used herein "miR-34 family" refers to miR-34a, miR34b, miR34 c, and miR-449.

As used herein, "miR-34" refers to one or more of miR-34a, miR-34b and miR34c.

As used herein, "miR-34a" refers to SEQ ID NO:1 and precursor RNAs sequences thereof, an example of which is SEQ ID NO:2.

As used herein, "miR-34a seed region" refers to SEQ ID NO:3

As used herein, "miR-34b" refers to SEQ ID NO:4 and precursor RNAs sequences thereof, an example of which is SEQ ID NO:5.

As used herein, "miR-34b seed region" refers to SEQ ID NO:6

As used herein, "miR-34c" refers to SEQ ID NO:7 and precursor RNAs sequences thereof, an example of which is SEQ ID NO:8.

As used herein, "miR-34c seed region" refers to SEQ ID NO:9

As used herein "miR-449" refers to SEQ ID NO:29 and precursor RNAs sequences thereof, an example of which is SEQ ID NO:30.

As used herein, "miR-449 seed region" refers to SEQ ID NO:31.

As used herein, an "isolated nucleic acid" is a nucleic acid molecule that exists in a physical form that is non-identical to any nucleic acid molecule of identical sequence as found in nature; "isolated" does not require, although it does not prohibit, that the nucleic acid so described has itself been physically removed from its native environment. For example, a nucleic acid can be said to be "isolated" when it includes nucleotides and/or internucleoside bonds not found in nature. When instead composed of natural nucleosides in phosphodiester linkage, a nucleic acid can be said to be "isolated" when it exists at a purity not found in nature, where purity can be adjudged with respect to the presence of nucleic acids of other sequence, with respect to the presence of proteins, with respect to the presence of lipids, or with respect to the presence of any other component of a biological cell, or when the nucleic acid lacks sequence that flanks an otherwise identical sequence in an organism's genome, or when the nucleic acid possesses sequence not identically present in nature. As so defined, "isolated nucleic acid" includes nucleic acids integrated into a host cell chromosome at a heterologous site, recombinant fusions of a native fragment to a heterologous sequence, recombinant vectors present as episomes or as integrated into a host cell chromosome.

The terms "over-expression", "over-expresses", "over-expressing" and the like, refer to the state of altering a subject such that expression of one or more genes in said subject is significantly higher, as determined using one or more statistical tests, than the level of expression of said gene or genes in the same unaltered subject or an analogous unaltered subject.

As used herein, a "purified nucleic acid" represents at least 10% of the total nucleic acid present in a sample or preparation. In preferred embodiments, the purified nucleic acid represents at least about 50%, at least about 75%, or at least about 95% of the total nucleic acid in an isolated nucleic acid sample or preparation. Reference to "purified nucleic acid" does not require that the nucleic acid has undergone any purification and may include, for example, chemically synthesized nucleic acid that has not been purified.

As used herein, "specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least 2-fold, more typically by at least 10-fold, often at least 100-fold; when used to detect analyte, specific binding is sufficiently discriminatory when determinative of the presence of the analyte in a heterogeneous (inhomogeneous) sample. Typically, the affinity or avidity of a specific binding reaction is least about 1 µM.

As used herein, "subject", as refers to an organism or to a cell sample, tissue sample or organ sample derived therefrom, including, for example, cultured cell lines, biopsy, blood sample of fluid sample containing a cell. For example, an organism may be an animal, including but not limited to, an animal such as a cow, a pig, a mouse, a rat, a chicken, a cat, a dog, etc., and is usually a mammal, such as a human.

As used herein, "TP53 pathway" refers to proteins, and their corresponding genes, that function both upstream and downstream of TP53, including, for example, proteins that are involved in or required for perception of DNA damage, modulation of TP53 activity, cell cycle arrest, and apoptosis. TP53 pathway includes, but is not limited to, the genes, and proteins encoded thereby, listed in Table 1 (see also Vogelstein, et al., 2000, *Nature* 408:307-310; Woods and Vousden, 2001, *Experimental Cell Research* 264:56-66; El-Deiry, 1998, *Semin. Cancer Biology* 8:345-357; and Prives and Hall, 1999, *J. Pathol.* 1999 187:112-126).

TABLE 1

TP53 Pathway Genes

| GeneBank | Symbol | Description | GO Term |
|---|---|---|---|
| NM_002954 | RPS27A | Ribosomal protein S27a | Intracellular; Protein biosynthesis; Structural constituent of ribosome; Ribosome; |
| NM_012138 | AATF | Apoptosis antagonizing transcription factor | Nucleus; Anti-apoptosis; Transcription factor activity; |
| NM_001160 | APAF1 | Apoptotic peptidase activating factor | ATP binding; Protein binding; Regulation of apoptosis; Cytosol; Intracellular; Caspase activation via cytochrome c; Neurogenesis; Caspase activator activity; |
| NM_000051 | ATM | Ataxia telangiectasia mutated (includes complementation groups A, C and D) | Transferase activity; Signal transduction; DNA binding; Regulation of transcription, DNA-dependent; Nucleus; Protein serine/threonine kinase activity; Negative regulation of cell cycle; Transcription factor activity; Intracellular; DNA repair; Phosphotransferase activity, alcohol group as acceptor; Meiotic recombination; |
| NM_001184 | ATR | Ataxia telangiectasia and Rad3 related | Development; Protein kinase activity; Cell cycle; Cell cycle checkpoint; DNA repair; |
| NM_004323 | BAG1 | BCL2-associated athanogene | Receptor signaling protein activity; Cytoplasm; Apoptosis; Anti-apoptosis; Cell surface receptor linked signal transduction; Protein folding; Unfolded protein binding; |
| NM_001702 | BAI1 | Brain-specific angiogenesis inhibitor 1 | Cell adhesion; Signal transduction; Protein binding; Negative regulation of cell proliferation; Integral to plasma membrane; Axonogenesis; Intercellular |

TABLE 1-continued

TP53 Pathway Genes

| GeneBank | Symbol | Description | GO Term |
|---|---|---|---|
| | | | junction; G-protein coupled receptor activity; Neuropeptide signaling pathway; Peripheral nervous system development; Brain-specific angiogenesis inhibitor activity; |
| NM_001188 | BAK1 | BCL2-antagonist/killer 1 | Integral to membrane; Apoptotic mitochondrial changes; Induction of apoptosis; Regulation of apoptosis; |
| NM_004656 | BAP1 | BRCA1 associated protein-1 (ubiquitin carboxy-terminal hydrolase) | Nucleus; Negative regulation of cell proliferation; Ubiquitin-dependent protein catabolism; Peptidase activity; Protein modification; Ubiquitin thiolesterase activity; |
| NM_004324 | BAX | BCL2-associated X protein | Integral to membrane; Negative regulation of cell cycle; Apoptotic mitochondrial changes; Induction of apoptosis; Regulation of apoptosis; Molecular_function unknown; Apoptosis; Germ cell development; Induction of apoptosis by extracellular signals; Negative regulation of survival gene product activity; |
| NM_000633 | BCL2 | B-cell CLL/lymphoma 2 | Integral to membrane; Protein binding; Cell growth and/or maintenance; Regulation of apoptosis; Anti-apoptosis; Humoral immune response; Negative regulation of cell proliferation; Regulation of cell cycle; Mitochondrial outer membrane; Mitochondrion; |
| NM_004049 | BCL2A1 | BCL2-related protein A1 | Regulation of apoptosis; Anti-apoptosis; Intracellular; |
| NM_001196 | BID | BH3 interacting domain death agonist | Apoptotic mitochondrial changes; Regulation of apoptosis; Mitochondrion; Death receptor binding; Induction of apoptosis via death domain receptors; Cytosol; Membrane fraction; |
| NM_001168 | BIRC5 | Baculoviral IAP repeat-containing 5 (survivin) | Microtubule binding; Apoptosis; Anti-apoptosis; Zinc ion binding; Intracellular; Caspase inhibitor activity; G2/M transition of mitotic cell cycle; Cysteine protease inhibitor activity; Protease inhibitor activity; Spindle microtubule; |
| NM_004052 | BNIP3 | BCL2/adenovirus E1B 19 kDa interacting protein 3 | Integral to membrane; Protein binding; Apoptosis; Anti-apoptosis; Mitochondrion; |
| NM_007294 | BRCA1 | Breast cancer 1, early onset | Nucleus; Protein binding; Negative regulation of cell cycle; Regulation of apoptosis; Zinc ion binding; Ubiquitin-protein ligase activity; Protein ubiquitination; Ubiquitin ligase complex; Regulation of transcription from Pol II promoter; Transcriptional activator activity; Intracellular; Extracellular space; Transcription factor complex; Transcription coactivator activity; Damaged DNA binding; Tubulin binding; DNA damage response, signal transduction by p53 class mediator resulting in transcription of p21 class mediator; Negative regulation of centriole replication; Positive regulation of DNA repair; Regulation of cell proliferation; Regulation of transcription from Pol III promoter; Gamma-tubulin ring complex; |

TABLE 1-continued

TP53 Pathway Genes

| GeneBank | Symbol | Description | GO Term |
|---|---|---|---|
| NM_000059 | BRCA2 | Breast cancer 2, early onset | Nucleic acid binding; Nucleus; Protein binding; Regulation of cell cycle; Extracellular space; Transcription coactivator activity; DNA repair; Single-stranded DNA binding; Chromatin remodeling; Double-strand break repair via homologous recombination; Establishment and/or maintenance of chromatin architecture; Regulation of transcription; Secretory granule; Mitotic checkpoint; Regulation of S phase of mitotic cell cycle; |
| NM_006763 | BTG2 | BTG family, member 2 | Regulation of transcription, DNA-dependent; Negative regulation of cell proliferation; Transcription factor activity; DNA repair; |
| NM_032982 | CASP2 | Caspase 2, apoptosis-related cysteine peptidase (neural precursor cell expressed, developmentally down-regulated 2) | Hydrolase activity; Proteolysis and peptidolysis; Protein binding; Regulation of apoptosis; Caspase activity; Cysteine-type peptidase activity; Apoptotic program; Enzyme binding; Intracellular; |
| NM_001229 | CASP9 | Caspase 9, apoptosis-related cysteine peptidase | Proteolysis and peptidolysis; Protein binding; Regulation of apoptosis; Caspase activity; Apoptotic program; Intracellular; Caspase activation via cytochrome c; Enzyme activator activity; |
| NM_057735 | CCNE2 | Cyclin E2 | Nucleus; Regulation of cell cycle; Regulation of cyclin dependent protein kinase activity; Cell cycle checkpoint; |
| NM_004354 | CCNG2 | Cyclin G2 | Cell cycle; Cell cycle checkpoint; Mitosis; |
| NM_001239 | CCNH | Cyclin H | Regulation of transcription, DNA-dependent; Nucleus; Cell cycle; Regulation of cyclin dependent protein kinase activity; DNA repair; |
| NM_001786 | CDC2 | Cell division cycle 2, G1 to S and G2 to M | ATP binding; Transferase activity; Protein amino acid phosphorylation; Nucleus; Protein serine/threonine kinase activity; Protein-tyrosine kinase activity; Cyclin-dependent protein kinase activity; Mitosis; Traversing start control point of mitotic cell cycle; |
| NM_001789 | CDC25A | Cell division cycle 25A | Hydrolase activity; Cell proliferation; Intracellular; Regulation of cyclin dependent protein kinase activity; Mitosis; Protein amino acid dephosphorylation; Protein tyrosine phosphatase activity; M phase of mitotic cell cycle; |
| NM_001790 | CDC25C | Cell division cycle 25C | Hydrolase activity; Cell proliferation; Nucleus; Regulation of cyclin dependent protein kinase activity; Protein amino acid dephosphorylation; Protein tyrosine phosphatase activity; Regulation of mitosis; Traversing start control point of mitotic cell cycle; |
| NM_000075 | CDK4 | Cyclin-dependent kinase 4 | ATP binding; Transferase activity; Protein amino acid phosphorylation; Regulation of cell cycle; Cyclin-dependent protein kinase activity; Protein kinase activity; G1/S transition of mitotic cell cycle; |

TABLE 1-continued

TP53 Pathway Genes

| GeneBank | Symbol | Description | GO Term |
|---|---|---|---|
| NM_001799 | CDK7 | Cyclin-dependent kinase 7 (MO15 homolog, Xenopus laevis, cdk-activating kinase) | ATP binding; Transferase activity; Protein amino acid phosphorylation; Regulation of transcription, DNA-dependent; Nucleus; Cyclin-dependent protein kinase activity; Regulation of cyclin dependent protein kinase activity; DNA repair; Transcription initiation from Pol II promoter; |
| NM_000389 | CDKN1A | Cyclin-dependent kinase inhibitor 1A (p21, Cip1) | Nucleus; Negative regulation of cell proliferation; Cell cycle arrest; Protein kinase activity; Cyclin-dependent protein kinase inhibitor activity; Regulation of cyclin dependent protein kinase activity; Kinase activity; Induction of apoptosis by intracellular signals; |
| NM_000077 | CDKN2A | Cyclin-dependent kinase inhibitor 2A (melanoma, p16, inhibits CDK4) | Nucleus; Negative regulation of cell cycle; Negative regulation of cell proliferation; Cell cycle arrest; Cell cycle; Cyclin-dependent protein kinase inhibitor activity; Regulation of cyclin dependent protein kinase activity; Kinase activity; Cell cycle checkpoint; |
| NM_001274 | CHEK1 | CHK1 checkpoint homolog (S. pombe) | ATP binding; Transferase activity; Protein amino acid phosphorylation; Nucleus; Protein serine/threonine kinase activity; Negative regulation of cell proliferation; Cell cycle; Regulation of cyclin dependent protein kinase activity; Meiotic recombination; DNA damage checkpoint; Response to DNA damage stimulus; Gametogenesis; Condensed nuclear chromosome; |
| NM_007194 | CHEK2 | CHK2 checkpoint homolog (S. pombe) | ATP binding; Transferase activity; Protein amino acid phosphorylation; Nucleus; Protein serine/threonine kinase activity; Cell growth and/or maintenance; Protein kinase activity; Cell cycle; DNA damage checkpoint; Response to DNA damage stimulus; |
| NM_004804 | WDR39 | WD repeat domain 39 | Nucleus; Positive regulation of cell proliferation; Regulation of transcription from Pol II promoter; |
| NM_001300 | KLF6 | Kruppel-like factor 6 | Nucleic acid binding; DNA binding; Regulation of transcription, DNA-dependent; Nucleus; Zinc ion binding; Transcriptional activator activity; Cell growth; B-cell differentiation; |
| NM_003805 | CRADD | CASP2 and RIPK1 domain containing adaptor with death domain | Signal transduction; Protein binding; Regulation of apoptosis; Induction of apoptosis via death domain receptors; Intracellular; |
| NM_001554 | CYR61 | Cysteine-rich, angiogenic inducer, 61 | Cell adhesion; Cell proliferation; Regulation of cell growth; Extracellular; Heparin binding; Chemotaxis; Insulin-like growth factor binding; Morphogenesis; |
| NM_004938 | DAPK1 | Death-associated protein kinase 1 | ATP binding; Transferase activity; Protein amino acid phosphorylation; Protein kinase cascade; Signal transduction; Protein serine/threonine kinase activity; Apoptosis; Induction of apoptosis by extracellular signals; Calmodulin binding; Actin cytoskeleton; Calcium- and calmodulin-dependent protein kinase activity; Calmodulin-dependent protein kinase I activity; |

TABLE 1-continued

TP53 Pathway Genes

| GeneBank | Symbol | Description | GO Term |
|---|---|---|---|
| NM_001350 | DAXX | Death-associated protein 6 | Calcium ion binding; Regulation of transcription, DNA-dependent; Nucleus; Apoptosis; |
| NM_005225 | E2F1 | E2F transcription factor 1 | Regulation of transcription, DNA-dependent; Nucleus; Apoptosis; Regulation of cell cycle; Transcription factor activity; Negative regulation of transcription from Pol II promoter; G1 phase of mitotic cell cycle; Transcription corepressor activity; Transcription factor complex; |
| NM_001949 | E2F3 | E2F transcription factor 3 | Regulation of transcription, DNA-dependent; Nucleus; Protein binding; Regulation of cell cycle; Transcription factor activity; Transcription factor complex; Transcription initiation from Pol II promoter; |
| NM_004879 | EI24 | Etoposide induced 2.4 mRNA | Induction of apoptosis; |
| NM_000125 | ESR1 | Estrogen receptor 1 | Signal transduction; DNA binding; Regulation of transcription, DNA-dependent; Nucleus; Transcription factor activity; Receptor activity; Membrane; Steroid hormone receptor activity; Cell growth; Nitric-oxide synthase regulator activity; Steroid binding; Estrogen receptor activity; Estrogen receptor signaling pathway; Negative regulation of mitosis; Chromatin remodeling complex; |
| NM_003824 | FADD | Fas (TNFRSF6)-associated via death domain | Protein binding; Cytoplasm; Regulation of apoptosis; Death receptor binding; Induction of apoptosis via death domain receptors; Signal transducer activity; Cell surface receptor linked signal transduction; Positive regulation of I-kappaB kinase/NF-kappaB cascade; Antimicrobial humoral response (sensu Vertebrata); |
| NM_007051 | FAF1 | Fas (TNFRSF6) associated factor 1 | Nucleus; Molecular_function unknown; Apoptosis; |
| NM_001455 | FOXO3A | Forkhead box O3A | Regulation of transcription, DNA-dependent; Nucleus; Cytoplasm; Cell growth and/or maintenance; Induction of apoptosis; Apoptosis; Transcription factor activity; Transcription from Pol II promoter; |
| NM_004958 | FRAP1 | FK506 binding protein 12-rapamycin associated protein 1 | Transferase activity; Regulation of cell cycle; DNA recombination; DNA repair; Inositol or phosphatidylinositol kinase activity; Phosphoinositide 3-kinase complex; |
| NM_001924 | GADD45A | Growth arrest and DNA-damage-inducible, alpha | Nucleus; Apoptosis; Cell cycle arrest; Regulation of cyclin dependent protein kinase activity; DNA repair; Protein biosynthesis; Structural constituent of ribosome; Ribosome; |
| NM_005255 | GAK | Cyclin G associated kinase | ATP binding; Transferase activity; Protein amino acid phosphorylation; Nucleus; Protein serine/threonine kinase activity; Regulation of cell cycle; Kinase activity; Endoplasmic reticulum; |
| NM_002048 | GAS1 | Growth arrest-specific 1 | Molecular_function unknown; Negative regulation of cell proliferation; Cell cycle arrest; Extrinsic to plasma membrane, GPI-anchored; Negative regulation of S phase of mitotic cell cycle; |

TABLE 1-continued

TP53 Pathway Genes

| GeneBank | Symbol | Description | GO Term |
|---|---|---|---|
| NM_002066 | GML | GPI anchored molecule like protein | Plasma membrane; Apoptosis; Negative regulation of cell proliferation; Regulation of cell cycle; Extrinsic to membrane; DNA damage response, signal transduction by p53 class mediator resulting in cell cycle arrest; |
| NM_016426 | GTSE1 | G-2 and S-phase expressed 1 | Molecular_function unknown; G2 phase of mitotic cell cycle; Microtubule-based process; DNA damage response, signal transduction by p53 class mediator resulting in cell cycle arrest; Cytoplasmic microtubule; |
| NM_004964 | HDAC1 | Histone deacetylase 1 | Hydrolase activity; Regulation of transcription, DNA-dependent; Nucleus; Cytoplasm; Anti-apoptosis; Transcription factor activity; Transcription factor binding; Histone deacetylase activity; Chromatin modification; Histone deacetylation; Histone deacetylase complex; |
| NM_000189 | HK2 | Hexokinase 2 | ATP binding; Transferase activity; Regulation of cell cycle; Mitochondrial outer membrane; Membrane; Glycolysis; Kinase activity; Hexokinase activity; |
| NM_002176 | IFNB1 | Interferon, beta 1, fibroblast | Extracellular; Negative regulation of cell proliferation; Cell surface receptor linked signal transduction; Response to virus; Caspase activation; B-cell proliferation; Defense response; Natural killer cell activation; Positive regulation of innate immune response; Interferon-alpha/beta receptor binding; Anti-inflammatory response; Negative regulation of virion penetration; Regulation of MHC class I biosynthesis; |
| NM_000875 | IGF1R | Insulin-like growth factor 1 receptor | ATP binding; Transferase activity; Protein amino acid phosphorylation; Integral to membrane; Signal transduction; Protein binding; Anti-apoptosis; Regulation of cell cycle; Positive regulation of cell proliferation; Receptor activity; Epidermal growth factor receptor activity; Insulin-like growth factor receptor activity; Insulin receptor signaling pathway; |
| NM_000600 | IL6 | Interleukin 6 (interferon, beta 2) | Humoral immune response; Negative regulation of cell proliferation; Positive regulation of cell proliferation; Cell surface receptor linked signal transduction; Extracellular space; Acute-phase response; Cell-cell signaling; Cytokine activity; Interleukin-6 receptor binding; |
| NM_002228 | JUN | V-jun sarcoma virus 17 oncogene homolog (avian) | Regulation of transcription, DNA-dependent; Cell growth and/or maintenance; Transcription factor activity; RNA polymerase II transcription factor activity; Nuclear chromosome; |
| NM_004985 | KRAS | V-Ki-ras2 Kirsten rat sarcoma viral oncogene homolog | GTP binding; GTPase activity; Small GTPase mediated signal transduction; Cell growth and/or maintenance; Regulation of cell cycle; |
| NM_018494 | LRDD | Leucine-rich repeats and death domain containing | Signal transduction; Protein binding; Death receptor binding; |

TABLE 1-continued

TP53 Pathway Genes

| GeneBank | Symbol | Description | GO Term |
|---|---|---|---|
| NM_021960 | MCL1 | Myeloid cell leukemia sequence 1 (BCL2-related) | Integral to membrane; Protein binding; Cytoplasm; Regulation of apoptosis; Anti-apoptosis; Mitochondrial outer membrane; Apoptotic program; Cell differentiation; Protein channel activity; Protein heterodimerization activity; Cell fate determination; Cell homeostasis; |
| NM_002392 | MDM2 | Mdm2, transformed 3T3 cell double minute 2, p53 binding protein (mouse) | Nucleus; Protein binding; Cell growth and/or maintenance; Protein complex assembly; Negative regulation of cell proliferation; Regulation of cell cycle; Zinc ion binding; Negative regulation of transcription from Pol II promoter; Ligase activity; Ubiquitin-protein ligase activity; Protein ubiquitination; Ubiquitin ligase complex; Negative regulator of basal transcription activity; Regulation of protein catabolism; Nucleolus; Nucleoplasm; |
| NM_002393 | MDM4 | Mdm4, transformed 3T3 cell double minute 4, p53 binding protein (mouse) | Nucleus; Protein binding; Protein complex assembly; Negative regulation of cell proliferation; Zinc ion binding; Negative regulation of transcription from Pol II promoter; Ubiquitin-protein ligase activity; Protein ubiquitination; Ubiquitin ligase complex; Protein stabilization; Negative regulation of protein catabolism; |
| NM_000251 | MSH2 | MutS homolog 2, colon cancer, nonpolyposis type 1 (E. coli) | ATP binding; Nucleus; Negative regulation of cell cycle; Mismatch repair; Damaged DNA binding; Postreplication repair; |
| NM_002467 | MYC | V-myc myelocytomatosis viral oncogene homolog (avian) | Cell proliferation; Nucleus; Transcription factor activity; Regulation of transcription from Pol II promoter; Cell cycle arrest; Iron ion homeostasis; |
| NM_002478 | MYOD1 | Myogenic differentiation 1 | Protein amino acid phosphorylation; DNA binding; RNA polymerase II transcription factor activity, enhancer binding; Regulation of transcription, DNA-dependent; Nucleus; Regulation of transcription from Pol II promoter; Muscle development; Transcription coactivator activity; Cell differentiation; Myogenesis; |
| NM_006096 | NDRG1 | N-myc downstream regulated gene 1 | Nucleus; Cell differentiation; Catalytic activity; Response to metal ion; |
| NM_000267 | NF1 | Neurofibromin 1 (neurofibromatosis, von Recklinghausen disease, Watson disease) | Cytoplasm; Cell growth and/or maintenance; Negative regulation of cell cycle; Negative regulation of cell proliferation; RAS protein signal transduction; Ras GTPase activator activity; Enzyme inhibitor activity; |
| NM_003998 | NFKB1 | Nuclear factor of kappa light polypeptide gene enhancer in B-cells 1 (p105) | Signal transduction; Regulation of transcription, DNA-dependent; Nucleus; Protein binding; Cytoplasm; Apoptosis; Anti-apoptosis; Transcription factor activity; Inflammatory response; Transcription from Pol II promoter; Response to pathogenic bacteria; Antibacterial humoral response (sensu Vertebrata); |
| NM_022112 | P53AIP1 | P53-regulated apoptosis-inducing protein 1 | Molecular_function unknown; Apoptosis; Mitochondrion; |

TABLE 1-continued

TP53 Pathway Genes

| GeneBank | Symbol | Description | GO Term |
|---|---|---|---|
| NM_003884 | PCAF | P300/CBP-associated factor | Transferase activity; Regulation of transcription, DNA-dependent; Nucleus; Negative regulation of cell proliferation; Cell cycle arrest; Cell cycle; Chromatin remodeling; Transcription cofactor activity; N-acetyltransferase activity; Histone acetyltransferase activity; Protein amino acid acetylation; |
| NM_020418 | PCBP4 | Poly(rC) binding protein 4 | Nucleic acid binding; DNA binding; Nucleus; DNA damage response, signal transduction resulting in induction of apoptosis; Cell cycle arrest; RNA binding; Ribonucleoprotein complex; DNA damage response, signal transduction by p53 class mediator resulting in cell cycle arrest; MRNA metabolism; |
| NM_002634 | PHB | Prohibitin | Cell growth and/or maintenance; Negative regulation of cell proliferation; Regulation of cell cycle; Transcriptional activator activity; Nucleoplasm; DNA metabolism; Histone deacetylation; Mitochondrial inner membrane; Transcriptional repressor activity; Negative regulation of transcription; |
| NM_002656 | PLAGL1 | Pleiomorphic adenoma gene-like 1 | Nucleic acid binding; DNA binding; Regulation of transcription, DNA-dependent; Nucleus; Induction of apoptosis; Zinc ion binding; Cell cycle arrest; |
| NM_005030 | PLK1 | Polo-like kinase 1 (*Drosophila*) | ATP binding; Transferase activity; Protein amino acid phosphorylation; Nucleus; Protein serine/threonine kinase activity; Regulation of cell cycle; Mitosis; |
| NM_033238 | PML | Promyelocytic leukemia | Nucleic acid binding; Regulation of transcription, DNA-dependent; Nucleus; Cell growth and/or maintenance; Transcription factor activity; Zinc ion binding; Ubiquitin-protein ligase activity; Protein ubiquitination; Ubiquitin ligase complex; Transcription cofactor activity; |
| NM_000304 | PMP22 | Peripheral myelin protein 22 | Negative regulation of cell proliferation; Membrane fraction; Integral to plasma membrane; Perception of sound; Synaptic transmission; Peripheral nervous system development; Mechanosensory behavior; |
| NM_003620 | PPM1D | Protein phosphatase 1D magnesium-dependent, delta isoform | Hydrolase activity; Nucleus; Negative regulation of cell proliferation; Regulation of cell cycle; Protein amino acid dephosphorylation; Response to radiation; Magnesium ion binding; Manganese ion binding; Protein phosphatase type 2C activity; Protein serine/threonine phosphatase complex; |
| NM_015316 | PPP1R13B | Protein phosphatase 1, regulatory (inhibitor) subunit 13B | |
| NM_032595 | PPP1R9B | Protein phosphatase 1, regulatory subunit 9B, spinophilin | Protein binding; Cytoplasm; Cell cycle arrest; Nucleoplasm; Negative regulation of cell growth; Regulation of cell proliferation; Protein phosphatase inhibitor activity; RNA splicing; Regulation of exit from mitosis; Protein |

TABLE 1-continued

TP53 Pathway Genes

| GeneBank | Symbol | Description | GO Term |
| --- | --- | --- | --- |
| NM_002737 | PRKCA | Protein kinase C, alpha | phosphatase 1 binding; Interpretation of external signals that regulate cell growth; Protein phosphatase type 1 complex; ATP binding; Transferase activity; Protein amino acid phosphorylation; Calcium ion binding; Diacylglycerol binding; Intracellular signaling cascade; Induction of apoptosis by extracellular signals; Regulation of cell cycle; Membrane fraction; Cell surface receptor linked signal transduction; Protein kinase C activity; |
| NM_006257 | PRKCQ | Protein kinase C, theta | ATP binding; Transferase activity; Protein amino acid phosphorylation; Regulation of cell growth; Diacylglycerol binding; Protein serine/threonine kinase activity; Intracellular signaling cascade; Intracellular; |
| NM_000314 | PTEN | Phosphatase and tensin homolog (mutated in multiple advanced cancers 1) | Hydrolase activity; Cell cycle; Protein amino acid dephosphorylation; Protein tyrosine phosphatase activity; Protein tyrosine/serine/threonine phosphatase activity; Phosphatidylinositol-3,4,5-trisphosphate 3-phosphatase activity; Negative regulation of progression through cell cycle; |
| NM_004219 | PTTG1 | Pituitary tumor-transforming 1 | Nucleus; Protein binding; Cytoplasm; Cell growth and/or maintenance; Transcription factor activity; Transcription from Pol II promoter; DNA repair; Spermatogenesis; DNA metabolism; Mitosis; Cysteine protease inhibitor activity; DNA replication and chromosome cycle; Chromosome segregation; |
| NM_013258 | PYCARD | PYD and CARD domain containing | Signal transduction; Protein binding; Cytoplasm; Negative regulation of cell cycle; Induction of apoptosis; Regulation of apoptosis; Caspase activator activity; Caspase activation; |
| NM_006663 | PPP1R13L | Protein phosphatase 1, regulatory (inhibitor) subunit 13 like | Regulation of transcription, DNA-dependent; Nucleus; Apoptosis; |
| NM_000321 | RB1 | Retinoblastoma 1 (including osteosarcoma) | Regulation of transcription, DNA-dependent; Nucleus; Negative regulation of cell cycle; Transcription factor activity; Negative regulation of transcription from Pol II promoter; Chromatin; Cell cycle checkpoint; |
| NM_021975 | RELA | V-rel reticuloendotheliosis viral oncogene homolog A, nuclear factor of kappa light polypeptide gene enhancer in B-cells 3, p65 (avian) | Regulation of transcription, DNA-dependent; Nucleus; Protein binding; Anti-apoptosis; Transcription factor activity; Signal transducer activity; Positive regulation of I-kappaB kinase/NF-kappaB cascade; Transcription from Pol II promoter; Transcription factor complex; Response to toxin; |
| NM_019845 | RPRM | Reprimo, TP53 dependent G2 arrest mediator candidate | Cytoplasm; Cell cycle arrest; |
| NM_052863 | SCGB3A1 | Secretoglobin, family 3A, member 1 | Extracellular; Negative regulation of cell growth; Regulation of cell proliferation; Cytokine activity; |

TABLE 1-continued

TP53 Pathway Genes

| GeneBank | Symbol | Description | GO Term |
| --- | --- | --- | --- |
| NM_014454 | SESN1 | Sestrin 1 | Nucleus; Negative regulation of cell proliferation; Cell cycle arrest; Response to DNA damage stimulus; |
| NM_031459 | SESN2 | Sestrin 2 | Nucleus; Cell cycle arrest; |
| NM_144665 | SESN3 | Sestrin 3 | Nucleus; Cell cycle arrest; |
| NM_006142 | SFN | Stratifin | Cell proliferation; Signal transduction; Cytoplasm; Regulation of cell cycle; Extracellular space; Protein domain specific binding; Protein kinase C inhibitor activity; Negative regulation of protein kinase activity; |
| NM_003029 | SHC1 | SHC (Src homology 2 domain containing) transforming protein 1 | Plasma membrane; Regulation of cell growth; Intracellular signaling cascade; Positive regulation of cell proliferation; Activation of MAPK; Phospholipid binding; Transmembrane receptor protein tyrosine kinase adaptor protein activity; Positive regulation of mitosis; Regulation of epidermal growth factor receptor activity; |
| NM_003031 | SIAH1 | Seven in absentia homolog 1 (*Drosophila*) | Nucleus; Apoptosis; Zinc ion binding; Ligase activity; Development; Cell cycle; Spermatogenesis; Ubiquitin-dependent protein catabolism; Ubiquitin cycle; |
| NM_012238 | SIRT1 | Sirtuin (silent mating type information regulation 2 homolog) 1 (*S. cerevisiae*) | Hydrolase activity; DNA binding; Regulation of transcription, DNA-dependent; Nucleus; Apoptosis; Myogenesis; Chromatin silencing; Chromatin silencing complex; |
| NM_003073 | SMARCB1 | SWI/SNF related, matrix associated, actin dependent regulator of chromatin, subfamily b, member 1 | Negative regulation of cell cycle; Regulation of transcription from Pol II promoter; Nuclear chromosome; Nucleoplasm; Chromatin remodeling; DNA integration; |
| NM_000345 | SNCA | Synuclein, alpha (non A4 component of amyloid precursor) | Cytoplasm; Anti-apoptosis; Central nervous system development; |
| NM_007315 | STAT1 | Signal transducer and activator of transcription 1, 91 kDa | Regulation of transcription, DNA-dependent; Nucleus; Cytoplasm; Intracellular signaling cascade; Regulation of cell cycle; Transcription factor activity; Signal transducer activity; Transcription from Pol II promoter; Caspase activation; STAT protein nuclear translocation; Tyrosine phosphorylation of STAT protein; Hematopoietin/interferon-class (D200-domain) cytokine receptor signal transducer activity; I-kappaB kinase/NF-kappaB cascade; Response to pest, pathogen or parasite; |
| NM_006354 | TADA3L | Transcriptional adaptor 3 (NGG1 homolog, yeast)-like | Nucleus; Regulation of cell cycle; Transcription factor activity; Regulation of transcription from Pol II promoter; |
| NM_000594 | TNF | Tumor necrosis factor (TNF superfamily, member 2) | Integral to membrane; Signal transduction; Immune response; Regulation of transcription, DNA-dependent; Apoptosis; Anti-apoptosis; Inflammatory response; Response to virus; Soluble fraction; Cell-cell signaling; Tumor necrosis factor receptor binding; Leukocyte cell adhesion; Necrosis; |

TABLE 1-continued

TP53 Pathway Genes

| GeneBank | Symbol | Description | GO Term |
|---|---|---|---|
| NM_003842 | TNFRSF10B | Tumor necrosis factor receptor superfamily, member 10b | Integral to membrane; Signal transduction; Protein binding; Electron transporter activity; Induction of apoptosis; Regulation of apoptosis; Induction of apoptosis via death domain receptors; Positive regulation of I-kappaB kinase/NF-kappaB cascade; Receptor activity; Iron ion binding; Electron transport; TRAIL binding; Caspase activator activity; Caspase activation; Activation of NF-kappaB-inducing kinase; |
| NM_000639 | FASLG | Fas ligand (TNF superfamily, member 6) | Signal transduction; Extracellular; Immune response; Induction of apoptosis; Apoptosis; Positive regulation of I-kappaB kinase/NF-kappaB cascade; Integral to plasma membrane; Cell-cell signaling; Tumor necrosis factor receptor binding; |
| NM_000546 | TP53 | Tumor protein p53 (Li-Fraumeni syndrome) | ATP binding; Cell proliferation; Regulation of transcription, DNA-dependent; Protein binding; Negative regulation of cell cycle; Apoptosis; Mitochondrion; Transcription factor activity; Zinc ion binding; DNA damage response, signal transduction resulting in induction of apoptosis; Cell cycle arrest; Nucleolus; Cell cycle checkpoint; DNA strand annealing activity; Copper ion binding; Nuclease activity; DNA recombination; Base-excision repair; Caspase activation via cytochrome c; Cell aging; Cell differentiation; Induction of apoptosis by hormones; Negative regulation of cell growth; Nucleotide-excision repair; Regulation of mitochondrial membrane permeability; Protein tetramerization activity; Negative regulation of helicase activity; |
| NM_005426 | TP53BP2 | Tumor protein p53 binding protein, 2 | Signal transduction; Cytoplasm; Apoptosis; Regulation of cell cycle; SH3/SH2 adaptor protein activity; |
| NM_005427 | TP73 | Tumor protein p73 | Regulation of transcription, DNA-dependent; Nucleus; Protein binding; Negative regulation of cell cycle; Apoptosis; Transcription factor activity; DNA damage response, signal transduction resulting in induction of apoptosis; Mismatch repair; |
| NM_003722 | TP73L | Tumor protein p73-like | Regulation of transcription, DNA-dependent; Nucleus; Induction of apoptosis; Apoptosis; Transcription factor activity; Transcriptional activator activity; |
| NM_021138 | TRAF2 | TNF receptor-associated factor 2 | Signal transduction; Protein complex assembly; Apoptosis; Zinc ion binding; Signal transducer activity; Ubiquitin-protein ligase activity; Protein ubiquitination; Ubiquitin ligase complex; |
| NM_004295 | TRAF4 | TNF receptor-associated factor 4 | Nucleus; Apoptosis; Zinc ion binding; Ubiquitin-protein ligase activity; Protein ubiquitination; Ubiquitin ligase complex; Development; |

TABLE 1-continued

TP53 Pathway Genes

| GeneBank | Symbol | Description | GO Term |
| --- | --- | --- | --- |
| NM_004619 | TRAF5 | TNF receptor-associated factor 5 | Signal transduction; Apoptosis; Zinc ion binding; Signal transducer activity; Ubiquitin-protein ligase activity; Protein ubiquitination; Ubiquitin ligase complex; Positive regulation of I-kappaB kinase/NF-kappaB cascade; |
| NM_000368 | TSC1 | Tuberous sclerosis 1 | Cell adhesion; Rho protein signal transduction; Negative regulation of cell cycle; |
| NM_000548 | TSC2 | Tuberous sclerosis 2 | Plasma membrane; GTPase activator activity; Cell growth and/or maintenance; Negative regulation of cell cycle; Cytosol; Membrane fraction; Protein folding; Endocytosis; Unfolded protein binding; |
| NM_000369 | TSHR | Thyroid stimulating hormone receptor | Positive regulation of cell proliferation; Signal transducer activity; Integral to plasma membrane; Cell-cell signaling; G-protein signaling, coupled to cyclic nucleotide second messenger; Heterotrimeric G-protein complex; Thyroid-stimulating hormone receptor activity; |
| NM_000378 | WT1 | Wilms tumor 1 | Nucleic acid binding; Regulation of transcription, DNA-dependent; Nucleus; Negative regulation of cell cycle; Transcription factor activity; Zinc ion binding; |
| NM_002046 | GAPDH | Glyceraldehyde-3-phosphate dehydrogenase | Cytoplasm; Oxidoreductase activity; Glyceraldehyde-3-phosphate dehydrogenase (phosphorylating) activity; Glucose metabolism; Glycolysis; |
| NM_004048 | B2M | Beta-2-microglobulin | Extracellular; Immune response; |
| NM_007355 | HSP90AB1 | Heat shock protein 90 kDa alpha (cytosolic), class B member 1 | ATP binding; Protein binding; Cytoplasm; Heat shock protein activity; Protein folding; TPR domain binding; Nitric-oxide synthase regulator activity; Positive regulation of nitric oxide biosynthesis; Unfolded protein binding; Response to unfolded protein; ATP binding; Protein binding; Cytoplasm; Heat shock protein activity; Protein folding; TPR domain binding; Nitric-oxide synthase regulator activity; Positive regulation of nitric oxide biosynthesis; Unfolded protein binding; Response to unfolded protein; |
| NM_007355 | HSP90AB1 | Heat shock protein 90 kDa alpha (cytosolic), class B member 1 | ATP binding; Protein binding; Cytoplasm; Heat shock protein activity; Protein folding; TPR domain binding; Nitric-oxide synthase regulator activity; Positive regulation of nitric oxide biosynthesis; Unfolded protein binding; Response to unfolded protein; ATP binding; Protein binding; Cytoplasm; Heat shock protein activity; Protein folding; TPR domain binding; Nitric-oxide synthase regulator activity; Positive regulation of nitric oxide biosynthesis; Unfolded protein binding; Response to unfolded protein; |

II. Aspects and Embodiments of the Invention

In accordance with the foregoing, in one aspect, the present invention provides a method for identifying or evaluating an agent that is predicted to modify or modulate TP53 activity or TP53 pathway activity in a subject. This aspect of the invention is useful in identifying or evaluating whether an agent affects TP53 activity and/or TP53 pathway activity. The TP53 pathway includes proteins that function both upstream and downstream of TP53, including, for example, proteins that are involved in the signal transduction pathway from perception of DNA damage, to modulation of TP53 activity, through to cell cycle arrest and/or apoptosis. Agents affecting TP53 pathway activity include small molecule compounds, protein, or peptides (including antibodies) siRNA, shRNA or microRNA molecules, or any other agents that modulate one or more genes or proteins that function within the TP53 pathway or in other cell cycle regulatory pathways that interact with the TP53 pathway, such as, for example, the AKT/Chek1 pathway.

In one embodiment, the method comprises contacting an agent with a first population of cells from a subject; measuring the amount or level of miR-34 present in the first population of cells; measuring the amount or level of miR-34 present in a second population of cells that are not contacted with the agent; and comparing said measured amount of miR-34 in the first population of cells to the measured amount of miR-34 in the second population of cells, wherein a difference in the measured amounts of miR-34s in the first population of cells compared to the second population of cells indicates that the agent modifies TP53 pathway activity in said subject.

In one embodiment, the one or more miR-34 members are selected from the group consisting of miR-34a (SEQ ID NO:1), miR-34b (SEQ ID NO:4), miR-34c (SEQ ID NO:7), and precursor RNAs thereof, (SEQ ID NO:2; SEQ ID NO:5 and SEQ ID NO:8). The amount of miR-34 present in a population of cells can be measured using methods such as nucleic acid hybridization (Lu et al. (2005)*Nature* 435:834-838), quantitative polymerase chain reaction (Raymond et al. (2006)*RNA* 11:1737-1744), or any other method that is capable of providing a measured level (either as a quantitative amount or as an amount relative to a standard or control amount, i.e., a ration or a fold-change) of a micro-RNA within a cell sample.

In one embodiment of the invention, the agent is evaluated using a cell sample treated with multiple different concentrations to determine if the agent modulates TP53 activity or TP53 pathway activity. In other embodiments, a time course of exposure to the agent is evaluated.

In another embodiment, the determination of a difference in the measured level of one or more miR-34 members is evaluated using one or more statistical tests known in the art. Based upon the outcome of the one or more statistical tests, an agent may be classified as modulating the activity of TP53 or TP53 pathway in a statistically significant fashion. Agents that are intended to increase or decrease the level of TP53 or TP53 pathway activity can be evaluated using one or more embodiments of the invention.

In other embodiments, the one or more statistical tests can be used to evaluate the degree or magnitude to which the agent modulates TP53 pathway activity. In one embodiment, a statistical significance change of 1.5- to 2-fold in the measured level of one or more miR-34 levels indicates that the agent, at that particular concentration, has a low level of effect on TP53 activity or TP53 pathway activity. In another embodiment, a statistical significance change of 3- to 5-fold in the measured level of one or more miR-34 levels indicates that the agent, at that particular concentration, has a medium level of effect on TP53 activity or TP53 pathway activity. In yet another embodiment, a statistical significance change of 5-fold or greater in the measured level of one or more miR-34 levels indicates that the agent, at that particular concentration, has a high level of effect on TP53 activity or TP53 pathway activity. In one embodiment, multiple different agents are rank ordered based on the measured level of one or more miR-34, in another embodiment, the agents are rank ordered based upon fold change in the measured level of one or more miR-34.

In one embodiment, the method is used to determine whether a subject has received an effective dose of an agent sufficient to modulate TP53 pathway activity. An effective dose is an amount of agent sufficient to cause a therapeutically desired shift in TP53 pathway activity with respect to either the direction of change in TP53 pathway activity (i.e., decreased activity or increased activity) or the magnitude of change in the TP53 pathway activity (i.e., 2-fold, 5-fold, or 10-fold). In one embodiment of the invention, the agents are cancer therapeutic agents, such as chemotherapeutic agents or agents meant to increase the effectiveness of chemotherapeutic agents. In one embodiment, the agents target, i.e., modulate the activity of, one or more proteins or activities of the TP53 pathway.

In a second aspect, the present invention provides a method of estimating TP53 pathway activity or status in a cell sample from a subject comprising: obtaining a measured level of one or more members of miR-34 present in a cell sample from a subject; comparing the obtained level of one or more members of miR-34 with a baseline level of one or more members of miR-34, the baseline level of the one or more members of miR-34 being correlated with a TP53 pathway activity status; wherein an increase or decrease in the level of the one or more members of miR-34 in said cell sample compared to said baseline level estimates the TP53 pathway status of said cell sample.

In one embodiment of this aspect of the invention, the miR-34 member is selected from the group consisting of miR-34a (SEQ ID NO:1), miR-34b (SEQ ID NO:4), miR-34c (SEQ ID NO:7), and precursor RNAs thereof (SEQ ID NO:2; SEQ ID NO:5 and SEQ ID NO:8).

A baseline level of miR-34 can be established by reference to a specific cell line wherein the cell line is known to have functional TP53 activity or defective TP53 activity. Examples of cell lines having functional TP53, include, but are not limited to, HCT116 (Vassilev et al., 2004, *Science*, 303:844-8), LOVO (Cottu et al., 1995, *Cancer Res*, 13:2727-30), LS123 (Liu and Bodmer, 2006, *PNAS*, 103:976-81), RKO (Vassilev et al., 2004, *Science*, 303:844-8) and RKO-AS45-1 (Bamford, et al., 2004, *Br. J. Cancer* 91:355-58). Examples of cell lines having defective TP53 include, but are not limited to, HT29 (Rodrigues et al., 1990, *PNAS*, 87:7555-9), LS1034 (Liu and Bodmer, 2006, *PNAS*, 103:976-81), SW1417 (Liu and Bodmer, 2006, *PNAS*, 103:976-81), SW1116 (Liu and Bodmer, 2006, *PNAS*, 103:976-81), and SW620 (Rodrigues et al., 1990, *PNAS*, 87:7555-9). Alternatively, matched cell line pairs with and without functional TP53, such as those described in Example 1 herein, can be transfected with a nucleic acid vector encoding a shRNA hairpin molecule targeting TP53 for gene silencing.

In other embodiments, multiple different cell samples can be pooled together and the resulting pool used to set the baseline level of miR-34, or alternatively, the baseline level can be obtained using individual miR-34 measurements from a plurality of different cell samples using any of a variety of different statistical tests that are known in the art. In still other embodiments, the baseline level of miR-34 is established based upon the level of one or more miR-34 members measured in one or more cell or tissue samples of the subject or species of the subject.

Baseline levels of the one or more members of miR-34 are correlated with a TP53 pathway activity status when the obtained level of miR-34 is related in a statistically significant fashion to the functional activity of TP53 or the functional activity of the TP53 pathway.

In other embodiments, the p53 pathway status of a cell sample obtained from a tumor sample is used to determine a course of treatment for a patient having cancer. For example, patients having tumors that are classified as having a substantially active TP53 pathway status are treated with a therapeutically sufficient amount of a composition comprising one or more DNA damaging agents. The one or more DNA damaging agents can comprise a topoisomerase I inhibitor, e.g., camptothecin; a topoisomerase II inhibitor, e.g., doxorubicin; a DNA binding agent, e.g., cisplatin; an anti-metabolite; or ionizing radiation.

In another embodiment, patients having tumors that are classified as having substantially inactive TP53 pathway status are treated with a therapeutically sufficient amount of a composition comprising one or more DNA damaging agents in combination with an inhibitor of a protein or gene capable of enhancing cell killing by the one or more DNA damaging agents. Genes and proteins whose activity affects, either positively or negatively, the sensitivity of TP53 pathway inactive cells to DNA damaging agents are described in PCT Publication WO 2005/031002.

One embodiment of therapeutic treatment involves use of a therapeutically sufficient amount of a composition comprising a miR-34 family member selected from miR-34a, miR-34b, miR-34c or miR-449 siRNA or shRNA to treat tumors classified as containing functional TP53. Such treatment may be in combination with one or more DNA damaging agents.

Therapeutic miR-34a, miR-34b, miR-34c, or miR-449, siRNA or shRNA compositions comprise a guide strand contiguous nucleotide sequence of at least 18 nucleotides, wherein said guide strand comprises a seed region consisting of nucleotide positions 1 to 12, wherein position 1 represents the 5' end of said guide strand and wherein said seed region comprises a nucleotide sequence of at least six contiguous nucleotides that is identical to six contiguous nucleotides within a sequence selected from the group consisting of SEQ ID NO:3, SEQ ID NO:6, SEQ ID NO:9 and SEQ ID NO:31. In certain embodiments, at least one of the two strands further comprises a 1-4, preferably a 2 nucleotide, 3' overhang. The nucleotide overhang can include any combination of a thymine, uracil, adenine, guanine, or cytosine, or derivatives or analogues thereof. The nucleotide overhang in certain aspects is a 2 nucleotide overhang, where both nucleotides are thymine. Importantly, when the dsRNA comprising the sense and antisense strands is administered, it directs target specific interference and bypasses an interferon response pathway.

In order to enhance the stability of the short interfering nucleic acids, the 3' overhangs can also be stabilized against degradation. In one embodiment, the 3' overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

As used herein, a "3' overhang" refers to at least one unpaired nucleotide extending from the 3' end of an siRNA sequence. The 3' overhang can include ribonucleotides or deoxyribonucleotides or modified ribonucleotides or modified deoxyribonucleotides. The 3' overhang is preferably from 1 to about 5 nucleotides in length, more preferably from 1 to about 4 nucleotides in length and most preferably from about 2 to about 4 nucleotides in length. The 3' overhang can occur on the sense or antisense sequence, or on both sequences, of an RNAi construct. The length of the overhangs can be the same or different for each strand of the duplex. Most preferably, a 3' overhang is present on both strands of the duplex, and the overhang for each strand is 2 nucleotides in length. For example, each strand of the duplex can comprise 3' overhangs of dithymidylic acid ("tt") or diuridylic acid ("uu").

Another aspect of the invention provides chemically modified siRNA constructs. For example, the siRNA agent can include a non-nucleotide moiety. A chemical modification or other non-nucleotide moiety can stabilize the sense (guide strand) and antisense (passenger strand) sequences against nucleolytic degradation. Additionally, conjugates can be used to increase uptake and target uptake of the siRNA agent to particular cell types. Thus, in one embodiment, the siRNA agent includes a duplex molecule wherein one or more sequences of the duplex molecule is chemically modified. Non-limiting examples of such chemical modifications include phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5'-C-methyl nucleotides, and terminal glyceryl and/or inverted deoxy abasic residue incorporation. These chemical modifications, when used in siRNA agents, can help to preserve RNAi activity of the agents in cells and can increase the serum stability of the siRNA agents.

In one embodiment, the first, and optionally or preferably the first two, internucleotide linkages at the 5' end of the antisense and/or sense sequences are modified, preferably by a phosphorothioate. In another embodiment, the first, and perhaps the first two, three, or four, internucleotide linkages at the 3' end of a sense and/or antisense sequence are modified, for example, by a phosphorothioate. In another embodiment, the 5' end of both the sense and antisense sequences, and the 3' end of both the sense and antisense sequences are modified as described.

In some embodiments of the invention, TP53 pathway status relates to determining degree to which the TP53 pathway is active or inactive within a cell or population of cells. For example, one measure of whether a cell has an active TP53 pathway is that activation of TP53 by ultraviolet or ionizing radiation, or other DNA-damaging agents, such as chemotherapeutic agents, results in some degree of cell cycle arrest and/or apoptosis. Cells having an impaired or inactive TP53 pathway status are unable to arrest cell division or initiate apoptosis following cellular stress compared to cells having a functional or active TP53 pathway. TP53 pathway status may also be characterized by measuring a defect or change in expression of one or more genes or proteins that are members of the TP53 pathway, such as those set forth in Table 1 above. In some embodiments of the invention, TP53 pathway status may be classified into two status categories, such as, for example, substantially functional (i.e., able to elicit TP53-mediated cell cycle arrest in the presence of genotoxic stress or able to activate a TP53-responsive reporter system (e.g., p53RE-bla; Catalog No. K1193 (Invitrogen Corporation, Carlsbad, Calif.)) and substantially nonfunctional (e.g., unable to elicit TP53-mediated cell cycle arrest in the presence of genotoxic stress or unable to activate a TP53-responsive reporter system), based upon measurement of one or more miR-34 levels in a cell sample.

Alternatively, TP53 functional status may be classified into three or more functional categories, such as for example, high TP53 pathway activity, medium TP53 pathway activity, or low TP53 pathway activity, based upon the level of miR-34 measured in a cell. Threshold levels for each such TP53 pathway status category can be set by measuring or obtaining a range of miR-34 levels from a plurality of different cell types or cell samples whose TP53 pathway function has been determined or evaluated based on functional biological measurement of TP53 pathway function.

In one embodiment of this aspect of the invention, the miR-34 molecule level that is measured or obtained is selected from the group consisting of miR-34a (SEQ ID NO:1), miR-34b (SEQ ID NO:4), miR-34c (SEQ ID NO:7), and precursor RNAs thereof (SEQ ID NO:2; SEQ ID NO:5 and SEQ ID NO:8, respectively).

Another aspect of the invention provides a method of inhibiting cell division of a mammalian cell comprising introducing into said cell an effective amount of a small interfering nucleic acid (siNA), wherein said siNA comprises a guide strand contiguous nucleotide sequence of at least 18 nucleotides, wherein said guide strand comprises a seed region consisting of nucleotide positions 1 to 12, wherein position 1 represents the 5' end of said guide strand and wherein said seed region comprises a nucleotide sequence of at least six contiguous nucleotides that is identical to six contiguous nucleotides within a sequence selected from the group consisting of SEQ ID NO:3, SEQ ID NO:6, SEQ ID NO:9 and SEQ ID NO:31.

In one embodiment, the siNA is a duplex RNA molecule that is introduced into said cell by transfection. In some embodiments, the introduced siNA includes one or more chemically modified nucleotides. An effective amount of siNA is the amount sufficient to cause a measurable change in the detected level of one or more gene transcripts that are regulated by one or more members of the miR-34 family. In one embodiment, the gene transcripts regulated by one or more members of the miR-34 family are selected from Table 9.

In another embodiment, cell division is inhibited by introduction of a nucleic acid vector molecule expressing an shRNA gene, wherein the shRNA transcription product acts as an RNAi agent. The shRNA gene may encode a microRNA precursor RNA, such as, for example, SEQ ID NO:2, SEQ ID NO:5, SEQ ID NO:8, or SEQ ID NO:30. Alternatively, the shRNA gene may encode any other RNA sequence that is susceptible to processing by endogenous cellular RNA processing enzymes into an active siRNA sequence, wherein the seed region of the active siRNA sequence contains at least a six contiguous nucleotide sequence that is identical to a six contiguous nucleotide sequence within SEQ ID NO:3, SEQ ID NO:6, SEQ ID NO:9, or SEQ ID NO:31. Examples of vectors and transcription promoter sequences useful for expression of shRNA genes are well known in the art (Paddison, et al., 2004, *Nature* 4: 28-31; Silva et al., 2005, *Nat. Genet.* 37:1281-88; Bernards et al., 2006, *Nat. Methods* 3:701-06). An effective amount of shRNA is the amount sufficient to cause a measurable change in the detected level of one or more gene transcripts that are regulated by one or more members of the miR-34 family. In one embodiment, the gene transcripts regulated by one or more members of the miR-34 family are selected from Table 9.

In another aspect, the invention provides an isolated nucleic acid molecule comprising, or consisting essentially of, a guide strand nucleotide sequence of 18 to 25 nucleotides, said guide strand nucleotide sequence comprising a seed region nucleotide sequence and a non-seed region nucleotide sequence, said seed region consisting essentially of nucleotide positions 1 to 12 and said non-seed region consisting essentially of nucleotide positions 13 to the 3' end of said guide strand, wherein position 1 of said guide strand represents the 5' end of said guide strand, wherein said seed region further comprises a consecutive nucleotide sequence of at least 6 nucleotides that is identical in sequence to a nucleotide sequence selected from the group consisting of SEQ ID NO:3, SEQ ID NO:6, SEQ ID NO:9, and SEQ ID NO:31 and wherein said isolated nucleic acid molecule has at least one nucleotide sequence difference, compared to a nucleotide sequence selected from the group consisting of SEQ ID NO:1, SEQ ID NO:2, and SEQ ID NO:3.

In one embodiment, the isolated nucleic acid molecule consists essentially of a guide strand nucleotide sequence of 19 to 23 nucleotides, said guide strand nucleotide sequence comprising a seed region nucleotide sequence and a non-seed region nucleotide sequence, said seed region consisting essentially of nucleotide positions 1 to 10 and said non-seed region consisting essentially of nucleotide positions 11 to the 3' end of said guide strand, wherein position 1 of said guide strand represents the 5' end of said guide strand, wherein said seed region further comprises a consecutive nucleotide sequence of at least 6 nucleotides that is identical in sequence to a nucleotide sequence selected from the group consisting of SEQ ID NO:3, SEQ ID NO:6, SEQ ID NO:9, and SEQ ID NO:31, and wherein said isolated nucleic acid molecule has at least one nucleotide sequence difference, compared to a nucleotide sequence selected from the group consisting of SEQ ID NO:1, SEQ ID NO:2, and SEQ ID NO:3.

In another embodiment, the invention provides isolated synthetic duplex microRNA mimetics for use in the methods of the invention. As described herein, it has been demonstrated that a synthetic duplex microRNA mimetic comprising a guide strand with the sequence corresponding to natural mature miR34a (SEQ ID NO:1), and a synthetic passenger strand (SEQ ID NO:12) that is essentially complementary to the miR34a natural mature guide strand, except for a single base mismatch located in the 3' end of the sequence (assymetric passenger strand) was more effective at inducing a cell cycle phenotype when transfected into cells, than a duplex consisting of the natural miR-34a guide strand (SEQ ID NO:1) and the natural miR-34a passenger strand (SEQ ID NO: 35), as demonstrated in Example 10. While not wishing to be bound by theory, it is believed that the presence of a mismatch in the passenger strand may facilitate entry into RISC.

Accordingly, in one embodiment, the invention provides an isolated synthetic duplex microRNA mimetic comprising (i) a guide strand nucleic acid molecule consisting of a nucleotide sequence of 18 to 25 nucleotides, said guide strand nucleotide sequence comprising a seed region nucleotide sequence and a non-seed region nucleotide sequence, said seed region consisting of nucleotide positions 1 to 12 and said non-seed region consisting of nucleotide positions 13 to the 3' end of said guide strand, wherein position 1 of said guide strand represents the 5' end of said guide strand, wherein said seed region further comprises a consecutive nucleotide sequence of at least 6 nucleotides that is identical to a seed region sequence of a naturally occurring microRNA; and (ii) a passenger strand nucleic acid molecule consisting of a nucleotide sequence of 18 to 25 nucleotides, said passenger strand comprising a nucleotide sequence that is essentially complementary to the guide strand, wherein said passenger strand nucleic acid molecule has one nucleotide sequence difference compared with the true reverse complement sequence of the seed region of the guide strand, wherein the one nucleotide difference is located within nucleotide position 13 to the 3' end of the passenger strand. The synthetic duplex microRNA mimetics of this aspect of the invention may be included in compositions with a delivery agent, such as lipid nanoparticles, as described herein.

In one embodiment, the guide strand comprises a seed region comprising a consecutive nucleotide sequence of at least 6 nucleotides that is identical in sequence to a nucleotide sequence selected from the group consisting of SEQ ID NO: 3, SEQ ID NO:6, SEQ ID NO:9 and SEQ ID NO:31. In one embodiment, the guide strand sequence is selected from the group consisting of SEQ ID NO:1, SEQ ID NO:4, SEQ ID NO:7 and SEQ ID NO:29.

In accordance with this aspect of the invention, the passenger strand is a nucleic acid molecule consisting of a nucleotide sequence of 18 to 25 nucleotides. The nucleotide sequence of the passenger strand is essentially complementary to the guide strand, wherein the passenger strand has one nucleotide sequence difference as compared with the true reverse complement sequence of the seed region of the guide strand. As used herein, the term "essentially complementary" with reference to guide strand refers to passenger strands that are the reverse complement of a guide strand with a one base mismatch (nucleotide sequence difference) with the guide strand seed sequence (positions 1 to 12 of the guide strand), which is located at the 3' end of the passenger strand (from position 13 to the 3' end). In some embodiments, the mismatch is located within 6 nucleotides of the 3' end of the passenger strand. In one embodiment, the mismatch is located 6 nucleotides from the 3' end of the passenger strand. In one embodiment, the mismatch is located 5 nucleotides from the 3' end of the passenger strand. In one embodiment, the mismatch is located 4 nucleotides from the 3' end of the passenger strand. In one embodiment, the mismatch is located 3 nucleotides from the 3' end of the passenger strand. In one embodiment, the mismatch is located 2 nucleotides from the 3' end of the passenger strand.

In some embodiments, the nucleotide sequence of the passenger strand is essentially complementary to the reverse complement of the sequence of the guide strand, wherein the 5' end of the passenger strand is complementary to a position 1 to 4 bases from the 3' end of the guide strand, thereby forming a 3' overhang on one end of the duplex when the guide strand and passenger strand are annealed together.

In some embodiments, the nucleotide sequence is essentially complementary to the reverse complement of the sequence of the guide strand, wherein the 3' end of the passenger strand extends from 1 to 4 bases beyond the 5' end of the guide strand, thereby forming a 3' overhang on one end of the duplex when the guide strand and passenger strand are annealed together.

In one embodiment, the isolated synthetic duplex comprises guide strand SEQ ID NO:1 and passenger strand SEQ ID NO: 12. In one embodiment, the isolated synthetic duplex comprises guide strand SEQ ID NO:4 and passenger strand SEQ ID NO:17. In one embodiment, the isolated synthetic duplex comprises guide strand SEQ ID NO:7 and passenger strand SEQ ID NO:22. In one embodiment, the isolated synthetic duplex comprises guide strand SEQ ID NO:29 and passenger strand SEQ ID NO: 32.

III. Nucleic Acid Molecules

As used herein a "nucleobase" refers to a heterocyclic base, such as, for example, a naturally occurring nucleobase (i.e., an A, T, G, C, or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for a naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenine, a 8-bromoadenine, a 8-hydroxyadenine, a 6-hydroxyaminopurine, a 6-thiopurine, a 4-(6-aminohexyl/cytosine), and the like. A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including, but not limited to, a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992, "DNA replication," Freeman and Company, New York, N.Y.).

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. Other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, "Nucleotide Analogs: Synthesis and Biological Function," Wiley, N.Y.).

Additional non-limiting examples of nucleosides, nucleotides, or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652, 099 and 5,763,167, which describe nucleic acids incorporating fluorescent analogs of nucleosides found in DNA or RNA, particularly for use as fluorescent nucleic acid probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446, 137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466, 786 and 5,792,847, which describe the linkage of a substituent moiety, which may comprise a drug or label, to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of an adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probes; U.S. Pat. Nos. 5,378,825, 5,777, 092, 5,623,070, 5,610,289 and 5,602,240, which describe oligonucleotides with a three or four atom linker moiety replacing phosphodiester backbone moiety used for improved nuclease resistance, cellular uptake and regulating RNA expression; U.S. Pat. No. 5,858,988, which describes a hydrophobic carrier agent attached to the 2'-O position of oligonucleotides to enhance their membrane permeability and stability; U.S. Pat. No. 5,214,136, which describes oligonucleotides conjugated to anthraquinone at the 5' terminus that possesses enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; and U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; and U.S. Pat. Nos. 5,637,683, 6,251,666 (L-nucleotide substitutions), and 5,480,980 (7-deaza-2' deoxyguanosine nucleotides and nucleic acid analogs thereof).

shRNA Mediated Suppression

Alternatively, certain of the nucleic acid molecules of the instant invention can be expressed within cells from eukaryotic promoters (e.g., Izant and Weintraub, 1985, *Science*, 229:345; McGarry and Lindquist, 1986, *Proc. Natl. Acad. Sci., USA* 83:399; Scanlon et al., 1991, *Proc. Natl. Acad. Sci. USA*, 88:10591-95; Kashani-Sabet et al., 1992, *Antisense Res. Dev.*, 2:3-15; Dropulic et al., 1992, *J. Virol.*, 66:1432-41; Weerasinghe et al., 1991, *J. Virol.*, 65:5531-4; Ojwang et al., 1992, *Proc. Natl. Acad. Sci. USA*, 89:10802-06; Chen et al., 1992, *Nucleic Acids Res.*, 20:4581 89; Sarver et al., 1990 *Science*, 247:1222-25; Thompson et al., 1995, *Nucleic Acids Res.*, 23:2259; Good et al., 1997, *Gene Therapy*, 4:45). Those skilled in the art realize that any nucleic acid can be expressed in eukaryotic cells from the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595; Ohkawa et al., 1992, *Nucleic Acids. Symp. Ser.*, 27:15-6; Taira et al., 1991, *Nucleic Acids Res.*, 19:5125-30; Ventura et al., 1993, *Nucleic Acids Res.*, 21:3249-55; Chowrira et al., 1994, *J. Biol. Chem.*, 269:25856). Gene therapy approaches specific to the CNS are described by Blesch et al., 2000, *Drug News Perspect.*, 13:269-280; Peterson et al., 2000, *Cent. Nerv. Syst. Dis.*, 485:508; Peel and Klein, 2000, *J. Neurosci. Methods*, 98:95-104; Hagihara et al., 2000, *Gene Ther.*, 7:759-763; and Herrlinger et al., 2000, *Methods Mol. Med.*, 35:287-312. AAV-mediated delivery of nucleic acid to cells of the nervous system is further described by Kaplitt et al., U.S. Pat. No. 6,180,613.

In another aspect of the invention, RNA molecules of the present invention are preferably expressed from transcription units (see for example Couture et al., 1996, TIG., 12:510) inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the nucleic acid molecules are delivered as described above, and persist in target cells. Alternatively, viral vectors can be used that provide for transient expression of nucleic acid molecules. Such vectors can be repeatedly administered as necessary. Once expressed, the nucleic acid molecule binds to the target mRNA. Delivery of nucleic acid molecule expressing vectors can be systemic, such as by intravenous or intramuscular administration, by administration to target cells ex-planted from the patient or subject followed by reintroduction into the patient or subject, or by any other means that would allow for introduction into the desired target cell (for a review see Couture et al., 1996, *TIG.*, 12:510).

In one aspect, the invention features an expression vector comprising a nucleic acid sequence encoding at least one of the nucleic acid molecules of the instant invention. The nucleic acid sequence encoding the nucleic acid molecule of the instant invention is operably linked in a manner which allows expression of that nucleic acid molecule.

In another aspect, the invention features an expression vector comprising: a) a transcription initiation region (e.g., eukaryotic pol I, II, or III initiation region); b) a transcription termination region (e.g., eukaryotic pol I, II, or III termination region); c) a nucleic acid sequence encoding at least one of the nucleic acid molecules of the instant invention; and wherein said sequence is operably linked to said initiation region and said termination region, in a manner which allows expression and/or delivery of said nucleic acid molecule. The vector can optionally include an open reading frame (ORF) for a protein operably linked on the 5' side or the 3'-side of the sequence encoding the nucleic acid molecule of the invention; and/or an intron (intervening sequences).

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA,* 87:6743-7; Gao and Huang, 1993, *Nucleic Acids Res.,* 21:2867-72; Lieber et al., 1993, *Methods Enzymol.,* 217:47-66; Zhou et al., 1990, *Mol. Cell. Biol.,* 10:4529-37).

Several investigators have demonstrated that nucleic acid molecules encoding shRNAs or microRNAs expressed from such promoters can function in mammalian cells (Brummelkamp et al., 2002, *Science* 296:550-553; Paddison et al., 2004, *Nat. Methods* 1:163-67; McIntyre and Fanning 2006 *BMC Biotechnology* (January 5) 6:1; Taxman et al., 2006 *BMC Biotechnology* (January 24) 6:7). The above shRNA or microRNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another aspect the invention features an expression vector comprising nucleic acid sequence encoding at least one of the nucleic acid molecules of the invention, in a manner which allows expression of that nucleic acid molecule. The expression vector comprises in one embodiment: a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

In another embodiment, the expression vector comprises: a) a transcription initiation region; b) a transcription termination region; c) an open reading frame; d) a nucleic acid sequence encoding at least one said nucleic acid molecule, wherein said sequence is operably linked to the 3'-end of said open reading frame; and wherein said sequence is operably linked to said initiation region, said open reading frame, and said termination region, in a manner which allows expression and/or delivery of said nucleic acid molecule. In yet another embodiment, the expression vector comprises: a) a transcription initiation region; b) a transcription termination region; c) an intron; d) a nucleic acid sequence encoding at least one said nucleic acid molecule; and wherein said sequence is operably linked to said initiation region, said intron and said termination region, in a manner which allows expression and/or delivery of said nucleic acid molecule.

In another embodiment, the expression vector comprises: a) a transcription initiation region; b) a transcription termination region; c) an intron; d) an open reading frame; e) a nucleic acid sequence encoding at least one said nucleic acid molecule, wherein said sequence is operably linked to the 3'-end of said open reading frame; and wherein said sequence is operably linked to said initiation region, said intron, said open reading frame, and said termination region, in a manner which allows expression and/or delivery of said nucleic acid molecule.

IV. Modified siNA Molecules

Any of the siNA constructs described herein can be evaluated and modified as described below.

An siNA construct may be susceptible to cleavage by an endonuclease or exonuclease, such as, for example, when the siNA construct is introduced into the body of a subject. Methods can be used to determine sites of cleavage, e.g., endo- and exonucleolytic cleavage on an RNAi construct and to determine the mechanism of cleavage. An siNA construct can be modified to inhibit such cleavage.

Exemplary modifications include modifications that inhibit endonucleolytic degradation, including the modifications described herein. Particularly favored modifications include: 2' modification, e.g., a 2'-O-methylated nucleotide or 2'-deoxy nucleotide (e.g., 2' deoxy-cytodine), or a 2'-fluoro, difluorotoluoyl, 5-Me-2'-pyrimidines, 5-allyamino-pyrimidines, 2'-O-methoxyethyl, 2'-hydroxy, or 2'-ara-fluoro nucleotide, or a locked nucleic acid (LNA), extended nucleic acid (ENA), hexose nucleic acid (HNA), or cyclohexene nucleic acid (CeNA). In one embodiment, the 2' modification is on the uridine of at least one 5'-uridine-adenine-3' (5'-UA-3') dinucleotide, at least one 5'-uridine-guanine-3' (5'-UG-3') dinucleotide, at least one 5'-uridine-uridine-3' (5'-UU-3') dinucleotide, or at least one 5'-uridine-cytidine-3' (5'-UC-3') dinucleotide, or on the cytidine of at least one 5'-cytidine-adenine-3' (5'-CA-3') dinucleotide, at least one 5'-cytidine-cytidine-3' (5'-CC-3') dinucleotide, or at least one 5'-cytidine-uridine-3' (5'-CU-3') dinucleotide. The 2' modification can also be applied to all the pyrimidines in an siNA construct. In one preferred embodiment, the 2' modification is a 2'OMe modification on the sense strand of an siNA construct. In a more preferred embodiment, the 2' modification is a 2' fluoro modification, and the 2' fluoro is on the sense (passenger) or antisense (guide) strand or on both strands.

Modification of the backbone, e.g., with the replacement of an O with an S, in the phosphate backbone, e.g., the provision of a phosphorothioate modification can be used to inhibit endonuclease activity. In some embodiments, an siNA construct has been modified by replacing one or more ribonucleotides with deoxyribonucleotides. Preferably, adjacent deoxyribonucleotides are joined by phosphorothioate linkages, and the siNA construct does not include more than four consecutive deoxyribonucleotides on the sense or the antisense strands. Replacement of the U with a C5 amino linker; replacement of an A with a G (sequence changes are preferred to be located on the sense strand and not the antisense strand); or modification of the sugar at the 2', 6', 7', or 8' position can also inhibit endonuclease cleavage of the siNA construct. Preferred embodiments are those in which one or more of these modifications are present on the sense but not the antisense strand, or embodiments where the antisense strand has fewer of such modifications.

Exemplary modifications also include those that inhibit degradation by exonucleases. In one embodiment, an siNA construct includes a phosphorothioate linkage or P-alkyl modification in the linkages between one or more of the terminal nucleotides of an siNA construct. In another embodiment, one or more terminal nucleotides of an siNA construct include a sugar modification, e.g., a 2' or 3' sugar modification. Exemplary sugar modifications include, for example, a 2'-O-methylated nucleotide, 2'-deoxy nucleotide (e.g., deoxy-cytodine), 2'-deoxy-2'-fluoro (2'-F) nucleotide, 2'-O-methoxyethyl (2'-O-MOE), 2'-O-aminopropyl (2'-O-AP), 2'-O—N-methylacetamido (2'-O—NMA), 2'-O-dimethylaminoethlyoxyethyl (2'-DMAEOE), 2'-O-dimethylaminoethyl (2'-DMAOE), 2'-O-dimethylaminopropyl (2'-O-AP), 2'-hydroxy nucleotide, or a 2'-ara-fluoro nucleotide, or a locked nucleic acid (LNA), extended nucleic acid (ENA), hexose nucleic acid (HNA), or cyclohexene nucleic acid (CeNA). A 2' modification is preferably 2'OMe, more preferably, 2' fluoro.

The modifications described to inhibit exonucleolytic cleavage can be combined onto a single siNA construct. For example, in one embodiment, at least one terminal nucleotide of an siNA construct has a phosphorothioate linkage and a 2' sugar modification, e.g., a 2'F or 2'OMe modification. In another embodiment, at least one terminal nucleotide of an siNA construct has a 5' Me-pyrimidine and a 2' sugar modification, e.g., a 2'F or 2'OMe modification.

To inhibit exonuclease cleavage, an siNA construct can include a nucleobase modification, such as a cationic modification, such as a 3'-abasic cationic modification. The cationic modification can be, e.g., an alkylamino-dT (e.g., a C6 amino-dT), an allylamino conjugate, a pyrrolidine conjugate, a pthalamido or a hydroxyprolinol conjugate, on one or more of the terminal nucleotides of the siNA construct. In one embodiment, an alkylamino-dT conjugate is attached to the 3' end of the sense or antisense strand of an RNAi construct. In another embodiment, a pyrrolidine linker is attached to the 3' or 5' end of the sense strand, or the 3' end of the antisense strand. In one embodiment, an allyl amine uridine is on the 3' or 5' end of the sense strand, and not on the 5' end of the antisense strand.

In one embodiment, the siNA construct includes a conjugate on one or more of the terminal nucleotides of the siNA construct. The conjugate can be, for example, a lipophile, a terpene, a protein binding agent, a vitamin, a carbohydrate, a retinoid, or a peptide. For example, the conjugate can be naproxen, nitroindole (or another conjugate that contributes to stacking interactions), folate, ibuprofen, cholesterol, retinoids, PEG, or a C5 pyrimidine linker. In other embodiments, the conjugates are glyceride lipid conjugates (e.g., a dialkyl glyceride derivative), vitamin E conjugates, or thio-cholesterols. In one embodiment, conjugates are on the 3' end of the antisense strand, or on the 5' or 3' end of the sense strand and the conjugates are not on the 3' end of the antisense strand and on the 3' end of the sense strand.

In one embodiment, the conjugate is naproxen, and the conjugate is on the 5' or 3' end of the sense or antisense strands. In one embodiment, the conjugate is cholesterol, and the conjugate is on the 5' or 3' end of the sense strand and not present on the antisense strand. In some embodiments, the cholesterol is conjugated to the siNA construct by a pyrrolidine linker, or serinol linker, aminooxy, or hydroxyprolinol linker. In other embodiments, the conjugate is a dU-cholesterol, or cholesterol is conjugated to the siNA construct by a disulfide linkage. In another embodiment, the conjugate is cholanic acid, and the cholanic acid is attached to the 5' or 3' end of the sense strand, or the 3' end of the antisense strand. In one embodiment, the cholanic acid is attached to the 3' end of the sense strand and the 3' end of the antisense strand. In another embodiment, the conjugate is PEG5, PEG20, naproxen or retinol.

In another embodiment, one or more terminal nucleotides have a 2'-5' linkage. In certain embodiments, a 2'-5' linkage occurs on the sense strand, e.g., the 5' end of the sense strand.

In one embodiment, an siNA construct includes an L-sugar, preferably at the 5' or 3' end of the sense strand.

In one embodiment, an siNA construct includes a methylphosphonate at one or more terminal nucleotides to enhance exonuclease resistance, e.g., at the 3' end of the sense or antisense strands of the construct.

In one embodiment, an siRNA construct has been modified by replacing one or more ribonucleotides with deoxyribonucleotides. In another embodiment, adjacent deoxyribonucleotides are joined by phosphorothioate linkages. In one embodiment, the siNA construct does not include more than four consecutive deoxyribonucleotides on the sense or the antisense strands. In another embodiment, all of the ribonucleotides have been replaced with modified nucleotides that are not ribonucleotides.

In some embodiments, an siNA construct having increased stability in cells and biological samples includes a difluorotoluoyl (DFT) modification, e.g., 2,4-difluorotoluoyl uracil, or a guanidine to inosine substitution.

The methods can be used to evaluate a candidate siNA, e.g., a candidate siRNA construct, which is unmodified or which includes a modification, e.g., a modification that inhibits degradation, targets the dsRNA molecule, or modulates hybridization. Such modifications are described herein. A cleavage assay can be combined with an assay to determine the ability of a modified or non-modified candidate to silence the target transcript. For example, one might (optionally) test a candidate to evaluate its ability to silence a target (or off-target sequence), evaluate its susceptibility to cleavage, modify it (e.g., as described herein, e.g., to inhibit degradation) to produce a modified candidate, and test the modified candidate for one or both of the ability to silence and the ability to resist degradation. The procedure can be repeated. Modifications can be introduced one at a time or in groups. It will often be convenient to use a cell-based method to monitor the ability to silence a target RNA. This can be followed by a different method, e.g., a whole animal method, to confirm activity.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990, *Nature* 344:565; Pieken et al., 1991, *Science* 253:314; Usman and Cedergren, 1992, *Trends in Biochem. Sci.* 17:334; Burgin et al., 1996, *Biochemistry*, 35:14090; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Vargeese et al., US 2006/021733). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

Chemically modified siNA molecules for use in modulating or attenuating expression of two or more genes down-regulated by one or more miR-34 family member are also within the scope of the invention. Described herein are isolated siNA agents, e.g., RNA molecules (chemically modified or not, double-stranded, or single-stranded) that mediate RNAi to inhibit expression of two or more genes that are down-regulated by one or more miR-34 family member.

The siNA agents discussed herein include otherwise unmodified RNA as well as RNAs which have been chemically modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., 1994, *Nucleic Acids Res.* 22:2183-2196. Such rare or unusual RNAs, often termed modified RNAs (apparently because they are typically the result of a post-transcriptional modification) are within the term unmodified RNA, as used herein.

Modified RNA as used herein refers to a molecule in which one or more of the components of the nucleic acid, namely sugars, bases, and phosphate moieties that are the components of the RNAi duplex, are different from that which occur in nature, preferably different from that which occurs in the human body. While they are referred to as "modified RNAs," they will of course, because of the modification, include molecules which are not RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Examples of all of the above are discussed herein.

Modifications described herein can be incorporated into any double-stranded RNA and RNA-like molecule described herein, e.g., an siNA construct. It may be desirable to modify one or both of the antisense and sense strands of an siNA construct. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid, but in many, and in fact in most, cases it will not.

By way of example, a modification may occur at a 3' or 5' terminal position, may occur in a terminal region, e.g. at a position on a terminal nucleotide or in the last 2, 3, 4, 5, or 10 nucleotides of a strand. A modification may occur in a double strand region, a single strand region, or in both. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, a modification may occur on an internal residue to the exclusion of adjacent residues. In some cases, the sense and antisense strands will have the same modifications, or the same class of modifications, but in other cases the sense and antisense strands will have different modifications, e.g., in some cases it may be desirable to modify only one strand, e.g., the sense strand. In some cases, the sense strand may be modified, e.g., capped in order to promote insertion of the anti-sense strand into the RISC complex.

Other suitable modifications that can be made to a sugar, base, or backbone of an siNA construct are described in US2006/0217331, US2005/0020521, WO2003/70918, WO2005/019453, PCT Application No. PCT/US2004/01193. An siNA construct can include a non-naturally occurring base, such as the bases described in any one of the above mentioned references. See also PCT Application No. PCT/US2004/011822. An siNA construct can also include a non-naturally occurring sugar, such as a non-carbohydrate cyclic carrier molecule. Exemplary features of non-naturally occurring sugars for use in siNA agents are described in PCT Application No. PCT/US2004/11829.

Two prime objectives for the introduction of modifications into siNA constructs of the invention is their stabilization towards degradation in biological environments and the improvement of pharmacological properties, e.g., pharmacodynamic properties. There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, *TIBS* 17:34; Usman et al., 1994, *Nucleic Acids Symp. Ser.* 31:163; Burgin et al., 1996, *Biochemistry*, 35:14090). Sugar modification of nucleic acid molecules has been extensively described in the art (see Eckstein et al., International Publication PCT No. WO 92/07065; Perrault et al., 1990, *Nature*, 344:565-568; Pieken et al., 1991, *Science* 253:314-317; Usman and Cedergren, 1992, *Trends in Biochem. Sci.* 17:334-339; Usman et al. International Publication PCT No. WO 93/15187; Sproat, U.S. Pat. No. 5,334,711 and Beigelman et al., 1995, *J. Biol. Chem.*, 270:25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39:1131; Earnshaw and Gait, 1998, *Biopolymers (Nucleic Acid Sciences)*, 48:39-55; Verma and Eckstein, 1998, *Annu. Rev. Biochem.*, 67:99-134; and Burlina et al., 1997, *Bioorg. Med. Chem.*, 5:1999-2010). Such publications describe general methods and strategies to determine the location of incorporation of sugar, base, and/or phosphate modifications and the like, into nucleic acid molecules without modulating catalysis. In view of such teachings, similar modifications can be used as described herein to modify the siNA molecules of the instant invention so long as the ability of siNA to promote RNAi in cells is not significantly inhibited.

Modifications may be modifications of the sugar-phosphate backbone. Modifications may also be modifications of the nucleoside portion. Optionally, the sense strand is an RNA or RNA strand comprising 5%, 10%, 20%, 30%, 40%, 50%, 60%, 70%, 80%, 90%, or 100% modified nucleotides. In one embodiment, the sense polynucleotide is an RNA strand comprising a plurality of modified ribonucleotides. Likewise, in other embodiments, the RNA antisense strand comprises one or more modifications. For example, the RNA antisense strand may comprise no more than 5%, 10%, 20%, 30%, 40%, 50%, or 75% modified nucleotides. The one or more modifications may be selected so as to increase the hydrophobicity of the double-stranded nucleic acid, in physiological conditions, relative to an unmodified double-stranded nucleic acid having the same designated sequence.

In certain embodiments, the siNA construct comprising the one or more modifications has a log P value at least 0.5 log P units less than the log P value of an otherwise identical unmodified siRNA construct. In another embodiment, the siNA construct comprising the one or more modifications has at least 1, 2, 3, or even 4 log P units less than the log P value of an otherwise identical unmodified siRNA construct. The one or more modifications may be selected so as to increase the positive charge (or increase the negative charge) of the double-stranded nucleic acid, in physiological conditions, relative to an unmodified double-stranded nucleic acid having the same designated sequence. In certain embodiments, the siNA construct comprising the one or more modifications has an isoelectric pH (pI) that is at least 0.25 units higher than the otherwise identical unmodified siRNA construct. In another embodiment, the sense polynucleotide comprises a modification to the phosphate-sugar backbone selected from the group consisting of: a phosphorothioate moiety, a phosphoramidate moiety, a phosphodithioate moiety, a PNA moiety, an LNA moiety, a 2'-O-methyl moiety, and a 2'-deoxy-2' fluoride moiety.

In certain embodiments, the RNAi construct is a hairpin nucleic acid that is processed to an siRNA inside a cell. Optionally, each strand of the double-stranded nucleic acid may be 19-100 base pairs long, and preferably 19-50 or 19-30 base pairs long.

An siNAi construct can include an internucleotide linkage (e.g., the chiral phosphorothioate linkage) useful for increasing nuclease resistance. In addition, or in the alternative, an siNA construct can include a ribose mimic for increased nuclease resistance. Exemplary internucleotide linkages and ribose mimics for increased nuclease resistance are described in PCT Application No. PCT/US2004/07070.

An siRNAi construct can also include ligand-conjugated monomer subunits and monomers for oligonucleotide synthesis. Exemplary monomers are described, for example, in U.S. application Ser. No. 10/916,185.

An siNA construct can have a ZXY structure, such as is described in co-owned PCT Application No. PCT/US2004/07070. Likewise, an siNA construct can be complexed with an amphipathic moiety. Exemplary amphipathic moieties for use with siNA agents are described in PCT Application No. PCT/US2004/07070.

The sense and antisense sequences of an siNAi construct can be palindromic. Exemplary features of palindromic siNA agents are described in PCT Application No. PCT/US2004/07070.

In another embodiment, the siNA construct of the invention can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid, or protein, e.g., an antibody, that binds to a specified cell type. iRNA agents complexed to a delivery agent are described in PCT Application No. PCT/US2004/07070.

The siNA construct of the invention can have non-canonical pairings, such as between the sense and antisense sequences of the iRNA duplex. Exemplary features of non-canonical iRNA agents are described in PCT Application No. PCT/US2004/07070.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example, Lin and Matteucci, 1998, *J. Am. Chem. Soc.*, 120:8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C methylene bicyclo nucleotide (see for example Wengel et al., International PCT Publication Nos. WO 00/66604 and WO 99/14226).

An siNA agent of the invention can be modified to exhibit enhanced resistance to nucleases. An exemplary method proposes identifying cleavage sites and modifying such sites to inhibit cleavage. An exemplary dinucleotide 5'-UA-3',5'-UG-3',5'-CA-3',5'-UU-3', or 5'-CC-3' as disclosed in PCT/US2005/018931 may serve as a cleavage site.

For increased nuclease resistance and/or binding affinity to the target, a siRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R.dbd.H, alkyl, cycloalkyl, aryl, aralkyl, heteroaryl, or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$, alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with, e.g., an amino functionality. In one embodiment, the substituents are 2'-methoxyethyl, 2'-OCH3, 2'-O-allyl, 2'-C-allyl, and 2'-fluoro.

In another embodiment, to maximize nuclease resistance, the 2' modifications may be used in combination with one or more phosphate linker modifications (e.g., phosphorothioate). The so-called "chimeric" oligonucleotides are those that contain two or more different modifications.

In certain embodiments, all the pyrimidines of a siNA agent carry a 2'-modification, and the molecule therefore has enhanced resistance to endonucleases. Enhanced nuclease resistance can also be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The siNA agent can include at least 2, at least 3, at least 4 or at least 5 of such dinucleotides. In some embodiments, the 5'-most pyrimidines in all occurrences of the sequence motifs 5'-UA-3', 5'-CA-3',5'-UU-3', and 5'-UG-3' are 2'-modified nucleotides. In other embodiments, all pyrimidines in the sense strand are 2'-modified nucleotides, and the 5'-most pyrimidines in all occurrences of the sequence motifs 5'-UA-3' and 5'-CA-3'. In one embodiment, all pyrimidines in the sense strand are 2'-modified nucleotides, and the 5'-most pyrimidines in all occurrences of the sequence motifs 5'-UA-3',5'-CA-3',5'-UU-3', and 5'-UG-3' are 2'-modified nucleotides in the antisense strand. The latter patterns of modifications have been shown to maximize the contribution of the nucleotide modifications to the stabilization of the overall molecule towards nuclease degradation, while minimizing the overall number of modifications required to achieve a desired stability, see PCT/US2005/018931. Additional modifications to enhance resistance to nucleases may be found in US2005/0020521, WO2003/70918, and WO2005/019453.

The inclusion of furanose sugars in the oligonucleotide backbone can also decrease endonucleolytic cleavage. Thus, in one embodiment, the siNA of the invention can be modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, heterocyclic conjugates, or modified sugars (D-ribose, deoxyribose, glucose, etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, heterocyclic conjugates, or modified sugars (D-ribose, deoxyribose, glucose, etc.) can block 3'-5'-exonucleases.

An alternative approach to increasing resistance to a nuclease by an siNA molecule proposes including an overhang to at least one or both strands of a duplex siNA. In some embodiments, the nucleotide overhang includes 1 to 4, preferably 2 to 3, unpaired nucleotides. In another embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In other embodiments, the nucleotide overhang may have 1 or 2 unpaired nucleotides, and in an exemplary embodiment the nucleotide overhang may be 5'-GC-3'. In another embodiment, the nucleotide overhang is on the 3'-end of the antisense strand.

Thus, an siNA molecule can include monomers which have been modified so as to inhibit degradation, e.g., by nucleases, e.g., endonucleases or exonucleases, found in the body of a subject. These monomers are referred to herein as NRMs, or Nuclease Resistance promoting Monomers or modifications. In some cases these modifications will modulate other properties of the siNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

While not wishing to be bound by theory, it is believed that modifications of the sugar, base, and/or phosphate backbone in an siNA agent can enhance endonuclease and exonuclease resistance, and can enhance interactions with transporter proteins and one or more of the functional components of the RISC complex. In some embodiments, the modification may increase exonuclease and endonuclease resistance and thus prolong the half-life of the siNA agent prior to interaction with the RISC complex, but at the same time does not render the siNA agent inactive with respect to its intended activity as a target mRNA cleavage directing agent. Again, while not wishing to be bound by any theory, it is believed that placement of the modifications at or near the 3' and/or 5'-end of antisense strands can result in siNA agents that meet the preferred nuclease resistance criteria delineated above.

Modifications that can be useful for producing siNA agents that exhibit the nuclease resistance criteria delineated above may include one or more of the following chemical and/or stereochemical modifications of the sugar, base, and/or phosphate backbone, it being understood that the art discloses other methods as well that can achieve the same result:

(i) chiral (Sp) thioates. An NRM may include nucleotide dimers enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form.

(ii) attachment of one or more cationic groups to the sugar, base, and/or the phosphorus atom of a phosphate or modified phosphate backbone moiety. In some embodiments, these may include monomers at the terminal position derivatized at a cationic group. As the 5'-end of an antisense sequence should have a terminal —OH or phosphate group, this NRM is preferably not used at the 5'-end of an antisense sequence. The group should preferably be attached at a position on the base which minimizes interference with H bond formation and hybridization, e.g., away from the face which interacts with the complementary base on the other strand, e.g., at the 5' position of a pyrimidine or a 7-position of a purine.

(iii) nonphosphate linkages at the termini. In some embodiments, the NRMs include non-phosphate linkages, e.g., a linkage of 4 atoms which confers greater resistance to cleavage than does a phosphate bond. Examples include 3' $CH_2$-$NCH_3$—O—$CH_2$-5' and 3' $CH_2$—NH—(O.dbd.)-$CH_2$-5'.

(iv) 3'-bridging thiophosphates and 5'-bridging thiophosphates. In certain embodiments, the NRMs can be included among these structures.

(v) L-RNA, 2'-5' linkages, inverted linkages, and a-nucleosides. In certain embodiments, the NRMs include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage, (vi) conjugate groups. In certain embodiments, the NRMs can include, e.g., a targeting moiety or a conjugated ligand described herein conjugated with the monomer, e.g., through the sugar, base, or backbone;

(vi) abasic linkages. In certain embodiments, the NRMs can include an abasic monomer, e.g., an abasic monomer as described herein (e.g., a nucleobaseless monomer); an aromatic or heterocyclic or polyheterocyclic aromatic monomer as described herein; and (vii) 5'-phosphonates and 5'-phosphate prodrugs. In certain embodiments, the NRMs include monomers, preferably at the terminal position, e.g., the 5' position, in which one or more atoms of the phosphate group is derivatized with a protecting group, which protecting group or groups are removed as a result of the action of a component in the subject's body, e.g., a carboxyesterase or an enzyme present in the subject's body. For example, a phosphate prodrug in which a carboxy esterase cleaves the protected molecule resulting in the production of a thioate anion which attacks a carbon adjacent to the 0 of a phosphate and resulting in the production of an unprotected phosphate.

"Ligand," as used herein, means a molecule that specifically binds to a second molecule, typically a polypeptide or portion thereof, such as a carbohydrate moiety, through a mechanism other than an antigen-antibody interaction. The term encompasses, for example, polypeptides, peptides, and small molecules, either naturally occurring or synthesized, including molecules whose structure has been invented by man. Although the term is frequently used in the context of receptors and molecules with which they interact and that typically modulate their activity (e.g., agonists or antagonists), the term as used herein applies more generally.

One or more different NRM modifications can be introduced into a siNA agent or into a sequence of a siRNA agent. An NRM modification can be used more than once in a sequence or in a siRNA agent. As some NRMs interfere with hybridization, the total number incorporated should be such that acceptable levels of siNA agent duplex formation are maintained.

In some embodiments, NRM modifications are introduced into the terminal cleavage site or in the cleavage region of a sequence (a sense strand or sequence) which does not target a desired sequence or gene in the subject.

In most cases, the nuclease-resistance promoting modifications will be distributed differently depending on whether the sequence will target a sequence in the subject (often referred to as an antisense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (as described in Elbashir et al., 2001, *Genes and Dev.* 15:188). Cleavage of the target occurs about in the middle of a 20 or 21 nt guide RNA, or about 10 or 11 nucleotides upstream of the first nucleotide which is complementary to the guide sequence. As used herein, "cleavage site" refers to the nucleotide on either side of the cleavage site, on the target, or on the iRNA agent strand which hybridizes to it. Cleavage region means a nucleotide within 1, 2, or 3 nucleotides of the cleavage site, in either direction.

Such modifications can be introduced into the terminal regions, e.g., at the terminal position, or within 2, 3, 4, or 5 positions of the terminus, of a sequence which targets or a sequence which does not target a sequence in the subject.

V. Therapeutic Use

Tumors having a defective TP53 pathway status are hypothesized to be more responsive to several oncology compounds in development (PLK1, AURA, WEE1, CHEK1) (WO 2005031002). Therefore, identification of transcripts that predict TP53 functional status may be useful for the selection of appropriate patient populations for clinical testing of these compounds. Previous studies have used genome-scale approaches to identify transcriptional markers for TP53 function. Chromatin immunoprecipitation (ChIP) was used for genome-scale analysis of TP53 transcription factor binding sites (Wie et al., (2006) *Cell* 124:207-219) Miller et al. analyzed breast cancers with sequenced TP53 and identified an expression signature that distinguished TP53-mutant and wild-type tumors, and predicted therapeutic responses (Miller et al., (2005) *PNAS* 102:13550-13555).

In one embodiment, a method is provided for treating a mammalian subject having a cancer, comprising (a) classifying a cancer cell sample from the subject as having an active TP53 pathway or an inactive TP53 pathway; and (b) treating a mammalian subject having an active TP53 pathway with a composition comprising a small interfering nucleic acid (siNA), wherein said siNA comprises a guide strand contiguous nucleotide sequence of at least 18 nucleotides, wherein said guide strand comprises a seed region consisting of nucleotide positions 1 to 12, wherein position 1 represents the 5' end of said guide strand and wherein said seed region comprises a nucleotide sequence of at least six contiguous nucleotides that is identical to six contiguous nucleotides within a sequence selected from the group consisting of SEQ ID NO:3, SEQ ID NO:6, SEQ ID NO:9, and SEQ ID NO:31.

Examples of cancers that can be treated using the compositions of the invention include, but are not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor.

In some embodiments, the compositions of the invention comprising a small interfering nucleic acid (siNA) are used to treat mammalian subjects afflicted with commonly encountered cancers such as breast, prostate, lung, ovarian, colorectal, and brain cancer. In some embodiments, the compositions of the invention comprising a small interfering nucleic acid (siNA) are used to inhibit the proliferation of a cancer cell that is c-MET dependent. In some embodiments, the compositions of the invention are used to treat mammalina subjects afflicted with c-MET dependent non-small cell lung carcinoma.

In general, an effective amount of the one or more compositions of the invention for treating a mammalian subject afflicted with cancer will be that amount necessary to inhibit mammalian cancer cell proliferation in situ. Those of ordinary skill in the art are well-schooled in the art of evaluating effective amounts of anti-cancer agents.

In some cases, the above-described treatment methods may be combined with known cancer treatment methods. The term "cancer treatment" as used herein, may include, but is not limited to, chemotherapy, radiotherapy, adjuvant therapy, surgery, or any combination of these and/or other methods. Particular forms of cancer treatment may vary, for instance, depending on the subject being treated. Examples include, but are not limited to, dosages, timing of administration, duration of treatment, etc. One of ordinary skill in the medical arts can determine an appropriate cancer treatment for a subject.

The molecules of the instant invention can be used as pharmaceutical agents. Pharmaceutical agents prevent, inhibit the occurrence of, or treat (alleviate a symptom to some extent, preferably all of the symptoms) a disease state in a subject.

The negatively charged polynucleotides of the invention can be administered (e.g., RNA, DNA or protein complex thereof) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary, and intramuscular. Each of these administration routes exposes the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as lymphocytes and macrophages, is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, *Fundam. Clin. Pharmacol.*, 13:16 26); biodegradable polymers, such as poly (DL-lactide-coglycolide) microspheres for sustained release delivery after implantation (Emerich, D F et al., 1999, *Cell Transplant*, 8:47 58) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23:941-949, 1999). Nanoparticles functionalized with lipids (lipid nanoparticles), such as lysine-containing nanoparticles with the surface functional groups modified with lipid chains may also be used for delivery of the nucleic acid molecules of the instant invention. Such lipid nanoparticles may be generated as described in Baigude H. et al., *ACS Chemical Biology* Vol 2(4): 237-241 (2007), incorporated herein by reference. Other non-limiting examples of delivery strategies, including CNS delivery of the nucleic acid molecules of the instant invention include material described in Boado et al., 1998, *J. Pharm. Sci.*, 87:1308-1315; Tyler et al., 1999, *FEBS Lett.*, 421:280-284; Pardridge et al., 1995, *PNAS USA.*, 92:5592-5596; Boado, 1995, *Adv. Drug Delivery Rev.*, 15:73-107; Aldrian-Herrada et al., 1998, *Nucleic Acids Res.*, 26:4910-4916; and Tyler et al., 1999, *PNAS USA.*, 96:7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., 1995, *Chem. Rev.* 95:2601-2627; Ishiwata et al., 1995, *Chem. Pharm. Bull.* 43:1005-1011). Such liposomes have been shown to accumulate selectively in tumors, presumably by extravasation and capture in the neovascularized target tissues (Lasic et al., 1995, *Science* 267:1275-1276; Oku et al., 1995, *Biochim. Biophys. Acta*, 1238:86-90). The long-circulating liposomes enhance the pharmacokinetics and pharmacodynamics of DNA and RNA, particularly compared to conventional cationic liposomes which are known to accumulate in tissues of the MPS (Liu et al., 1995, *J. Biol. Chem.* 42:24864-24870; Choi et al., International PCT Publication No. WO 96/10391; Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro ed., 1985) hereby incorporated by reference herein. For example, preservatives, stabilizers, dyes, and flavoring agents can be provided. These include sodium benzoate, sorbic acid, and esters of p-hydroxybenzoic acid. In addition, antioxidants and suspending agents can be used.

A pharmaceutically effective dose is the dose required to prevent, inhibit the occurrence of, or treat (alleviate a symptom to some extent, preferably all of the symptoms) a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered, depending upon the potency of the negatively charged polymer.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and, if desired, other active ingredients. The pharmaceutical compositions containing nucleic acid molecules of the invention can be in a form suitable for oral use, for example, as tablets, troches, lozenges, aqueous or oily suspensions, dispersible powders or granules, emulsions, hard or soft capsules, or syrups or elixirs.

In some embodiments, the compositions are administered locally to a localized region of a subject, such as a tumor, via local injection.

Compositions intended for oral use can be prepared according to any method known in the art for the manufacture of pharmaceutical compositions, and such compositions can contain one or more such sweetening agents, flavoring agents, coloring agents, or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch or alginic acid; binding agents, for example starch, gelatin, or acacia; and lubricating agents, for example magnesium stearate, stearic acid, or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients may include suspending agents, for example sodium carboxymethylcellulose, methylcellulose, hydropropyl-methylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil, or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring, and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example, gum acacia or gum tragacanth; naturally-occurring phosphatides, for example, soy bean, lecithin, and esters or partial esters derived from fatty acids and hexitol; anhydrides, for example, sorbitan monooleate; and condensation products of the said partial esters with ethylene oxide, for example, polyoxyethylene sorbitan monooleate. The emulsions can also contain sweetening and flavoring agents.

Syrups and elixirs can be formulated with sweetening agents, for example, glycerol, propylene glycol, sorbitol, glucose, or sucrose. Such formulations can also contain a demulcent, a preservative, and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels on the order of from about 0.1 mg to about 140 mg per kilogram of body weight per day are useful in the treatment of the above-indicated conditions (about 0.5 mg to about 7 g per patient or subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient or subject depends upon a variety of factors including the activity of the specific compound employed, the age, body weight, general health, sex, diet, time of administration, route of administration, rate of excretion, drug combination, and the severity of the particular disease undergoing therapy.

For administration to non-human animals, the composition can also be added to the animal's feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Examples are provided below to further illustrate different features and advantages of the present invention. The examples also illustrate useful methodology for practicing the invention. These examples do not limit the claimed invention.

EXAMPLE 1

This Example demonstrates that shRNA-mediated suppression of TP53 downregulates expression of an EST Cluster (Contig6654) that contains the miR-34a locus.

Rationale:

Cells having wild type TP53 arrest at a G1 checkpoint following DNA damage to allow DNA repair prior to cell cycle progression. shRNA-mediated disruption of TP53 eliminates this G1 arrest (Brummelkamp et al., (2002) *Science* 296:550-553). A series of tumor cell lines were tested for G1 arrest following Doxorubicin treatment to confirm the integrity of the TP53 pathway. Eight tumor lines reported as having normal TP53 activity were used in this study: A549 (lung carcinoma, O'Connor et al., *Cancer Res.* 57:4285-300), TOV21G (ovarian carcinoma, Samouelian et al., 2004, *Cancer Chemother. Pharmacol* 54:497-504), MCF7 (breast carcinoma, Concin et al., 2003 *Breast Cancer Res. Treat.* 79:37-46), HEPG2 (hepatic carcinoma, Bamford, et al., 2004, *Br. J. Cancer* 91:355-58), OAW42 (ovarian carcinoma, Bamford et al., 2004, *Br. J. Cancer* 91:355-58); A2780 (ovarian carcinoma, Bamford, et al., 2004, *Br. J. Cancer* 91:355-58); U2OS (osteosarcoma, Zhu et al., 1993 *Genes & Dev.* 7:1111-25); and NCI-H460 (lung carcinoma, O'Connor et al., 1997 *Cancer Res.* 57:4285-300).

Methods:

A series of matched cell line pairs with or without functional TP53 were created. Multiple cell lines were made to avoid idiosyncratic effects particular to any single cell line. Stable cell lines were transduced with an empty lentiviral vector or with a lentiviral vector encoding an shRNA targeting TP53. The vectors used were pLenti6/BLOCK-iT-DEST destination vectors (Invitrogen Corporation, Carlsbad, Calif.) into which had been transferred a Gateway (Invitrogen)-compatible expression cassette containing the human H1 promoter upstream of an shRNA targeting TP53 or a terminator sequence consisting of a stretch of five thymidines, a BamHI site, and then another five thymidines.

TP53 shRNA used in these experiments had the 19-nucleotide core sequence 5' GACUCCAGUGGUAAUCUAC 3' [SEQ ID NO:10]. The full hairpin sequence cloned into the lentiviral vector was: 5' GACUCCAGUGGUAA UCUACU-UCAAGAGAGUAGAUUACCACUGGAGUCUUUUU 3' [SEQ ID NO:11].

TP53 mRNA levels were reduced by ~80-95% in cell lines expressing the TP53 shRNA as compared with cells transduced with empty vector (data not shown). A549 cells (lung carcinoma) were transduced with an empty lentiviral vector (LV vector) or with a vector encoding an shRNA hairpin targeting TP53 (p53 shRNA), and stable cell lines were isolated. In brief, cells at 50% to 70% confluence were inoculated with virus at a multiplicity of infection (MOI) of 10 transducing units per cell (TU/cell) in DMEM with 10% FBS and 6 μg/ml polybrene. After 24 hours, the virus was removed and the cultures were replenished with fresh DMEM plus 10% FBS. Transduced cells were drug selected with 5 ug/ml blasticidin, which was added to the medium 4-5 days after transduction. Stable cells were treated with doxorubicin (+Doxorubicin) or without (−Doxorubicin) for 24 hours and then subjected to cell cycle analysis by flow cytometry.

As shown in FIGS. 2A-2D, all cells expressing TP53 shRNA showed reduced G1 arrest following treatment with doxorubicin to induce DNA damage. FIG. 2A is a histogram of cells with wildtype p53 showing the number of cells (Y axis) with a given DNA content (measured by fluorescence intensity, X axis). FIG. 2B is a histogram of cells with wildtype p53 treated with doxorubicin showing the number of cells (Y axis) with a given DNA content (measured by fluorescence intensity, X axis). FIG. 2C is a histogram of cells with wildtype p53 transfected with TP53 shRNA showing the number of cells (Y axis) with a given DNA content (measured by fluorescence intensity, X axis), and FIG. 2D is a histogram of cells with wildtype p53 transfected with TP53 shRNA and treated with doxorubicin showing the number of cells (Y axis) with a given DNA content (measured by fluorescence intensity, X axis), showing that disruption of TP53 ablates G0/G1 checkpoint following DNA damage. As shown in FIGS. 2A-2D, suppression of TP53 diminishes the G0/G1 checkpoint.

Messenger RNA (mRNA) was isolated from each line and subjected to DNA microarray analysis, with comparisons made between cells transduced with empty Lentivirus vector versus cells transduced with the Lentivirus vector encoding TP53 shRNA. To eliminate experimental noise, genes were identified as being regulated by TP53 if they were regulated >1.5-fold, P<0.01, in 5 or more cell lines. On the basis of these criteria, Contig6654 was identified as a transcript that was affected by the TP53 shRNA disruption of TP53 function.

Table 2 provides the fold change in log 10 ratio of hybridization intensity for the selected genes in empty vector-transduced cells compared with TP53 shRNA-transduced A549 cells. Results shown in Table 2 are derived from competitive hybridization microarray studies comparing A549 cells expressing a TP53 targeting shRNA versus A549 cells carrying a control vector. TP53 was down-regulated in the about 5-fold in cells expressing the shRNA targeting TP53 verses cells expressing an empty vector.

TABLE 2

Effects of shRNA-mediated suppression of TP53 on transcript levels of known TP53 regulated genes.

| Primary Sequence Name | Accession # | Fold change in transcript level |
|---|---|---|
| TP53I3 | NM_004881 | 1.153201 |
| INPP5D | NM_005541 | −1.650142 |
| DDB2 | NM_000107 | −1.853958 |
| CYFIP2 | NM_030778 | −2.091289 |
| CDKN1A | NM_000389 | −2.623143 |
| TRIM22 | NM_006074 | −1.203311 |
| ACTA2 | NM_001613 | −3.774972 |
| FAS | NM_152873 | −1.93776 |
| BTG2 | NM_006763 | −1.828167 |
| SESN1 | NM_014454 | −2.000987 |
| FDXR | NM_004110 | −2.132721 |
| BBC3 | NM_014417 | −1.516828 |
| TP53INP1 | NM_033285 | −3.438426 |
| PLK2 | NM_006622 | −1.067533 |
| PHLDA3 | NM_012396 | −1.722152 |
| RRM2B | NM_015713 | −1.806952 |
| GADD45A | NM_001924 | −1.288047 |
| BAX | NM_138763 | 1.010626 |
| INSIG1 | NM_005542 | −1.579872 |
| Contig6654_RC | | −1.936355 |

Each cell line pair gave distinct but overlapping gene expression signatures, primarily comprising low magnitude regulations. As shown in Table 2, TP53 was strongly down-regulated in all cases, but most of the other reporters showed weaker regulations that varied between different cell lines.

Contig6654_RC is a poorly characterized EST cluster. Mapping of this contig to the human genome was performed using a genome browser software and database package publicly provided by the University of California at Santa Cruz (UCSC) which included a comparison of STS Markers on genetic and radiation hybrid maps, known genes based on UniProt, RefSeq and GenBank mRNA and microRNA species as described in the publicly available miRBase sequence database as described in Griffith-Jones et al., *Nucleic Acids Research* 32:D109-D111 (2004) and Griffith-Jones et al., *Nucleic Acids Research* 34:D140-D144 (2006), accessible on the World Wide Web at the Wellcome Trust Sanger Institute website. Inspection of the above described information in the UCSC genome browser revealed that Contig6654 belongs to an EST cluster that overlaps with a microRNA locus, miR-34a, leading to the hypothesis that disruption of TP53 function down-regulates a miRNA precursor of miR-34a. Confirmation of this hypothesis is demonstrated in Example 2.

EXAMPLE 2

This Example demonstrates that cellular levels of miR-34 are correlated with the level of TP53 in human cells.

Methods:

To look for miRNAs whose levels might correlate with TP53 function in cell lines, miRNA copy numbers were determined for a set of ~200 miRNAs in a panel of matched pair cell lines that were engineered such that one member of the matched cell line pair expressed an shRNA targeting TP53, while the other cell line carried an empty vector control. Quantitative PCR measurement of TP53 transcript levels from these cells confirmed that TP53 transcript levels had been knocked down by 90%-95% in the cell line expressing the TP53 shRNA.

MicroRNA levels were measured using quantitative real time polymerase chain reaction assay (RT-PCR) as described by Raymond et al. (*RNA*, 2005, 11:1737-1744; PCT publication WO 2005/031002 (Table 6)).

Results: As shown in FIG. 3A, the TP53-deficient member of each matched pair of cell lines TOV21G and HepG2 showed decreased levels (~20%) of miR-34a, with a paired t-test of all of the microRNA dataset showing that miR-34a was the most significantly decreased miRNA of the miRNA set. Cell lines MCF7, A549, and NCI-460 were also tested in this experiment and showed similar results (data not shown).

Figure 3B:
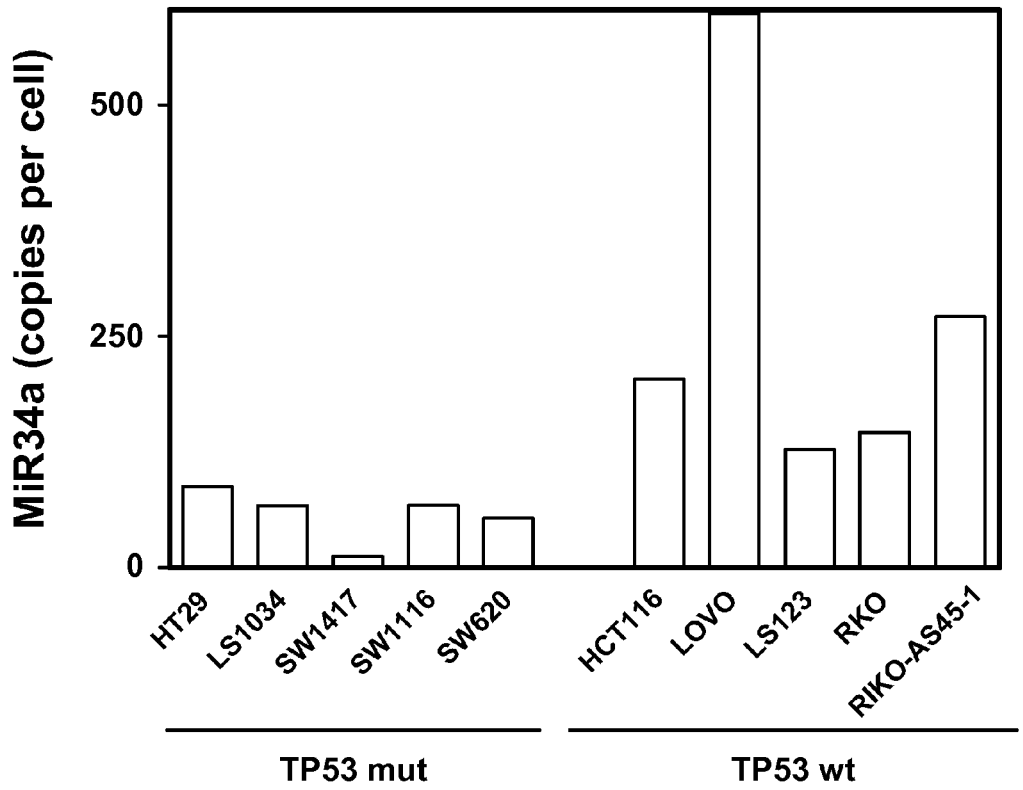
FIG. 3B graphically illustrates the per cell copy number of miR-34a in a panel of non-engineered colon tumor lines that express mutant or wild type (wt) TP53 showing that miR-34 levels in a cell are correlated with TP53 status.

Copy numbers for miR-34a, miR-34b, and miR-34c were also measured in a number of non-engineered cell lines having a previously determined wild-type TP53 status (HCT116 (Vassilev et al., *Science*, 2004, 303:844-8), LOVO (Cottu et al., *Cancer Res.*, 1995, 13:2727-30), LS123 (Bamford et al., 2004 Br. J. Cancer 91:355-58), RKO (Vassilev et al., *Science*, 2004, 303:844-8) and RKO-AS45-1 (Bamford, et al., 2004 Br. J. Cancer 91:355-58) or mutant TP53 status (HT29 (Rodrigues et al., *PNAS*, 1990, 87:7555-9), LS1034 (Liu and Bodmer, *PNAS*, 2006, 103:976-81), SW1417 (Liu and Bodmer, *PNAS*, 2006, 103:976-81), SW1116 (Liu and Bodmer, *PNAS*, 2006, 103:976-81), and SW620 Rodrigues et al., *PNAS*, 1990, 87:7555-9) A549 (lung carcinoma, O'Connor et al., 1997, *Cancer Res.* 57:4285-300), TOV21G (ovarian carcinoma, Samouelian et al., 2004, *Cancer Chemother. Pharmacol.* 54:497-504), MCF7 (breast carcinoma, Concin et al., 2003, *Breast Cancer Res. Treat.* 79:37-46), HEPG2 (hepatic carcinoma, Bamford, et al., 2004 Br. J. Cancer 91:355-58), OAW42 (ovarian carcinoma, Bamford, et al., 2004 Br. J. Cancer 91:355-58); A2780 (ovarian carcinoma, Bamford, et al., 2004 Br. J. Cancer 91:355-58); U2OS (osteosarcoma, Zhu et al., 1993, *Genes & Dev.* 7:1111-25); and NCI-H460 (lung carcinoma, O'Connor et al., 1997, *Cancer Res.* 57:4285-300)). For cell lines with unknown TP53 status, TP53 functionality was inferred based upon the expression level of a TP53-responsive reporter gene construct (p53REbla, Catalog No. K1193, Invitrogen Corporation (Carlsbad, Calif.)) introduced into the cell line being tested. In addition, all of the cell lines used in this study were derived from a single tissue type (colon). As shown in FIG. 3B, the cell lines characterized as having mutant TP53 exhibited about 4-fold lower miR-34a levels compared with the cells lines having wild-type TP53 function.

To evaluate possible direct effects of TP53 activation on miR-34 levels, the TOV21G cells were also treated with the DNA-damaging agent doxorubicin, which induces DNA damage. Consistent with a role for activated TP53 in miR-34 regulation, doxorubicin (Adriamycin) treatment led to significant increases in miR-34 levels as shown below in Table 3. Other cells having TP53 activity showed similar results to those shown in Table 3 (data not shown). Compared with mock-treated cells, doxorubicin-treated cells showed 10-40 fold increases in miR-34a, miR-34b, and miR-34c. These observations are consistent with a regulatory role for TP53 in miR-34 transcription.

TABLE 3

Copies per cell of 194 miRNAs in TOV21G cells untreated or treated with adriamycin for 48 hr.

| microRNA | copies per cell $^a$ untreated | Adriamycin | induction (fold) |
|---|---|---|---|
| miR-34c | 9 | 420 | 46.7 |
| miR-34b | 1 | 27 | 27.0 |
| miR-143 | 14 | 255 | 18.2 |
| miR-302a | 1 | 15 | 15.0 |
| miR-194 | 148 | 2153 | 14.5 |
| miR-145 | 11 | 143 | 13.0 |
| miR-34a | 673 | 8619 | 12.8 |
| miR-215 | 117 | 1463 | 12.5 |
| miR-203 | 2 | 24 | 12.0 |
| miR-192 | 1315 | 14670 | 11.2 |
| miR-101 | 17 | 163 | 9.6 |
| miR-29b | 6066 | 52782 | 8.7 |
| miR-149 | 17 | 147 | 8.6 |
| miR-96 | 264 | 2198 | 8.3 |
| miR-152 | 41 | 340 | 8.3 |
| miR-182 * | 1 | 8 | 8.0 |
| miR-135a | 1 | 8 | 8.0 |
| miR-132 | 11 | 85 | 7.7 |
| miR-130a | 567 | 4148 | 7.3 |
| miR-30a-5p | 3680 | 26565 | 7.2 |
| miR-29a | 2981 | 21456 | 7.2 |
| miR-30e-3p | 1624 | 11619 | 7.2 |
| miR-146 | 422 | 2972 | 7.0 |
| miR-205 | 1 | 7 | 7.0 |
| miR-182 | 369 | 2566 | 7.0 |
| miR-1 | 5 | 34 | 6.8 |
| miR-21 | 3989 | 27023 | 6.8 |
| miR-138 | 58 | 390 | 6.7 |
| miR-23a | 9341 | 61504 | 6.6 |
| miR-183 | 965 | 6184 | 6.4 |
| miR-30d | 1732 | 10903 | 6.3 |
| miR-141 | 93 | 573 | 6.2 |
| miR-107 | 823 | 5022 | 6.1 |
| miR-133b | 1 | 6 | 6.0 |
| miR-27a | 24863 | 142759 | 5.7 |
| miR-133a | 3 | 17 | 5.7 |
| miR-103 | 854 | 4831 | 5.7 |
| miR-30e-5p | 435 | 2436 | 5.6 |
| miR-23b | 16956 | 89406 | 5.3 |
| miR-10b | 285 | 1490 | 5.2 |
| miR-30c | 5251 | 25088 | 4.8 |
| miR-27b | 8626 | 40525 | 4.7 |
| miR-31 | 1305 | 6026 | 4.6 |
| miR-32 | 715 | 3292 | 4.6 |
| miR-181a | 370 | 1680 | 4.5 |
| miR-26a | 657 | 2948 | 4.5 |
| miR-30b | 2878 | 12684 | 4.4 |
| miR-153 | 138 | 598 | 4.3 |
| miR-126 | 150 | 647 | 4.3 |
| miR-26b | 983 | 4225 | 4.3 |
| miR-148a | 18 | 76 | 4.2 |
| miR-28 | 504 | 2123 | 4.2 |
| miR-148b | 1148 | 4796 | 4.2 |
| miR-181c | 13 | 54 | 4.2 |
| miR-98 | 3892 | 15978 | 4.1 |
| miR-155 | 46 | 186 | 4.0 |
| miR-125a | 1125 | 4532 | 4.0 |

TABLE 3-continued

Copies per cell of 194 miRNAs in TOV21G cells untreated or treated with adriamycin for 48 hr.

| microRNA | copies per cell $^a$ untreated | Adriamycin | induction (fold) |
|---|---|---|---|
| miR-125b | 2285 | 9197 | 4.0 |
| miR-147 | 4 | 16 | 4.0 |
| miR-99a | 1493 | 5952 | 4.0 |
| miR-106b | 508 | 2014 | 4.0 |
| miR-135b | 32 | 125 | 3.9 |
| miR-100 | 1210 | 4589 | 3.8 |
| miR-15a | 605 | 2280 | 3.8 |
| miR-33 | 14 | 52 | 3.7 |
| miR-151 | 129 | 466 | 3.6 |
| miR-204 | 5 | 18 | 3.6 |
| miR-150 | 5 | 18 | 3.6 |
| miR-140 | 77 | 276 | 3.6 |
| miR-10a | 798 | 2795 | 3.5 |
| miR-128b | 104 | 363 | 3.5 |
| miR-193 | 66 | 221 | 3.3 |
| miR-19b | 489 | 1628 | 3.3 |
| miR-130b | 549 | 1819 | 3.3 |
| miR-19a | 1975 | 6016 | 3.0 |
| miR-134 | 1 | 3 | 3.0 |
| miR-15b | 661 | 1947 | 2.9 |
| miR-16 | 52210 | 151512 | 2.9 |
| miR-9 * | 895 | 2591 | 2.9 |
| miR-99b | 321 | 924 | 2.9 |
| miR-20 | 468 | 1346 | 2.9 |
| miR-222 | 1674 | 4781 | 2.9 |
| miR-17-3p | 82 | 231 | 2.8 |
| miR-128a | 177 | 481 | 2.7 |
| miR-25 | 176 | 461 | 2.6 |
| miR-221 | 255 | 667 | 2.6 |
| miR-106a | 594 | 1530 | 2.6 |
| miR-190 | 75 | 191 | 2.5 |
| miR-92 | 1776 | 4450 | 2.5 |
| miR-198 | 2 | 5 | 2.5 |
| miR-17-5p | 401 | 979 | 2.4 |
| miR-370 | 30 | 73 | 2.4 |
| miR-127 | 17 | 41 | 2.4 |
| miR-331 | 204 | 487 | 2.4 |
| miR-340 | 37 | 88 | 2.4 |
| miR-218 | 28 | 65 | 2.3 |
| miR-93 | 317 | 735 | 2.3 |
| miR-189 | 4 | 9 | 2.3 |
| miR-328 | 47 | 102 | 2.2 |
| miR-302b | 43 | 92 | 2.1 |
| miR-330 | 16 | 33 | 2.1 |
| miR-302d | 18 | 37 | 2.1 |
| miR-202 | 19 | 39 | 2.1 |
| miR-382 | 2 | 4 | 2.0 |
| miR-381 | 4 | 8 | 2.0 |
| miR-380-3p | 2 | 4 | 2.0 |
| miR-302c * | 13 | 26 | 2.0 |
| miR-212 | 1 | 2 | 2.0 |
| miR-199b | 1 | 2 | 2.0 |
| miR-199a * | 6 | 12 | 2.0 |
| miR-326 | 35 | 67 | 1.9 |
| miR-410 | 338 | 625 | 1.8 |
| miR-380-5p | 6 | 11 | 1.8 |
| miR-199a | 5 | 9 | 1.8 |
| miR-423 | 126 | 224 | 1.8 |
| miR-216 | 13 | 23 | 1.8 |
| miR-324-3p | 75 | 132 | 1.8 |
| miR-450 | 7 | 12 | 1.7 |
| miR-302a * | 3 | 5 | 1.7 |
| miR-195 | 1474 | 2448 | 1.7 |
| miR-339 | 88 | 146 | 1.7 |
| miR-200a | 4792 | 7907 | 1.7 |
| miR-186 | 195 | 320 | 1.6 |
| miR-301 | 360 | 585 | 1.6 |
| miR-374 | 1922 | 3113 | 1.6 |
| miR-214 | 21 | 34 | 1.6 |
| miR-324-5p | 73 | 117 | 1.6 |
| miR-378 | 5 | 8 | 1.6 |
| miR-373 * | 10 | 16 | 1.6 |
| miR-196a | 105 | 160 | 1.5 |

TABLE 3-continued

Copies per cell of 194 miRNAs in TOV21G cells untreated or treated with adriamycin for 48 hr.

| microRNA | copies per cell[a] untreated | Adriamycin | induction (fold) |
|---|---|---|---|
| miR-425 | 19 | 28 | 1.5 |
| miR-320 | 604 | 874 | 1.4 |
| miR-196b | 345 | 495 | 1.4 |
| miR-200b | 570 | 773 | 1.4 |
| miR-323 | 3 | 4 | 1.3 |
| miR-429 | 405 | 529 | 1.3 |
| miR-346 | 11 | 14 | 1.3 |
| miR-220 | 19 | 24 | 1.3 |
| miR-188 | 46 | 56 | 1.2 |
| miR-363 | 168 | 184 | 1.1 |
| miR-372 | 1 | 1 | 1.0 |
| miR-325 | 2 | 2 | 1.0 |
| miR-299 | 1 | 1 | 1.0 |
| miR-223 | 1 | 1 | 1.0 |
| miR-211 | 2 | 2 | 1.0 |
| miR-154 * | 1 | 1 | 1.0 |
| miR-197 | 216 | 210 | 1.0 |
| miR-422b | 26 | 25 | 1.0 |
| miR-210 | 72 | 68 | 0.9 |
| miR-451 | 25 | 23 | 0.9 |
| miR-7 | 2804 | 2520 | 0.9 |
| miR-345 | 46 | 41 | 0.9 |
| miR-191 | 1768 | 1471 | 0.8 |
| miR-208 | 135 | 95 | 0.7 |
| miR-424 | 28 | 19 | 0.7 |
| miR-224 | 9 | 6 | 0.7 |
| miR-379 | 7 | 4 | 0.6 |
| miR-217 | 2107 | 919 | 0.4 |
| miR-95 | 0 | 8 | N/A |
| miR-449 | 0 | 0 | N/A |
| miR-448 | 0 | 0 | N/A |
| miR-431 | 0 | 0 | N/A |
| miR-422a | 0 | 0 | N/A |
| miR-412 | 0 | 0 | N/A |
| miR-383 | 0 | 0 | N/A |
| miR-376b | 0 | 0 | N/A |
| miR-375 | 0 | 0 | N/A |
| miR-373 | 0 | 0 | N/A |
| miR-371 | 0 | 0 | N/A |
| miR-368 | 0 | 0 | N/A |
| miR-367 | 0 | 1 | N/A |
| miR-342 | 0 | 0 | N/A |
| miR-338 | 0 | 0 | N/A |
| miR-337 | 0 | 0 | N/A |
| miR-302c | 0 | 0 | N/A |
| miR-302b * | 0 | 1 | N/A |
| miR-296 | 0 | 0 | N/A |
| miR-213 | 0 | 0 | N/A |
| miR-206 | 0 | 0 | N/A |
| miR-187 | 0 | 5 | N/A |
| miR-184 | 0 | 1 | N/A |
| miR-154 | 0 | 9 | N/A |
| miR-144 | 0 | 31 | N/A |
| miR-142-3p | 0 | 0 | N/A |
| miR-139 | 0 | 0 | N/A |
| miR-137 | 0 | 2 | N/A |
| miR-136 | 0 | 0 | N/A |
| miR-129 | 0 | 8 | N/A |
| miR-126 * | 0 | 36 | N/A |
| miR-124a | 0 | 2 | N/A |
| miR-122a | 0 | 1 | N/A |
| miR-105 | 0 | 0 | N/A |

[a] Copies per cell of 194 miRNAs and miRNAs are determined using real time PCR analysis using the method described in Raymond C. K. et al., RNA 11; 1737-1744 (2005). ACt values were converted to copy number by comparison with standard curves generated by use of defined inputs of single stranded mature miRNAs.
The symbol * refers to miRNA strands that are the complementary strands of the functional single-stranded miRNAs. These are initially part of the double-stranded miRNA molecule before processing by Dicer, and are generally degraded by the cell.

EXAMPLE 3

The experiments in this Example show miR-34 expression is directly regulated by TP53 in mouse embryonic fibroblast (MEF) cells.

Methods:

Mouse embryonic fibroblast (MEF) cells were isolated from E13.5 embryos as described by (Nagy et al., 2003 *Manipulating the Mouse Embryo: A Laboratory Manual*, 3$^{rd}$ ed., Cold Spring Harbor Lab. Press. Cold Spring Harbor, N.Y.). In MEFs expressing a tetracycline-regulated TP53 shRNA, endogenous TP53 activity gradually increased over a period of 6-8 days following repression of the shRNA (Dickins et al., 2005, *Nat. Genet.* 37:1289-95). In this experiment, miR34 levels were measured in MEF cells expressing a tetracycline repressible TP53 shRNA over an eight day period after being treated with deoxycycline (as described in Dickins et al., 2005 supra).

Results:

Cells grown in the absence of doxycycline express high levels of TP53 shRNA which suppresses TP53 activity. As shown below in Table 4 at Day 0, TP53 negative cells have a low level of miR-34 a, b, and c relative to MEF cells treated with doxycycline for 4 to 8 days. As shown in Table 4, reactivation of TP53 in MEF cells led to significant induction of both the mature miR-34s and their primary transcripts.

TABLE 4

Up-regulation of miR-34 levels after reactivation of TP53 activity in MEF cells.

| Days after treatment of MEF cells with doxycycline | Fold-up-regulation of miR-34a compared to Day 0 | Fold-up-regulation of miR-34b compared to Day 0 | Fold-up-regulation of miR-34c compared to Day 0 |
|---|---|---|---|
| Day 0 | 1 (±0.1)[1] | 1 (±0.1) | 1 (±0.1) |
| Day 1 | 0.8 (±0.1) | 0.6 (±0.1) | 0.8 (±0.3) |
| Day 2 | 1.6 (±0.1) | 0.6 (±0.1) | 0.8 (±0.1) |
| Day 4 | 16.9 (±1.8) | 5.8 (±1.0) | 6.1 (±0.5) |
| Day 6 | 37.1 (±3.6) | 11.7 (±2.0) | 10.9 (±0.9) |
| Day 8 | 35.5 (±4.0) | 17.8 (±3.8) | 17.9 (±0.6) |

[1]Error is standard deviation of multiple measurement.

EXAMPLE 4

This Example demonstrates that cellular levels of miR-34 are correlated with the level of TP53 in live mice.

Methods:

Multiple physiological stresses can, through distinct signaling pathways and molecular mechanisms, induce accumulation of TP53 protein and activate TP53 pathway-mediated transcriptional programs. For example, DNA damage mediates TP53 activation mainly through post-translational modification (Giaccia and Kastan, 1998, *Genes Dev.* 12:2973-83; Fei and El-Deiry, 2003, *Oncogene* 22:5774-83).

Wild-type and p53$^{-/-}$ mice were subjected to 6 Gy of ionizing irradiation, and miR-34 levels were measured in spleens by real time PCR both before and at the indicated times post-irradiation as described by Xue et al. (2007, *Nature* 445:656-60).

Results:

As shown in Table 5, the level of miR-34 a, b, and c in mice exposed to ionizing irradiation was induced 5 to 10 fold four hours after exposure, while the TP53 defective mice showed no induction of miR-34 levels. These data show that in live mice TP53 function is required for irradiation mediated induction of miR-34 levels.

TABLE 5

Up-regulation of miR-34 levels after irradiation of TP53$^{+/+}$ and TP53$^{-/-}$ mice.

| Treatment with Ionizing irradiation (IR) | Fold-up-regulation of miR-34a compared to TP53+, no IR mice | Fold-up-regulation of miR-34b compared to TP53+, no IR mice | Fold-up-regulation of compared to TP53+, no IR mice |
|---|---|---|---|
| Wildtype TP53+ mice No IR | 1 (±0.04)[1] | 1 (±0.08) | 1 (±0.07) |
| 4 hours after IR | 9.3 (±0.7) | 5.0 (±0.2) | 5.9 (±0.3) |
| 8 hours after IR | 4.3 (±0.8) | 2.3 (±0.6) | 3.2 (±0.2) |
| TP53$^{-/-}$ mice No IR | 0.6 (±0.04) | 0.9 (±0.17) | 0.6 (±0.05) |
| 4 hours after IR | 1.2 (±0.05) | 0.3 (±0.08) | 0.8 (±0.1) |
| 8 hours after IR | 0.7 (±0.09) | 0.4 (±0.05) | 0.7 (±0.8) |

[1]Error is standard deviation of multiple measurement.

EXAMPLE 5

This Example demonstrates that miR-34a, b, and c levels found in mouse tumors in vivo correlate with TP53 activity.

Rationale:

Oncogene activation that leads to inappropriate mitogenic stimulation often activates the TP53 pathway via induction of ARF (Sherr et al., 2000, *Curr. Opin. Genet. Dev.* 10:94-9). An example of such a response was evident in a recently reported mouse hepatocellular carcinoma model, wherein tumor formation and maintenance driven by activated ras required continuous suppression of TP53 by an inducible shRNA (Xue et al., 2007, *Nature* 445:656-60). Loss of shRNA expression, in response to doxycycline treatment in vivo, reconstituted the p53 pathway and resulted in the senescence of tumor cells (Xue et al., 2007, *Nature* 445:656-60).

Methods:

Hepatocellular carcinomas were produced by combined expression of activated ras and a conditional p53 shRNA, as described by Xue et al. (2007, *Nature* 445:656-60). Suppression of TP53 by the TP53shRNA was relieved by treatment with doxycycline. Tumors were harvested at the times indicated in Table 6 during doxycycline treatment, and levels of mature miR-34 were measured by quantitative-PCR. Levels of miR-34a, miR-34b, and miR-34c were plotted with respect to tumors prior to TP53 reactivation.

Results:

TABLE 6

Up-regulation of miR-34 a, b, and c levels in tumors isolated from ras activated, conditional expression of TP53shRNA..

| Days after treatment with doxycycline | Fold-up-regulation of miR-34a compared to Day 0 | Fold-up-regulation of miR-34b compared to Day 0 | Fold-up-regulation of miR-34c compared to Day 0 |
|---|---|---|---|
| Day 0 | 1 (±0.1)[1] | 1 (±0.2) | 1 (±0.1) |
| Day 4 | 3.5 (±0.6) | 1.8 (±0.1) | 1.8 (±0.3) |
| Day 8 | 7.3 (±1.4) | 6.6 (±0.4) | 7.6 (±0.4) |

[1]Error is standard deviation of multiple measurement.

The data in Table 6 show that under these circumstances, miR-34a, b, and c levels were induced from about 7 to 8-fold in p53 activated cells, demonstrating regulation of miR-34a, b, and c levels by TP53 in mice, in vivo.

EXAMPLE 6

This Example demonstrates that the introduction of synthetic miR-34 into human cells elicits a phenotype similar to that induced by activation of the TP53 G1 checkpoint.

Rationale:

Delay of the G1/S transition of the cell cycle is known to be a consequence of TP53 activation. In this example, miR-34 siRNA duplexes were designed with passenger strands that are complementary to the natural mature miRNA, except for a single base mismatch four bases from the 3' end of the sequence, referred to as "asymmetric passenger strands". Exemplary asymmetric passenger strands are provided in Table 7 for miR-34a (SEQ ID NO:12); for miR-34b (SEQ ID NO:17), and for miR-34c (SEQ ID NO: 22), with the mismatch underlined. As shown in Table 7, these synthetically designed asymmetric passenger strands differ from the corresponding natural passenger strands for miR-34a (SEQ ID NO:35), miR-34b (SEQ ID NO:36) and miR-34c (SEQ ID NO:37).

As described in Example 10, it was determined that an siRNA duplex miR-34 mimetic sequence containing annealed strands of SEQ ID NO:1 and asymmetric passenger strand SEQ ID NO:12 was more effective in inducing a cell death phenotype than annealed natural miR-34 guide strand (SEQ ID NO:1) and natural miR-34 passenger strand (SEQ ID NO:35). While not wishing to be bound by theory, it is believed that the presence of the mismatch in the passenger strand destabilizes the duplex in that region and thereby facilitates entry into RISC of the strand mimicking mature miR-34. The duplex miR-34 mimetic sequence with the asymmetric passenger strand and natural guide strand is processed resulting in formation of the mature wild type miR-34 guide strand.

The data presented in this example show that introduction of such duplex miR-34 mimetics into cells leads to cell cycle arrest at the G1 checkpoint in a manner that is analogous to activation of TP53.

Methods:

A549 cells were transfected with synthetic miR-34a, b, and c synthetic RNA duplexes, as well as mutated control versions of each. Twenty four hours post transfection, the cells were treated with Nocodazole (100 ng/ml) for 16-20 hours. The percentage of cells arrested at the G1 stage of the cell cycle was measured using propidium iodide staining and flow cytometry. All synthetic oligonucleotides (Table 7) were obtained from Sigma-Proligo (St. Louis, Mo.).

TABLE 7

Synthetic miR-34 Oligonucleotide Sequences

| siRNA, miRNA or mismatch miRNA | Guide strand/mature (5' to 3') | SEQ ID NO: | Passenger strand (5' to 3') | SEQ ID NO: |
|---|---|---|---|---|
| miR-34a | UGGCAGUGUCUUAGCUGGUUGU (natural) | 1 | CAAUCAGCAAGUAUACUGCCCU (natural) | 35 |
| miR-34a | UGGCAGUGUCUUAGCUGGUUGU (natural) | 1 | AACCAGCUAAGACACUGCGAAU (synthetic: reverse complement of natural guide strand with one base mismatch) | 12 |
| miR-34a-mm2,3 | UCCCAGUGUCUUAGCUGGUUGU (mutation in seed region) | 13 | AACCAGCUAAGACACUGGCAAU (synthetic: reverse complement of seed region mutation with one base mismatch) | 14 |
| miR-34a-mm18,19 | UGGCAGUGUCUUAGCUGCAUGU (mutation in non-seed region) | 15 | AUGCAGCUAAGACACUGCGAAU (synthetic: reverse complement of non-seed region mutation with one base mismatch) | 16 |
| miR-34b | AGGCAGUGUCAUUAGCUGAUUG (natural) | 4 | CAAUCACUAACUCCACUGCCAU (natural) | 36 |
| miR-34b | AGGCAGUGUCAUUAGCUGAUUG (natural) | 4 | AUCAGCUAAUGACACUGCGUAU (synthetic: reverse complement of natural guide strand with one base mismatch) | 17 |
| miR-34b-mm2,3 | ACCCAGUGUCAUUAGCUGAUUG (mutation in seed region) | 18 | AUCAGCUAAUGACACUGGCUAU (synthetic: reverse complement of seed region mutation with one base mismatch) | 19 |
| miR-34b-mm18,19 | AGGCAGUGUCAUUAGCUCUUUG (mutation in non-seed region) | 20 | AAGAGCUAAUGACACUGCGUAU (synthetic: reverse complement of non-seed region mutation with one base mismatch) | 21 |
| miR-34c | AGGCAGUGUAGUUAGCUGAUUG (natural) | 7 | AAUCACUAACCACACGGCCAGG (natural) | 37 |
| miR-34c | AGGCAGUGUAGUUAGCUGAUUG (natural) | 7 | AUCAGCUAACUACACUGCGUAU (synthetic: reverse complement of natural guide strand with one base mismatch) | 22 |
| miR-34c-mm2,3 | ACCCAGUGUAGUUAGCUGAUUG (mutation in seed region) | 23 | AUCAGCUAACUACACUGGCUAU (synthetic: reverse complement of seed region mutation with one base mismatch) | 24 |
| miR-34c-mm18,19 | AGGCAGUGUAGUUAGCUCUUUG (mutation in non-seed region) | 25 | AAGAGCUAACUACACUGCGUAU (synthetic: reverse complement of non-seed region mutation with one base mismatch) | 26 |

TABLE 8

Cell Cycle Arrest in A549 Cells (wild type p53) Transfected with Synthetic miR-34 Constructs

| microRNA species introduced into A549 cells | Guide strand/passenger strand | % Cells in G1 |
|---|---|---|
| miR34a (WT mature) | SEQ ID NO: 1/SEQ ID NO: 12 | 43.3% |
| miR34a-mm18,19 (non-seed mismatch) | SEQ ID NO: 15/SEQ ID NO: 16 | 36.0% |
| miR34a-mm2,3 (seed mismatch) | SEQ ID NO: 13/SEQ ID NO: 14 | 20.4% |
| miR34b (WT mature) | SEQ ID NO: 4/SEQ ID NO: 17 | 67.7% |
| miR34b-mm18,19 (non-seed mismatch) | SEQ ID NO: 20/SEQ ID NO: 21 | 60.6% |
| miR34b-mm2,3 (seed mismatch) | SEQ ID NO: 18/SEQ ID NO: 19 | 19.8% |
| miR34c (WT mature) | SEQ ID NO: 7/SEQ ID NO: 22 | 67.6% |
| miR34c-mm18,19 (non-seed mismatch) | SEQ ID NO: 25/SEQ ID NO: 26 | 60.5% |
| miR34c-mm2,3 (seed mismatch) | SEQ ID NO: 23/SEQ ID NO: 24 | 21.2% |

Table 8 shows A549 cells having a normal level of TP53 function (wild type p53) that were either transfected with a normal synthetic miR-34a RNA duplex (wild type mature) comprising a guide strand [SEQ ID NO:1] and a passenger strand [SEQ ID NO:12] with a single nucleotide mismatch; transfected with a non-seed region double mutant synthetic miR-34a(18,19) RNA duplex comprising a guide strand [SEQ ID NO:15] and a passenger strand [SEQ ID NO:16]; or transfected with a seed region double mutant synthetic miR-34a(2,3) RNA duplex comprising a guide strand [SEQ ID NO:13] and a passenger strand [SEQ ID NO:14].

Table 8 further shows A549 cells having a normal level of TP53 function (wild type p53) that were either transfected with a normal synthetic miR-34b RNA duplex (wild type mature) comprising a guide strand [SEQ ID NO:4] and a passenger strand [SEQ ID NO:17] with a single nucleotide mismatch; transfected with a non-seed region double mutant synthetic miR-34b(18,19) RNA duplex comprising a guide strand [SEQ ID NO:20] and a passenger strand [SEQ ID NO:21]; or transfected with a seed region double mutant synthetic miR-34b(2,3) RNA duplex comprising a guide strand [SEQ ID NO:18] and a passenger strand [SEQ ID NO:19].

Table 8 further shows A549 cells having a normal level of TP53 function (wild type p53) that were either transfected with a normal synthetic miR-34c RNA duplex (wild type mature) comprising a guide strand [SEQ ID NO:7] and a passenger strand [SEQ ID NO:22] with a single nucleotide mismatch; transfected with a non-seed region double mutant synthetic miR-34b(18,19) RNA duplex comprising a guide strand [SEQ ID NO:25] and a passenger strand [SEQ ID NO:26]; or transfected with a seed region double mutant synthetic miR-34c(2,3) RNA duplex comprising a guide strand [SEQ ID NO:23] and a passenger strand [SEQ ID NO:24].

The data provided in Table 8 shows that introduction of synthetic miR-34a, miR-34b, and miR-34c RNA duplexes (wild type mature), as well as double mutant RNA duplexes miR-34a(18,19), miR-34b(18,19), and miR-34c(18,19), that have mutations outside of the seed region, induce a G1 cell cycle arrest in a cell having a normal level of TP53 function.

RNA duplexes miR-34a(2,3), miR-34b(2,3), and miR-34c(2, 3), that have double mutations in the seed region, do not induce such a cell cycle arrest. Thus, each of the synthetic miR-34a, miR-34b, and miR-34c siRNA constructs that have a corresponding intact seed region, can elicit a phenotype reflective of the TP53-mediated DNA damage checkpoint.

It was also observed that the cell cycle arrest phenotype induced by introduction of miR-34a or miR-34a(18-19), miR34b or miR34b(18-19), or miR34c or miR34c(18-19) is dependent on TP53 function. Delivery of the same set of miR-34a synthetic siRNA constructs (Table 7) to A549 cells stably expressing a TP53 shRNA construct that silences TP53 to about 5% of the levels in control A549 cells did not result in the cell cycle arrest phenotype (data not shown).

EXAMPLE 7

This Example demonstrates that transcripts regulated by miR-34 overlap with TP53 pathway genes.

Methods:

To better understand the function of the miR-34 family, gene expression profiling experiments were performed. RNA duplexes corresponding to miR-34a, miR-34b, miR-34c, or a control target luciferase (Luc) were transfected into A549, HCT116 Dicer$^{ex5}$, TOV21G, DLD-1 Dicer$^{ex5}$ cells. The guide strand of the luciferase siRNA used in these experiments was: 5' CGUACGCGGAAUACUUCGAdTdT 3' [SEQ ID NO:27], and the passenger strand of the luciferase siRNA was 5' UCGAAGUAUUCCGUACGdTdT 3 [SEQ ID NO:28] (purchased from Sigma-Proligo). The miR-34a, miR-34b, and miR-34c siRNA duplexes used in these experiments are set forth in Table 7 of Example 6.

HCT116 cells were transfected in 6-well plates by using Lipofectamine 2000 (Invitrogen, Carlsbad, Calif.). DLD-1, TOV21G, and A549 cells were transfected using SilentFect (Bio-Rad, Hercules, Calif.). Duplexes were used at final concentrations of 100 nM for all cell lines. Total RNA was isolated 24 hours post transfection, and subjected to microarray expression analysis as described by Jackson et al. (2003 *Nat. Biotechnol.* 21:635-37). Microarray profiling of cells transfected with the miR-34a, b, and c-like siRNA sequences were used to identify the direct targets of the miR-34 microRNAs, as well as their downstream effects.

Results:

Analysis of the microarray gene expression profiles (data not shown) identified a cluster of genes that were specifically down-regulated at 24 hours post-transfection as shown in Table 9 below. Genes down-regulated by miR-34 were highly enriched for transcripts containing 3'UTRs complementary to the miR-34 seed region hexamers. MicroRNA-regulated transcripts were identified in microarray gene expression signatures using a P-value cut-off ($P<0.01$). miRNA down-regulated transcripts were defined by the intersection of down-regulated transcripts in all the lines tested. Down-regulated transcripts were tested for enrichment relative to a background set using the hypergeometric distribution. miRNA target regulation was measured by enrichment of transcripts containing miRNA hexamer seed strings (stretches of 6 contiguous bases complementary to miRNA seed region nucleotide positions 1-6, 2-7, or 3-8) in transcripts having annotated 3'UTRs.

TABLE 9

Expression alterations for miR-34 down-regulated genes in HCT116 Dicer Ex5 cells.

| Gene Names | Genbank Accession #[b] | Luc siRNA | mir-34a | mir-34b | mir-34c |
|---|---|---|---|---|---|
| TK1 | NM_003258 | 1.09 | 3.65 | 3.22 | 3.02 |
| PHF19 | AL117477 | 1.01 | 3.31 | 2.40 | 2.99 |
| MET | AK025784 | 1.64 | 3.24 | 3.16 | 2.88 |
| LOC149832 | BC044234 | 1.29 | 3.06 | 2.61 | 2.42 |
| MCM3 | NM_002388 | 1.21 | 3.03 | 2.86 | 3.27 |
| FLJ11029 | AW183918 | -1.14 | 2.97 | 2.02 | 1.99 |
| SH3GL1 | NM_003025 | 1.47 | 2.97 | 2.44 | 2.25 |
| FGFRL1 | NM_021923 | 1.08 | 2.94 | 3.04 | 3.09 |
| CHES1 | NM_005197 | 1.34 | 2.79 | 2.58 | 2.50 |
| PPP1R11 | NM_021959 | 1.10 | 2.75 | 2.31 | 2.29 |
| MGC5508 | NM_024092 | 1.25 | 2.75 | 2.91 | 2.86 |
| CDK4 | NM_052984 | 1.07 | 2.74 | 2.39 | 2.29 |
| C1orf19 | NM_052965 | -1.01 | 2.72 | 2.50 | 2.57 |
| NUP210 | NM_024923 | 1.01 | 2.71 | 1.86 | 1.75 |
| RAB21 | BC009109 | -1.03 | 2.70 | 1.89 | 1.57 |
| SLC35A4 | NM_080670 | 1.08 | 2.70 | 1.99 | 1.87 |
| NASP | NM_172164 | 1.19 | 2.68 | 2.56 | 2.73 |
| ANKRD40 | AK054795 | 1.04 | 2.68 | 2.04 | 2.20 |
| MGC5242 | AK056910 | -1.11 | 2.67 | 2.34 | 2.33 |
| SGPP1 | AI762918 | -1.01 | 2.64 | 1.87 | 1.84 |
| LMAN2L | NM_030805 | -1.06 | 2.64 | 2.54 | 2.60 |
| ULBP2 | NM_025217 | 1.42 | 2.62 | 2.54 | 3.09 |
| FKSG24 | NM_032683 | 1.04 | 2.61 | 2.00 | 2.00 |
| CNOT6 | NM_015455 | -1.10 | 2.59 | 1.68 | 1.66 |
| CAP1 | NM_006367 | -1.00 | 2.59 | 1.86 | 1.63 |
| MGC16207 | BC007379 | 1.18 | 2.57 | 2.54 | 2.47 |
| FLJ11029 | NM_018304 | -1.22 | 2.57 | 1.93 | 2.02 |
| E2F2 | AF086395 | 1.31 | 2.57 | 1.93 | 2.20 |
| TPD52 | NM_005079 | 1.02 | 2.56 | 1.82 | 1.85 |
| TTC19 | NM_017775 | 1.03 | 2.56 | 2.05 | 2.24 |
| GLRX5 | NM_016417 | -1.04 | 2.50 | 1.98 | 1.81 |
| MYB | NM_005375 | 1.32 | 2.50 | 1.90 | 2.17 |
| ATG9A | NM_024085 | 1.04 | 2.48 | 1.81 | 1.93 |
| VAMP2 | NM_014232 | 1.02 | 2.45 | 1.97 | 2.52 |
| SLC29A1 | NM_004955 | 1.24 | 2.45 | 1.71 | 1.80 |
| FAM64A | NM_019013 | -1.11 | 2.44 | 1.97 | 1.96 |
| CDCA5 | NM_080668 | 1.15 | 2.44 | 2.12 | 2.29 |
| CDC25A | AI343459 | 1.03 | 2.40 | 2.04 | 2.20 |
| FURIN | NM_002569 | -1.08 | 2.39 | 1.74 | 1.68 |
| DTL | NM_016448 | 1.23 | 2.39 | 2.82 | 3.32 |
| TMED8 | AK095650 | -1.08 | 2.38 | 2.63 | 2.50 |
| SHCBP1 | NM_024745 | -1.05 | 2.38 | 2.72 | 2.96 |
| TRIB3 | NM_021158 | 1.08 | 2.37 | 1.86 | 1.88 |
| MET | NM_000245 | 1.29 | 2.36 | 2.57 | 2.27 |
| RKHD2 | NM_016626 | -1.05 | 2.36 | 2.47 | 2.43 |
| GMNN | NM_015895 | -1.08 | 2.35 | 2.08 | 2.09 |
| ARHGAP1 | NM_004308 | 1.71 | 2.34 | 1.96 | 1.99 |
| PKMYT1 | NM_004203 | 1.16 | 2.31 | 1.73 | 1.99 |
| MGC13170 | NM_032712 | 1.15 | 2.31 | 1.56 | 1.65 |
| C6orf89 | AJ420511 | 1.06 | 2.31 | 2.53 | 2.29 |
| TSPAN14 | NM_030927 | 1.10 | 2.30 | 1.54 | 1.37 |
| FLJ13912 | NM_022770 | 1.05 | 2.25 | 2.19 | 2.35 |
| CDK6 | AI333092 | 1.08 | 2.25 | 2.36 | 1.80 |
| MAP3K11 | NM_002419 | -1.06 | 2.23 | 1.78 | 1.82 |
| CTDSPL | NM_005808 | 1.21 | 2.23 | 2.24 | 2.74 |
| CDS2 | AI972315 | 1.05 | 2.22 | 1.89 | 1.92 |
| SLC44A2 | NM_020428 | 1.05 | 2.22 | 2.08 | 1.97 |
| TGIF2 | NM_021809 | 1.05 | 2.22 | 2.30 | 2.43 |
| MYOHD1 | NM_025109 | 1.00 | 2.21 | 1.61 | 1.83 |
| CTDSP2 | NM_005730 | -1.03 | 2.21 | 1.66 | -2.00 |
| SURF4 | NM_033161 | 1.26 | 2.19 | 1.93 | 1.82 |
| YKT6 | NM_006555 | 1.02 | 2.19 | 1.71 | 1.62 |
| CDC23 | NM_004661 | 1.14 | 2.19 | 1.76 | 1.76 |
| GNPDA1 | NM_005471 | 1.45 | 2.18 | 1.71 | 1.48 |
| NAGPA | NM_016256 | 1.03 | 2.17 | 1.85 | 2.07 |
| RDH11 | NM_016026 | 1.11 | 2.14 | 1.73 | 1.61 |
| IMPDH1 | NM_000883 | 1.23 | 2.13 | 1.77 | 1.67 |
| SPBC25 | NM_020675 | -1.12 | 2.12 | 2.09 | 1.94 |
| SPFH1 | NM_006459 | -1.00 | 2.11 | 2.48 | 2.54 |
| PHGDH | NM_006623 | 1.21 | 2.10 | 2.38 | 2.17 |
| CHES1 | NM_018589 | 1.13 | 2.09 | 2.18 | 2.22 |
| CCNE2 | NM_057749 | 1.42 | 2.08 | 2.08 | 2.34 |
| XBP1 | NM_005080 | 1.18 | 2.07 | 2.04 | 1.99 |
| RAD54L | NM_003579 | 1.07 | 2.06 | 1.85 | 2.29 |
| RDX | NM_002906 | -1.03 | 2.05 | 1.75 | 1.95 |
| FLJ14154 | NM_024845 | 1.68 | 2.04 | 2.01 | 2.01 |
| SIX5 | NM_175875 | 1.07 | 2.03 | 1.82 | 1.98 |
| FANCA | NM_000135 | 1.11 | 2.03 | 1.70 | 2.22 |
| KIAA1333 | NM_017769 | 1.13 | 2.03 | 1.59 | 1.66 |
| C8orf55 | NM_016647 | -1.07 | 2.03 | 1.83 | 1.74 |
| MGC21644 | NM_182960 | -1.30 | 2.02 | 1.75 | 2.20 |
| TMEM48 | NM_018087 | -1.06 | 2.02 | 1.81 | 1.74 |
| FANCG | NM_004629 | -1.02 | 2.01 | 1.61 | 1.84 |
| CPSF6 | NM_007007 | 1.04 | 2.01 | 2.08 | 2.45 |
| CCNE2 | NM_004702 | 1.26 | 2.01 | 2.08 | 2.39 |
| MCM5 | NM_006739 | 1.09 | 2.01 | 1.56 | 1.69 |
| CTDSP1 | NM_021198 | -1.00 | 2.00 | 1.69 | 1.86 |
| DKFZp564K142 | NM_032121 | -1.26 | 2.00 | 1.96 | 2.31 |
| AXL | NM_001699 | 1.03 | 1.99 | 1.61 | 1.87 |
| KIAA0101 | NM_014736 | -1.19 | 1.99 | 1.59 | 1.56 |
| STMN1 | NM_005563 | -1.04 | 1.98 | 2.13 | 2.11 |
| TAF5 | NM_139052 | -1.07 | 1.98 | 2.01 | 2.11 |
| MBD3 | AL390153 | 1.08 | 1.97 | 1.86 | 1.89 |
| FBXO10 | BC013747 | -1.24 | 1.97 | 1.43 | 1.69 |
| C7orf21 | NM_031434 | -1.14 | 1.95 | 1.73 | 1.93 |
| HMMR | NM_012484 | -1.22 | 1.95 | 2.28 | 2.44 |
| UBE2L3 | NM_003347 | 1.26 | 1.95 | 1.69 | 1.54 |
| SGPP1 | NM_030791 | -1.20 | 1.94 | 1.68 | 1.53 |
| MYBL2 | NM_002466 | 1.03 | 1.94 | 1.87 | 2.08 |
| RPAP1 | NM_015540 | 1.20 | 1.93 | 1.95 | 2.03 |
| MGC5242 | NM_024033 | -1.12 | 1.93 | 1.98 | 2.11 |
| LASS2 | NM_022075 | 1.27 | 1.92 | 1.78 | 1.92 |
| VPS4A | NM_013245 | -1.05 | 1.92 | 1.92 | 1.95 |
| ZDHHC16 | NM_032327 | -1.05 | 1.92 | 1.62 | 1.46 |
| LRRC40 | NM_017768 | -1.16 | 1.92 | 1.82 | 1.86 |
| C9orf140 | NM_178448 | -1.01 | 1.91 | 1.64 | 1.61 |
| WDR76 | AI220472 | 1.10 | 1.91 | 1.83 | 2.08 |
| MGC23280 | NM_144683 | 1.08 | 1.91 | 1.45 | 1.52 |
| UNC84B | NM_015374 | 1.02 | 1.91 | 1.69 | 1.56 |
| VCL | NM_003373 | -1.13 | 1.90 | 1.61 | 1.68 |
| SNX15 | NM_013306 | 1.05 | 1.89 | 1.73 | 1.80 |
| ARAF | NM_001654 | 1.15 | 1.89 | 1.58 | 1.59 |
| C20orf100 | NM_032883 | 1.04 | 1.89 | 1.54 | 1.60 |
| CUEDC1 | AI936146 | 1.23 | 1.89 | 1.69 | 1.90 |
| BRCA1 | NM_007300 | 1.02 | 1.88 | 2.31 | 2.67 |
| SFRS1 | AI589112 | 1.10 | 1.88 | 1.53 | 1.73 |
| TSN | NM_004622 | -1.12 | 1.87 | 1.88 | 1.71 |
| CUEDC1 | NM_017949 | 1.18 | 1.85 | 1.66 | 1.78 |
| GAS2L3 | NM_174942 | -1.01 | 1.85 | 1.39 | 1.41 |
| ZNF358 | NM_018083 | 1.02 | 1.84 | 1.66 | 1.56 |
| HTLF | AA827684 | 1.20 | 1.84 | 2.12 | 2.01 |
| SCRIB | NM_015356 | 1.06 | 1.83 | 1.63 | 1.81 |
| DKFZP564O0823 | AK025205 | 1.17 | 1.83 | 3.17 | 3.23 |
| GSG2 | NM_031965 | -1.12 | 1.83 | 2.08 | 2.27 |
| WDR62 | NM_015671 | 1.04 | 1.82 | 1.59 | 1.95 |
| GOLPH3L | NM_018178 | -1.03 | 1.82 | 2.18 | 2.14 |
| PER2 | NM_022817 | -1.04 | 1.82 | 1.28 | 1.19 |
| FEN1 | NM_004111 | -1.11 | 1.81 | 2.05 | 2.20 |
| ERO1L | AK024224 | 1.36 | 1.81 | 1.83 | 1.94 |
| CD151 | NM_004357 | 1.13 | 1.81 | 1.65 | 1.58 |
| C6orf89 | AK001957 | -1.09 | 1.81 | 2.05 | 2.08 |
| ZNF395 | NM_017606 | 1.00 | 1.80 | 2.26 | 2.02 |
| HMGN4 | NM_006353 | -1.08 | 1.80 | 2.92 | 2.88 |
| EME1 | NM_152463 | -1.05 | 1.79 | 1.79 | 2.26 |
| RP13-15M17.2 | AI953008 | 1.08 | 1.79 | 1.88 | 1.80 |
| CIC | NM_015125 | 1.05 | 1.79 | 1.47 | 1.53 |
| MBD3 | NM_003926 | 1.15 | 1.78 | 1.36 | 1.46 |
| KIAA1704 | AB051491 | -1.06 | 1.78 | 1.30 | 1.41 |
| AXL | NM_021913 | 1.00 | 1.78 | 1.59 | 1.75 |
| PSF1 | D80008 | -1.16 | 1.78 | 1.81 | 1.99 |
| BRRN1 | NM_015341 | 1.04 | 1.78 | 1.69 | 1.84 |
| SLC45A3 | NM_033102 | 1.25 | 1.77 | 1.55 | 1.73 |
| CASKIN2 | NM_020753 | 1.14 | 1.77 | 1.55 | 1.60 |

TABLE 9-continued

Expression alterations for miR-34 down-regulated genes in HCT116 Dicer Ex5 cells.

| Gene Names | Genbank Accession #[b] | Luc siRNA | mir-34a | mir-34b | mir-34c |
|---|---|---|---|---|---|
| CHAF1A | NM_005483 | 1.13 | 1.77 | 1.65 | 1.96 |
| RASSF5 | NM_031437 | 1.07 | 1.77 | 1.83 | 2.05 |
| F8 | NM_019863 | −1.13 | 1.77 | 1.57 | 1.42 |
| MGC12538 | AA703254 | 1.39 | 1.76 | 1.56 | 1.24 |
| C9orf125 | AJ420439 | 1.02 | 1.76 | 2.10 | 2.09 |
| RAD51 | NM_002875 | 1.16 | 1.76 | 1.58 | 1.77 |
| HDAC1 | NM_004964 | −1.07 | 1.76 | 1.96 | 1.96 |
| NFYC | NM_014223 | −1.04 | 1.76 | 1.73 | 1.97 |
| HIST1H4E | NM_003545 | 1.07 | 1.75 | 1.66 | 1.83 |
| PLK1 | NM_005030 | 1.15 | 1.75 | 1.61 | 1.68 |
| PTP4A2 | NM_080391 | 1.23 | 1.74 | 2.29 | 2.60 |
| LOC159090 | AL832218 | −1.08 | 1.74 | 1.86 | 2.00 |
| TOM1L2 | AL133641 | 1.01 | 1.74 | 1.45 | 1.42 |
| FEM1A | NM_018708 | 1.00 | 1.74 | 1.42 | 1.26 |
| TESK1 | NM_006285 | −1.03 | 1.74 | 1.67 | 1.87 |
| UBE2Q1 | NM_017582 | 1.18 | 1.74 | 2.24 | 2.38 |
| ESPL1 | NM_012291 | −1.03 | 1.74 | 1.56 | 1.61 |
| RRM2 | BC028932 | 1.05 | 1.74 | 2.05 | 2.32 |
| SCMH1 | NM_012236 | 1.10 | 1.74 | 1.76 | 2.04 |
| SFXN5 | NM_144579 | 1.02 | 1.73 | 1.76 | 1.90 |
| MTA2 | NM_004739 | 1.19 | 1.73 | 1.56 | 1.54 |
| SURF5 | NM_006752 | 1.04 | 1.73 | 1.47 | 1.64 |
| SLC16A4 | AK091279 | 1.04 | 1.73 | 1.49 | 1.69 |
| FUT8 | NM_004480 | −1.03 | 1.73 | 1.76 | 1.75 |
| DTYMK | NM_012145 | −1.01 | 1.72 | 1.35 | 1.43 |
| ATP1B3 | NM_001679 | 1.00 | 1.72 | 1.77 | 1.64 |
| SPBC24 | NM_182513 | −1.09 | 1.72 | 1.46 | 1.68 |
| FLJ37034 | BC047423 | −1.01 | 1.72 | 1.79 | 1.98 |
| FLJ13868 | NM_022744 | 1.02 | 1.72 | 1.48 | 1.47 |
| BCL2 | NM_000633 | −1.03 | 1.72 | 1.46 | 1.44 |
| CKLF | AI077541 | −1.08 | 1.72 | 1.49 | 1.58 |
| C10orf38 | AL050367 | 1.05 | 1.71 | 1.45 | 1.46 |
| CABLES2 | BC003122 | −1.16 | 1.71 | 1.61 | 1.69 |
| FLJ39827 | NM_152424 | 1.38 | 1.71 | 1.47 | 1.39 |
| MDM4 | NM_002393 | −1.16 | 1.71 | 1.34 | 1.44 |
| FAM100B | NM_182565 | −1.10 | 1.71 | 1.64 | 1.69 |
| ZDHHC12 | NM_032799 | 1.05 | 1.71 | 1.50 | 1.40 |
| KIAA1160 | NM_020701 | −1.12 | 1.71 | 1.45 | 1.49 |
| ACSL4 | NM_022977 | −1.01 | 1.71 | 2.06 | 2.04 |
| ZHX2 | NM_014943 | 1.09 | 1.71 | 1.70 | 1.60 |
| KIF11 | NM_004523 | −1.04 | 1.71 | 1.59 | 1.69 |
| GTSE1 | NM_016426 | 1.02 | 1.70 | 1.63 | 1.76 |
| DDX10 | NM_004398 | 1.18 | 1.70 | 1.49 | 1.35 |
| NQO1 | NM_000903 | 0.00 | 1.70 | 2.93 | 2.27 |
| ORC1L | NM_004153 | 1.11 | 1.70 | 1.91 | 2.32 |
| PURB | AK057669 | 1.08 | 1.70 | 1.79 | 1.80 |
| FLJ14166 | NM_024565 | −1.10 | 1.69 | 1.77 | 1.90 |
| TBC1D13 | NM_018201 | 1.15 | 1.69 | 1.49 | 1.86 |
| PMF1 | NM_007221 | 1.05 | 1.69 | 1.75 | 1.69 |
| IFRD2 | NM_006764 | 1.02 | 1.69 | 1.87 | 2.01 |
| AFG3L1 | NM_001132 | −1.19 | 1.68 | 1.63 | 2.19 |
| CEP55 | NM_018131 | −1.22 | 1.68 | 1.48 | 1.52 |
| MKI67 | NM_002417 | −1.16 | 1.68 | 1.58 | 1.40 |
| PLAGL2 | NM_002657 | 1.04 | 1.68 | 1.50 | 1.67 |
| VCL | NM_014000 | −1.18 | 1.68 | 1.48 | 1.58 |
| ARHGDIB | NM_001175 | −1.11 | 1.68 | 1.58 | 1.87 |
| UBE2C | NM_181802 | −1.03 | 1.68 | 1.43 | 1.50 |
| KCNS3 | NM_002252 | −1.08 | 1.68 | 1.72 | 1.59 |
| CCDC15 | NM_025004 | −1.03 | 1.67 | 1.46 | 1.60 |
| LASS5 | NM_147190 | −1.03 | 1.67 | 1.66 | 1.63 |
| PALLD | NM_016081 | 1.02 | 1.67 | 1.41 | 1.28 |
| AREG | NM_001657 | 1.56 | 1.67 | 1.62 | 1.35 |
| PTTG3 | NM_021000 | 0.00 | 1.66 | 1.47 | 1.51 |
| BIRC5 | NM_001168 | −1.18 | 1.66 | 1.89 | 1.98 |
| UBE2C | NM_007019 | −1.05 | 1.66 | 1.42 | 1.52 |
| ABR | NM_001092 | 1.25 | 1.66 | 1.39 | 1.56 |
| ZNF580 | NM_016202 | 1.05 | 1.66 | 1.60 | 1.54 |
| PHF17 | NM_024900 | 1.02 | 1.65 | 1.48 | 1.49 |
| NMT1 | NM_021079 | 1.03 | 1.65 | 2.44 | 2.58 |
| PHB | NM_002634 | 1.08 | 1.65 | 1.45 | 1.44 |
| Pfs2 | NM_016095 | 1.16 | 1.65 | 1.53 | 1.74 |
| NDP52 | NM_005831 | −1.01 | 1.65 | 1.42 | 1.30 |
| DKFZp762E1312 | NM_018410 | 1.03 | 1.65 | 1.51 | 1.78 |
| C9orf10OS | AK056096 | −1.06 | 1.64 | 1.45 | 1.62 |
| DDX11 | NM_004399 | −1.01 | 1.64 | 1.53 | 2.14 |
| GCH1 | NM_000161 | 1.35 | 1.64 | 1.70 | 1.61 |
| RNF38 | NM_022781 | −1.08 | 1.64 | 1.47 | 1.32 |
| FSHPRH1 | AI190209 | −1.01 | 1.64 | 1.75 | 2.07 |
| LOC388730 | AI420422 | 1.14 | 1.64 | 1.39 | 1.37 |
| PARP16 | NM_017851 | 1.10 | 1.64 | 2.04 | 2.20 |
| MAPK9 | AI096774 | 1.03 | 1.64 | 1.54 | 1.53 |
| C14orf94 | NM_017815 | 1.02 | 1.63 | 1.41 | 1.50 |
| MPP2 | NM_005374 | 1.07 | 1.63 | 1.73 | 1.43 |
| FAM49B | AA497060 | 1.35 | 1.63 | 1.83 | 1.84 |
| HPCAL4 | NM_016257 | −1.07 | 1.63 | 1.96 | 2.02 |
| WHSC1 | NM_133336 | 1.50 | 1.63 | 1.99 | 2.25 |
| C15orf21 | NM_173609 | 1.07 | 1.63 | 1.53 | 1.53 |
| MFN2 | NM_014874 | 1.03 | 1.63 | 1.50 | 1.29 |
| LOC146517 | AL833385 | −1.04 | 1.62 | 1.45 | 1.62 |
| ORC6L | NM_014321 | 1.17 | 1.62 | 1.51 | 1.71 |
| QDPR | NM_000320 | −1.00 | 1.62 | 1.72 | 1.70 |
| POLQ | NM_006596 | −1.01 | 1.62 | 1.46 | 1.67 |
| KIF15 | NM_020242 | −1.00 | 1.62 | 1.92 | 2.13 |
| GRPEL2 | NM_152407 | 1.04 | 1.62 | 1.89 | 1.98 |
| FLJ20255 | NM_017728 | 1.13 | 1.62 | 1.46 | 1.61 |
| ZNF395 | NM_018660 | 1.03 | 1.61 | 1.81 | 1.69 |
| HMGB3 | NM_005342 | −1.03 | 1.61 | 1.77 | 1.88 |
| UBP1 | NM_014517 | 1.06 | 1.61 | 2.08 | 2.20 |
| WHSC1 | NM_133330 | 1.32 | 1.61 | 2.10 | 2.28 |
| TATDN2 | NM_014760 | 1.06 | 1.61 | 1.77 | 1.83 |
| HIRIP3 | NM_003609 | 1.11 | 1.61 | 1.39 | 1.44 |
| ZNF551 | NM_138347 | 1.00 | 1.60 | 1.33 | 1.51 |
| TUBA2 | NM_006001 | 1.04 | 1.60 | 1.39 | 1.31 |
| ATPAF1 | AL137294 | −1.20 | 1.60 | 1.59 | 1.39 |
| RANBP10 | AB040897 | −1.02 | 1.60 | 1.57 | 1.75 |
| MAC30 | NM_014573 | 1.06 | 1.59 | 1.42 | 1.44 |
| HIP2 | AL117568 | −1.05 | 1.59 | 2.11 | 2.06 |
| CAV1 | AF074993 | 1.23 | 1.59 | 1.52 | 1.60 |
| EXOSC2 | NM_014285 | 1.19 | 1.59 | 1.51 | 1.65 |
| ASXL1 | NM_015338 | 1.01 | 1.59 | 1.60 | 1.77 |
|  | AI890133 | −1.07 | 1.59 | 1.48 | 1.29 |
| KIAA1160 | AK024035 | 1.05 | 1.59 | 1.28 | 1.39 |
| TUBAP | NG_000900 | 1.08 | 1.59 | 1.35 | 1.36 |
| MED8 | NM_052877 | 1.01 | 1.59 | 1.80 | 1.91 |
| CDK6 | AK000660 | −1.26 | 1.58 | 1.99 | 1.85 |
| KIFC1 | NM_002263 | −1.01 | 1.58 | 1.56 | 1.96 |
| RP13-360B22.2 | NM_032227 | 1.02 | 1.58 | 1.73 | 1.80 |
| EXO1 | NM_130398 | 1.07 | 1.58 | 1.45 | 1.65 |
| EFNA5 | AW015347 | 1.11 | 1.58 | 1.85 | 1.83 |
| CCND3 | NM_001760 | −1.13 | 1.58 | 1.68 | 1.83 |
| MAP2K1 | NM_002755 | −1.14 | 1.57 | 1.96 | 2.23 |
| FAM76A | AI805069 | −1.10 | 1.57 | 1.39 | 1.57 |
| C9orf25 | NM_147202 | −1.17 | 1.57 | 1.48 | 1.69 |
|  | W93501 | −1.13 | 1.56 | 1.56 | 1.65 |
| BARD1 | NM_000465 | 1.15 | 1.56 | 1.42 | 1.83 |
| ADRBK2 | BC029563 | −1.05 | 1.56 | 1.59 | 1.50 |
| CDC25C | NM_001790 | 1.01 | 1.56 | 1.37 | 1.40 |
| FLJ20232 | NM_019008 | 1.03 | 1.56 | 1.88 | 1.84 |
| POU2F1 | BC037864 | 1.15 | 1.56 | 1.93 | 1.64 |
| NDRG1 | NM_006096 | 1.29 | 1.56 | 2.03 | 2.03 |
| PSMB7 | AJ420421 | 1.04 | 1.56 | 1.34 | 1.32 |
| D4ST1 | NM_130468 | 1.02 | 1.56 | 1.79 | 1.85 |
| CCNF | NM_001761 | 1.01 | 1.56 | 1.61 | 1.76 |
| CDKN3 | NM_005192 | −1.34 | 1.56 | 1.40 | 1.30 |
| PRR3 | NM_025263 | −1.20 | 1.55 | 1.39 | 1.48 |
| FADS2 | NM_004265 | 1.11 | 1.55 | 1.51 | 1.62 |
| FANCE | NM_021922 | 1.03 | 1.55 | 1.25 | 1.37 |
| CAV1 | NM_001753 | 1.26 | 1.55 | 1.45 | 1.34 |
| SAMD6 | NM_173551 | 1.05 | 1.54 | 1.55 | 1.59 |
| BID | AK057062 | 1.03 | 1.54 | 1.59 | 1.62 |
| FIGNL1 | NM_022116 | −1.04 | 1.54 | 1.23 | 1.28 |
| CENPF | NM_016343 | 1.00 | 1.54 | 1.62 | 1.65 |
| DKFZp586I1420 | NM_152747 | 1.05 | 1.54 | 1.38 | 1.37 |

TABLE 9-continued

Expression alterations for miR-34 down-regulated genes in HCT116 Dicer Ex5 cells.

| Gene Names | Genbank Accession #[b] | Luc siRNA | mir-34a | mir-34b | mir-34c |
|---|---|---|---|---|---|
| E2F8 | NM_024680 | 1.04 | 1.54 | 1.55 | 1.90 |
| SLC7A1 | AL050021 | 1.16 | 1.54 | 1.70 | 1.51 |
| HCN3 | AB040968 | 1.09 | 1.54 | 1.32 | 2.07 |
| KIF20A | NM_005733 | 1.03 | 1.54 | 1.41 | 1.50 |
| DGKZ | NM_003646 | 1.11 | 1.54 | 1.52 | 1.67 |
| DCLRE1B | NM_022836 | −1.01 | 1.54 | 1.52 | 1.84 |
| DHCR24 | NM_014762 | 1.16 | 1.53 | 1.42 | 1.52 |
| ETEA | NM_014613 | 1.23 | 1.53 | 1.28 | 1.28 |
| PHF6 | NM_032458 | −1.03 | 1.53 | 2.25 | 2.21 |
| CDC45L | NM_003504 | 1.04 | 1.53 | 1.80 | 2.21 |
| C8orf30A | NM_016458 | 1.03 | 1.53 | 1.74 | 1.75 |
| HMGB3 | BC007608 | 1.05 | 1.53 | 1.92 | 2.03 |
| RARG | NM_000966 | 1.02 | 1.53 | 1.55 | 1.47 |
| NUSAP1 | NM_016359 | 1.03 | 1.53 | 1.45 | 1.50 |
| ASF1B | NM_018154 | −1.04 | 1.53 | 1.60 | 1.76 |
| MMS19L | NM_022362 | 1.09 | 1.53 | 1.47 | 1.55 |
| ACSL4 | NM_004458 | −1.09 | 1.53 | 1.95 | 1.91 |
| TRAF7 | NM_032271 | 1.26 | 1.53 | 1.33 | 1.36 |
| C15orf42 | NM_152259 | 1.08 | 1.53 | 1.43 | 1.62 |
| CDCA8 | NM_018101 | 1.04 | 1.52 | 1.62 | 1.72 |
| UHRF2 | NM_152306 | 1.07 | 1.52 | 1.26 | 1.43 |
| FOXM1 | NM_021953 | −1.13 | 1.52 | 1.38 | 1.52 |
| C22orf18 | NM_024053 | 1.10 | 1.52 | 1.53 | 1.57 |
| EVI5L | NM_145245 | −1.02 | 1.52 | 1.70 | 1.69 |
| AADACL1 | NM_020792 | 1.33 | 1.52 | 1.73 | 1.82 |
| ATP1B3P1 | NG_000849 | −1.13 | 1.51 | 1.62 | 1.52 |
| TRIOBP | NM_138632 | 1.24 | 1.51 | 1.46 | 1.52 |
| FUT8 | NM_178155 | 1.00 | 1.51 | 1.48 | 1.53 |
| IQGAP3 | NM_178229 | 1.08 | 1.51 | 1.23 | 1.43 |
| METTL1 | NM_005371 | 1.11 | 1.51 | 1.55 | 1.57 |
| OATL1 | L08240 | 1.06 | 1.51 | 1.35 | 1.30 |
| WSB2 | NM_018639 | 1.33 | 1.50 | 1.36 | 1.32 |
| ETV5 | NM_004454 | −1.07 | 1.50 | 1.67 | 1.83 |
| C21orf63 | NM_058187 | −1.19 | 1.50 | 1.25 | 1.28 |
| ENST00000273097 | ENST00000273097 | −1.01 | 1.50 | 1.53 | 1.45 |
| TBPIP | NM_013290 | −1.15 | 1.50 | 1.53 | 1.80 |
| VDR | NM_000376 | 1.00 | 1.50 | 1.50 | 1.51 |
| FKBP1B | NM_054033 | 1.24 | 1.50 | 1.68 | 1.64 |
| CSRP1 | NM_004078 | 1.14 | 1.50 | 1.65 | 1.85 |
| RRAS | NM_006270 | −1.02 | 1.50 | 1.38 | 1.42 |
| BTRC | NM_032715 | −1.04 | 1.50 | 1.28 | 1.37 |
| IRAK1 | NM_001569 | 1.07 | 1.50 | 1.53 | 1.60 |
| MTMR9 | NM_015458 | −1.04 | 1.49 | 1.73 | 1.79 |
| FBXO5 | NM_012177 | −1.12 | 1.49 | 1.46 | 1.65 |
| MGAT2 | NM_002408 | 1.11 | 1.49 | 1.37 | 1.42 |
| CHMP7 | NM_152272 | −1.00 | 1.49 | 1.43 | 1.41 |
| R3HDM1 | NM_015361 | 1.01 | 1.49 | 1.44 | 1.45 |
| FLJ32363 | BC036867 | −1.14 | 1.49 | 1.54 | 1.70 |
| Ells1 | NM_152793 | 1.17 | 1.49 | 1.93 | 2.05 |
| MGC13024 | NM_152288 | −1.10 | 1.49 | 1.23 | 1.19 |
| FOXJ2 | NM_018416 | 1.11 | 1.49 | 1.29 | 1.25 |
| PBEF1 | NM_005746 | 1.02 | 1.48 | 1.51 | 1.37 |
| H2AFX | NM_002105 | −1.03 | 1.48 | 1.53 | 1.54 |
| TESK2 | NM_007170 | 1.01 | 1.48 | 1.51 | 1.89 |
| OXSR1 | NM_005109 | −1.06 | 1.48 | 1.58 | 1.50 |
| RAD51C | NM_002876 | 1.02 | 1.48 | 1.34 | 1.33 |
| RIC8B | NM_018157 | −1.13 | 1.48 | 1.40 | 1.48 |
| KLHDC3 | NM_057161 | −1.11 | 1.48 | 1.89 | 2.25 |
| RBM12 | NM_152838 | 1.12 | 1.48 | 1.33 | 1.24 |
| DGAT1 | NM_012079 | 1.17 | 1.48 | 1.39 | 1.62 |
| STX1A | NM_004603 | 1.09 | 1.48 | 1.18 | 1.55 |
| GSK3B | AW139538 | 1.14 | 1.48 | 1.65 | 1.59 |
| MKL1 | NM_020831 | 1.02 | 1.47 | 1.41 | 1.57 |
| LASS2 | NM_013384 | 1.11 | 1.47 | 1.57 | 1.56 |
| MLF1IP | NM_024629 | 1.03 | 1.47 | 1.50 | 1.65 |
| SCNN1A | NM_001038 | −1.05 | 1.47 | 1.34 | 1.27 |
| PRC1 | NM_003981 | 1.04 | 1.47 | 1.53 | 1.64 |
| USP3 | AK094444 | 1.23 | 1.47 | 1.94 | 1.86 |
| FLJ39660 | NM_173466 | −1.08 | 1.47 | 1.61 | 2.20 |
| PPARG | NM_005037 | −1.06 | 1.47 | 1.82 | 1.86 |
| EIF2AK1 | NM_014413 | 1.38 | 1.47 | 2.22 | 2.09 |
| TMEM22 | NM_025246 | −1.07 | 1.47 | 1.53 | 1.54 |
| HSPC142 | NM_014173 | −1.03 | 1.47 | 1.31 | 1.30 |
| C10orf26 | AK000161 | −1.28 | 1.47 | 1.53 | 1.41 |
| C6orf106 | NM_022758 | 1.03 | 1.47 | 1.54 | 1.70 |
| SMPD1 | NM_000543 | −1.17 | 1.47 | 1.34 | 1.33 |
| RRM1 | NM_001033 | 1.10 | 1.46 | 1.31 | 1.38 |
| MSH6 | NM_000179 | 1.01 | 1.46 | 1.49 | 1.63 |
| PPIG | R38692 | 1.05 | 1.46 | 1.46 | 1.43 |
| KIF22 | NM_007317 | 1.02 | 1.46 | 1.38 | 1.47 |
| USP15 | NM_006313 | 1.08 | 1.46 | 1.58 | 1.56 |
| LOC400927 | AW206718 | 1.10 | 1.46 | 1.37 | 1.36 |
| PTTG1 | NM_004219 | −1.06 | 1.46 | 1.32 | 1.40 |
| PPM1A | BM676083 | −1.04 | 1.46 | 1.70 | 1.48 |
| ST3GAL5 | NM_003896 | 1.49 | 1.46 | 1.68 | 1.66 |
| CENPJ | NM_018451 | 1.05 | 1.46 | 1.48 | 1.82 |
| S100A2 | NM_005978 | −1.02 | 1.46 | 1.49 | 1.39 |
| PPRC1 | NM_015062 | 1.11 | 1.46 | 1.27 | 1.53 |
| LOC441347 | AL050136 | −1.11 | 1.46 | 1.80 | 1.55 |
| FLOT2 | NM_004475 | −1.02 | 1.46 | 1.74 | 1.69 |
| CDC7 | NM_003503 | 1.02 | 1.45 | 1.48 | 1.72 |
| KIAA0157 | NM_032182 | 1.01 | 1.45 | 1.88 | 1.96 |
|  | AK024294 | 1.14 | 1.45 | 1.52 | 1.35 |
| FUT8 | NM_178154 | 1.03 | 1.45 | 1.52 | 1.49 |
| SENP1 | BC045639 | −1.05 | 1.45 | 1.62 | 1.71 |
| TNFRSF1A | NM_001065 | 1.06 | 1.45 | 1.31 | 1.36 |
| ARSB | AK026942 | −1.04 | 1.45 | 1.58 | 1.61 |
| TTK | NM_003318 | −1.08 | 1.45 | 1.35 | 1.41 |
| KIAA0984 | AB023201 | 1.01 | 1.44 | 1.93 | 1.98 |
| RFC4 | NM_181573 | 1.00 | 1.44 | 1.59 | 1.78 |
| CLSPN | NM_022111 | −1.10 | 1.44 | 1.48 | 1.52 |
| AOC3 | NM_003734 | −1.05 | 1.44 | 1.22 | 1.50 |
| PSRC1 | NM_032636 | −1.10 | 1.44 | 1.46 | 1.65 |
| CREB3L2 | AL080209 | 1.02 | 1.44 | 1.94 | 1.71 |
| TPT1 | AI803535 | 1.04 | 1.44 | 1.41 | 1.39 |
| MAP3K7IP2 | NM_145342 | −1.13 | 1.44 | 1.56 | 1.52 |
| C18orf24 | NM_145060 | −1.03 | 1.44 | 2.10 | 2.44 |
| STK39 | NM_013233 | 1.10 | 1.44 | 1.17 | 1.04 |
| KIAA0476 | NM_014856 | 1.02 | 1.43 | 1.31 | 1.60 |
| GRK6 | NM_002082 | 1.06 | 1.43 | 1.58 | 1.41 |
| FARP1 | AK025683 | 1.01 | 1.43 | 1.42 | 1.25 |
| FLJ22794 | NM_022074 | 1.07 | 1.43 | 1.49 | 1.80 |
| MGC18216 | NM_152452 | 1.76 | 1.43 | 1.27 | 1.08 |
| WHSC1 | NM_133334 | 1.05 | 1.43 | 1.72 | 1.92 |
| TROAP | NM_005480 | −1.01 | 1.43 | 1.40 | 1.69 |
| PRIM1 | NM_000946 | 1.16 | 1.43 | 1.46 | 1.44 |
| TMEM55A | NM_018710 | −1.11 | 1.43 | 1.43 | 1.46 |
| LSS | NM_002340 | 1.17 | 1.42 | 1.31 | 1.36 |
| PURB | AK056651 | −1.16 | 1.42 | 1.64 | 2.26 |
| LOC151162 | AF055029 | 1.27 | 1.42 | 2.23 | 2.24 |
| BLM | NM_000057 | 1.16 | 1.42 | 1.70 | 1.97 |
| LONRF2 | AL157505 | −1.17 | 1.42 | 1.43 | 1.36 |
|  | AI927895 | 1.06 | 1.42 | 1.80 | 1.87 |
| KLC2 | NM_022822 | 1.00 | 1.42 | 1.36 | 1.45 |
| STCH | NM_006948 | −1.07 | 1.42 | 1.54 | 1.51 |
| PTTG2 | NM_006607 | −1.09 | 1.42 | 1.33 | 1.38 |
| GDPD5 | NM_030792 | −1.11 | 1.42 | 1.35 | 1.47 |
| CRTC2 | NM_181715 | 1.08 | 1.42 | 1.33 | 1.47 |
| DCTN5 | NM_032486 | 1.24 | 1.42 | 1.57 | 1.73 |
| POU2F1 | NM_002697 | 1.04 | 1.42 | 1.45 | 1.33 |
| KIF4A | NM_012310 | −1.02 | 1.42 | 1.30 | 1.40 |
| ESAM | NM_138961 | −1.12 | 1.42 | 1.28 | 1.43 |
| JPH1 | NM_020647 | −1.08 | 1.42 | 1.49 | 1.40 |
| OVOS2 | NM_173498 | −1.08 | 1.41 | 1.28 | 1.37 |
| ATF4 | NM_001675 | −1.00 | 1.41 | 1.38 | 1.32 |
| CKLF | NM_016951 | 1.02 | 1.41 | 1.37 | 1.48 |
| NT5E | AA046478 | 1.09 | 1.41 | 1.46 | 1.65 |
| SLC12A2 | AK025062 | 1.23 | 1.41 | 1.59 | 1.76 |
| hCAP-D3 | D29954 | −1.12 | 1.41 | 1.39 | 1.38 |
| LMNB1 | NM_005573 | 1.05 | 1.41 | 1.57 | 1.33 |

TABLE 9-continued

Expression alterations for miR-34 down-regulated genes in HCT116 Dicer Ex5 cells.

| Gene Names | Genbank Accession #[b] | Luc siRNA | mir-34a | mir-34b | mir-34c |
|---|---|---|---|---|---|
| ATG5 | NM_004849 | 1.30 | 1.41 | 1.98 | 1.95 |
| SEMA4F | NM_004263 | 1.03 | 1.41 | 1.28 | 1.29 |
| ZDHHC8 | NM_013373 | 1.10 | 1.40 | 1.14 | 1.52 |
| NXF4 | ENST00000289078 | 1.05 | 1.40 | 1.43 | 1.59 |
| HCAP-G | NM_022346 | 1.06 | 1.40 | 1.96 | 2.18 |
| PNPLA2 | NM_020376 | 1.14 | 1.40 | 1.39 | 1.46 |
| FAM76A | NM_152660 | -1.03 | 1.40 | 1.39 | 1.40 |
| RDH5 | NM_002905 | 1.04 | 1.40 | 1.42 | 1.55 |
| FSBP | NM_006550 | -1.06 | 1.40 | 1.37 | 1.55 |
| XPO4 | NM_022459 | 1.05 | 1.40 | 1.09 | 1.16 |
| MTMR10 | AL833089 | -1.02 | 1.40 | 1.67 | 1.75 |
| C21orf59 | AI564020 | 1.08 | 1.40 | 1.50 | 1.58 |
| C15orf20 | AF108138 | -1.09 | 1.40 | 1.59 | 2.25 |
| TBPIP | NM_016556 | -1.23 | 1.40 | 1.48 | 1.73 |
| L3MBTL3 | AB058701 | 1.01 | 1.39 | 1.41 | 1.30 |
| TUBA3 | NM_006009 | -1.07 | 1.39 | 1.46 | 1.28 |
| XRCC3 | NM_005432 | 1.13 | 1.39 | 1.38 | 1.63 |
| TFCP2L1 | NM_014553 | 1.26 | 1.39 | 1.61 | 2.15 |
| MCM10 | NM_018518 | 1.21 | 1.39 | 1.63 | 1.96 |
| FLJ38608 | NM_153215 | -1.03 | 1.39 | 1.49 | 1.42 |
| FLJ13710 | AI608673 | 1.07 | 1.39 | 1.26 | 1.15 |
| GGA2 | NM_015044 | 1.23 | 1.39 | 1.27 | 1.41 |
| FAM62B | AB033054 | 1.03 | 1.39 | 1.49 | 1.51 |
| FUT1 | NM_000148 | 1.01 | 1.39 | 1.24 | 1.31 |
| DHX33 | AA534526 | 1.01 | 1.38 | 1.47 | 1.52 |
| TRIM6 | NM_058166 | -1.52 | 1.38 | 1.74 | 1.99 |
| PPP2R3B | NM_013239 | -1.07 | 1.38 | 1.22 | 1.82 |
| TNPO1 | AL049378 | 1.33 | 1.38 | 1.52 | 1.61 |
| C6orf153 | NM_033112 | 1.03 | 1.38 | 1.33 | 1.42 |
| C2orf7 | NM_032319 | -1.05 | 1.38 | 1.34 | 1.61 |
| HNRPR | AK001846 | 1.11 | 1.38 | 1.73 | 1.76 |
| PRKAA1 | AI375852 | -1.18 | 1.38 | 1.37 | 1.57 |
| SLC19A1 | NM_003056 | 1.12 | 1.38 | 1.35 | 1.45 |
| C17orf41 | NM_024857 | -1.16 | 1.38 | 1.45 | 1.65 |
| EZH2 | NM_152998 | 1.12 | 1.38 | 1.58 | 1.83 |
| C10orf119 | NM_024834 | 1.27 | 1.38 | 1.78 | 1.86 |
| AK021744 | AK021744 | 1.18 | 1.37 | 1.17 | -1.15 |
| DHX37 | NM_032656 | 1.17 | 1.37 | 1.30 | 1.38 |
| MECP2 | NM_004992 | 1.29 | 1.37 | 1.74 | 1.70 |
| LGALS1 | NM_002305 | -1.01 | 1.37 | 0.00 | 0.00 |
| CCNB2 | NM_004701 | -1.04 | 1.37 | 1.54 | 1.60 |
| LOC388134 | AL355708 | -1.01 | 1.37 | 1.40 | 1.09 |
| LYPLAL1 | NM_138794 | -1.12 | 1.37 | 1.40 | 1.15 |
| SRGAP2 | AB007925 | -1.10 | 1.37 | 1.50 | 1.44 |
| ARHGEF5 | NM_005435 | 1.11 | 1.37 | 1.27 | 1.36 |
| SHMT1 | NM_004169 | -1.04 | 1.36 | 1.42 | 1.45 |
| DDR1 | NM_001954 | 1.10 | 1.36 | 1.38 | 1.48 |
| TACC3 | NM_006342 | -1.00 | 1.36 | 1.34 | 1.50 |
| FLJ27365 | AI973033 | 1.01 | 1.36 | 1.30 | 1.57 |
| ECOP | NM_030796 | 1.08 | 1.36 | 1.35 | 1.63 |
| PTTG1IP | NM_004339 | 1.12 | 1.36 | 1.42 | 1.45 |
| RRM2 | NM_001034 | -1.11 | 1.36 | 1.89 | 1.91 |
| DHX33 | NM_020162 | -1.06 | 1.36 | 1.38 | 1.47 |
| PSD3 | NM_018422 | 1.04 | 1.35 | 1.17 | -1.08 |
| COPS7B | NM_022730 | 1.28 | 1.35 | 1.45 | 1.55 |
| CDCA1 | NM_031423 | -1.20 | 1.35 | 1.51 | 1.70 |

[a]Each value represents fold reduction for each experimental condition as indicated, as compared to the mock transfection in Hct116 Dicer[ex5] cells. Negative value in the luc siRNA transfected cells represents fold increase.
[b]Refseq accession numbers are provided for all annotated genes, which are each hereby incorporated by reference. mRNA accession numbers are provided for those unannotated genes included on the microarray.

Consistent with the cell cycle phenotype described in Example 6, the genes listed in Table 9 were found to be enriched for genes associated with cell cycle (see Table 10). In addition, the down-regulated or up-regulated gene signatures of the microarray data were examined to determine whether genes associated with TP53 pathway were enriched in either of these miR-34 response gene signatures. To do this, the data were examined to determine the degree of overlap between the miR-34 signature genes and TP53 pathway gene identified as such in the Gene Ontology Database (Camon et al., 2004, *Nucleic Acids Res.* 32:D262-6; Camon et al., 2003, *Genome Res.* 13:662-72), the TP53 DNA damage response gene set, genes identified as being down-regulated in the RNAi experiments reported in Example 6, and a set of direct TP53 targets identified by a genome-scale chromatin immunoprecipitation (ChIP) analysis of TP53 transcription factor binding sites (Wei et al., 2006, *Cell* 124:207-19).

Table 10 provides the overlap of genes up-regulated or down-regulated by miR-34 transfection with sets of genes implicated in DNA damage and the cell cycle. Biological function was categorized by enrichment of transcripts from Gene Ontology Biological Process functional categories (http://www.geneontology.org/), as described in *The Gene Ontology Consortium, Gene Ontology: tool for the unification of biology*. Nature Genetics (2000) 25:25-29. The numbers of genes in the identified gene sets or the overlaps of the sets are shown in brackets and italicized font. The probability of each result, expressed as a P-value, was calculated by hypergeometric distribution (Lee et al., *BMC Bioinformatics* 2005 6:189) and is shown in Table 10. All genes represented on the microarray were used as the background set.

TABLE 10

Overlap of genes up-regulated or down-regulated by miR-34 transfection with sets of genes implicated in DNA damage and the cell cycle.

| Gene Set Categories Being Compared | Genes down-regulated following doxorubicin treatment [*2104 genes*] | Genes up-regulated following doxorubicin treatment [*2280 genes*] | GO Biological Process category for "Cell cycle" [*1202 genes*] |
|---|---|---|---|
| Genes up-regulated by miR-34 [*1022 genes*] | P-value: 0.56 [*Overlap: 101 genes*] | P-value: 7.0e−65 [*Overlap: 303 genes*] | P-value: 7.4e−5 [*Overlap: 88 genes*] |
| Genes down-regulated by miR-34 [*582 genes*] | P-value: 1.8e−73 [*Overlap: 219 genes*] | P-value: 0.94 [*Overlap: 52 genes*] | P-value: 1.1e−19 [*Overlap: 93 genes*] |

A significant overlap between miR-34-regulated genes and those whose expression is altered upon DNA damage (Table 10) was observed. In this case, significant overlap was seen both for genes that increased in response to miR-34 transfection (p<7e-65) and those that are repressed upon miR-34 activation (p<1.8e-73). However, while a strong enrichment of genes that have sequences complementary to miR-34 seed regions was seen in the down-regulated overlapping set, it was not seen in the up-regulated gene set, suggesting that the genes up-regulated in expression might be caused by secondary effects of miR-34.

As shown in Table 10, a significant overlap was found between genes regulated by miR34a and common TP53 mediated events, suggesting that miR-34 transfection may induce at least a portion of the TP53 pathway. When these results are combined with the data showing that TP53 function correlates with miR-34 transcription (Example 1), the combined observations support the conclusion that miR-34a, miR-34b, and miR-34c are functional members of the TP53 pathway.

EXAMPLE 8

This Example demonstrates that measured levels of miR34 are correlated with TP53 status in human tumor samples.

Rationale:

While analysis of in vitro cell culture systems and mice in the preceding examples shows that miR-34 levels are correlated with TP53 activity, it was unknown whether this same relationship would be found using in vivo cell samples taken from human subjects. To test this possibility, the levels of miR-34 family members were measured in a collection of samples taken from human tumor and adjacent non-involved tissues that were obtained from between 50 to 70 patients for five different solid tumors (breast, colon, kidney, gastric, and lung). These human tumor samples were purchased from Collaborative Genomics, Inc. (Cambridge, Mass.), which was subsequently purchased by SeraCare Life Sciences, Inc. (West Bridgewater, Mass.).

Methods:

The levels of miR-34 family members were measured in a collection of samples taken from human tumor and adjacent non-involved tissues that were obtained from between 50 to 70 patients for five different solid tumors (breast, colon, kidney, gastric, and lung). These human tumor samples were purchased from Collaborative Genomics, Inc. (Cambridge, Mass.), which was subsequently purchased by SeraCare Life Sciences, Inc. (West Bridgewater, Mass.). Each sample was pulverized and split into two tubes, one of which was used for RNA extraction by use of an RNEASY® kit (Qiagen, Inc., Valencia, Calif.). Purified total RNA samples were profiled on 25K Human Agilent microarrays (Agilent Technologies, Inc., Santa Clara, Calif.). Some of the remaining tumor RNA crude extracts, before purification on RNEASY columns, were used for miRNA analysis as described in Raymond et al. (RNA 2005 11:1737-44). It was then determined whether the genes associated with TP53 function, as identified in Example 1, were correlated with the measured levels of miR-34 in these tumor samples.

Levels of 189 miRNAs and ~20,000 transcripts were compared in 29 tumor and 28 normal samples and correlation coefficients were calculated to quantitate the degree of coordinate variation of the miRNAs and transcripts.

Figure 4:
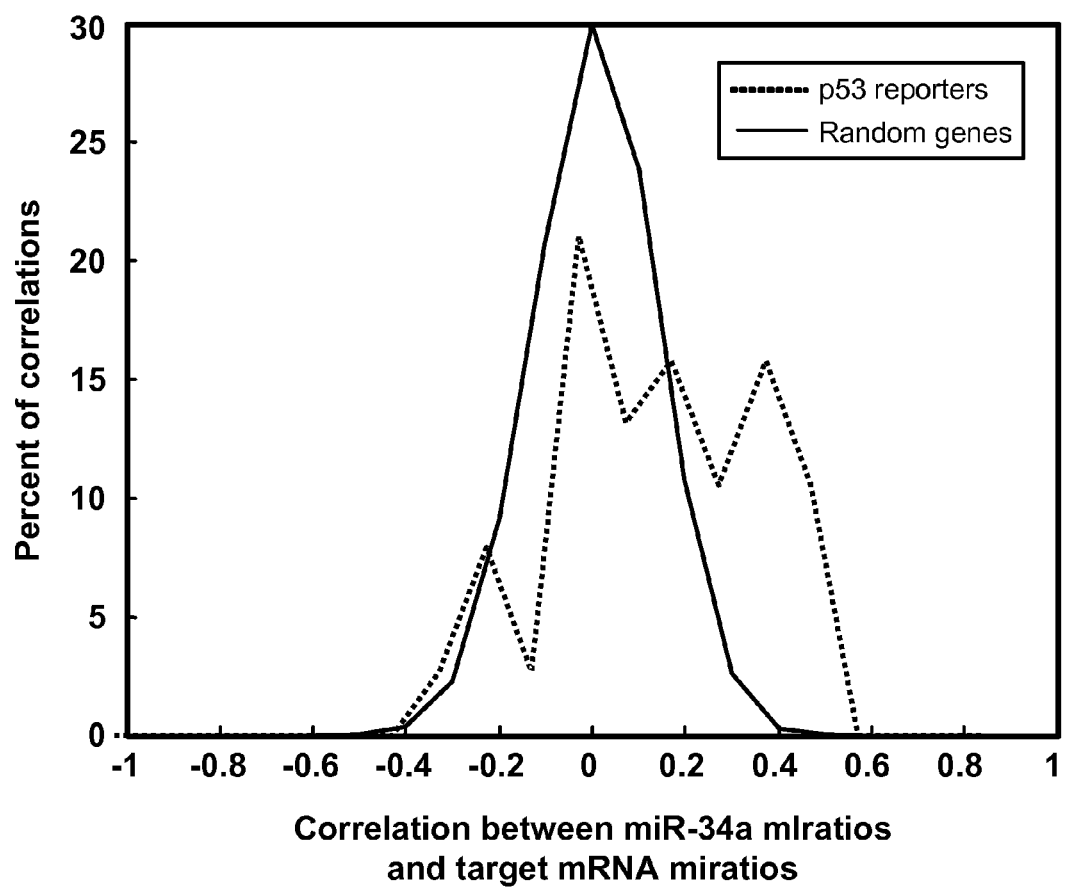
FIG. 4 shows the distribution of correlations between expression of genes known to be associated with TP53 activity (TP53 reporter genes) and miR-34a levels, or between shuffled random genes and miR-34a levels (Monte Carlo).

Results:

FIG. 4 shows the distribution of correlations between TP53 reporters and miR-34a levels, or between shuffled TP53 reporter data and miRNA levels upon performance of Monte Carlo simulations. As shown in FIG. 4, the TP53 reporter genes (dotted line) were significantly enriched for positive correlations with miR-34a levels (p<7e-7). FIG. 4 shows that the distribution of these correlations shows a highly significant enrichment of positive correlations.

These data suggest that transcripts regulated by miR-34 in vitro are also regulated by miR-34 in vivo. These findings show that miR-34 levels are biomarkers of TP53 status in human tumor samples. One advantage of using miRNAs as an indicator of TP-53 functional status is that microRNA integrity may be more readily maintained in poor-quality RNA preparations from human tumor biopsies or archival samples, thus, making their measurements more accurate than longer, and more degradation susceptible, mRNAs extracted from these types of samples.

EXAMPLE 9

This Example demonstrates that introduction of synthetic miR449, a member of the miR-34 family, into cell line HCT116 elicits a phenotype similar to that induced by activation of the TP53 G1 checkpoint.

Rationale:

Delay of the G1/S transition of the cell cycle is known to be a consequence of TP 53 activation. In this example, miR-449 siRNA duplexes were designed with passenger strands that are complementary to the natural mature miRNA, except for a single base mismatch four bases from the 3' end of the sequence, referred to as "asymmetric passenger strands." Exemplary asymmetric passenger strands are provided in Table 11 for miR-449 (SEQ ID NO:32), with the mismatch underlined. As shown in Table 11, the synthetically designed asymmetric passenger strand for miR-449 (SEQ ID NO:32) differs from the natural passenger strand for miR-449 (SEQ ID NO:38). The data presented in this example shows that introduction of duplex a miR-449 mimetic comprising a natural miR449 guide strand (SEQ ID NO:29) annealed to a asymmetric miR-449 passenger strand (SEQ ID NO:32) into cells leads to cell cycle arrest at the G1 checkpoint in a manner that is analogous to activation of TP53.

Methods:

The cell line HCT116#2, a p53 positive cell line, was transfected with miR-16, miR-34a, miR-34a-mm2,3, miR-449, and miR-449-mm2,3 or luciferase control using the DNA oligonucleotides described in Table 11. Prior to transfection, the cells were seeded at 12.5×104 and transfected using 10 nM final concentration of the synthetic oligonucleotides using Lipofectamine RNAiMax. 30 hours post transfection, Nocodazole was added at a final concentration of 100 ng/mL. The cells were harvested 18 hours after adding nocodazole.

TABLE 11

Synthetic miR-449 Oligonucleotide Sequences

| siRNA, miRNA or mismatch miRNA | Guide strand/mature (5' to 3') | SEQ ID NO: | Passenger strand (5' to 3') | SEQ ID NO: |
|---|---|---|---|---|
| miR34a | UGGCAGUGUCUUAGCUGGUUGU (natural) | 1 | AACCAGCUAAGACACUGCGAAU (synthetic: reverse complement of natural guide strand with one base mismatch) | 12 |
| miR34a-mm2,3 | UCCCAGUGUCUUAGCUGGUUGU (mutation in seed region) | 13 | AACCAGCUAAGACACUGGCAAU (synthetic: reverse complement of seed region mutation with one base mismatch) | 14 |
| miR449 | UGGCAGUGUAUUGUUAGCUGGU (natural) | 29 | AUCGGCUAACAUGCAACUGCUG (natural) | 38 |
| miR449 | UGGCAGUGUAUUGUUAGCUGGU (natural) | 29 | CAGCUAACAAUACACUGUUAAU (synthetic: reverse complement of natural guide strand with mismatch) | 32 |
| miR449_mm2,3 (seed mismatch) | UCCCAGUGUAUUGUUAGCUGGU (mutation in seed region) | 33 | CAGCUAACAAUACACUGGCAAU (synthetic: reverse complement of seed region mutation) | 34 |
| luciferase | CGUACGCGGAAUACUUCGA | 27 | UCGAAGUAUUCCGUACG | 28 |

As shown in Table 12, the transfection of miR-449 (WT mature) and miR-34a (WT mature) results in a G1 arrest of HCT116 cells, similar to the results observed when miR-34a (WT mature), miR-34b (WT mature), and miR-34c (WT mature) were transfected into A549 cells, as shown in Example 6. As further shown in Table 12, transfection of miR-16 (WT mature) also results in a G1 arrest of HCT116 cells, consistent with the results described in Linsley P. S. et al., *Mol Cell Biol* 27: 2240-2252 (2007).

TABLE 12

Cell Cycle Arrest in HCT116 Cells (wild type p53) Transfected with Synthetic siRNA Constructs

| microRNA species introduced into HCT116 cells (wt p53) | % Cells in G1 |
|---|---|
| miR34a (WT mature) | 52.9% |
| miR34a-mm2,3 (seed mismatch) | 8.8% |
| miR449 (WT mature) | 40.9% |
| miR449 (seed mismatch) | 9.2% |
| luciferase | 9.5% |
| miR16 (WT mature: positive control) | 60.5% |
| mock transfection | 8.2% |

Discussion: miR-34s belong to an evolutionary conserved miRNA family, with single, recognizable orthologues in several invertebrate species. See He et al., *Nature* 447:1130-1134 (2007). As shown in FIG. 1, the seed region of miR-449 (SEQ ID NO:31) comprises a nucleotide sequence of at least six contiguous nucleotides that is identical to six contiguous nucleotides within the seed region of miR-34a (SEQ ID NO:3), miR-34b (SEQ ID NO:6), and miR-34c (SEQ ID NO:9).

In summary, it appears that the effect of overexpression of miR-449 in p53 wild type cells elicits a phenotype similar to that induced by activation of the TP53 G1 checkpoint, consistent with the results demonstrated in Example 6 for overexpression of miR-34a, miR-34b, and miR-34c in A549 cells.

EXAMPLE 10

This Example demonstrates that introduction of miR-34a causes cell death in HCT116 Dicer Ex 5 and other cell lines.

Methods:

HCT116 Dicer Ex5 cells were transfected with natural duplexes of annealed natural miR-34a guide strand (SEQ ID NO:1) and natural miR34a passenger strand (SEQ ID NO:35) or synthetic duplexes of annealed natural miR-34a guide strand (SEQ ID NO:1) and synthetic asymmetric passenger strand (SEQ ID NO:12) that is complementary to the natural mature miR-34a, except for a single base mismatch four bases from the 3' end of the sequence (shown in Table 7). Cells were also mock transfected, or transfected with an siRNA duplex targeting luciferase (SEQ ID NO:27/SEQ ID NO:28). Forty eight hours post transfection, the cells were treated with Nocodazole (100 ng/ml) for 16 hours. The percentage of cells in sub-G1 (dead cells) was measured using propidium iodide staining and flow cytometry.

Results:

TABLE 13

Cell Cycle Arrest in HCT116 Cells (wild type p53) Transfected with Natural miR-34a or Synthetic siRNA Constructs

| microRNA species introduced into HCT116 dicer−/− cells (wild type p53) | % Cells in sub-G1 |
|---|---|
| miR34a natural (SEQ ID NO: 1/SEQ ID NO: 35) | 27.2% |
| miR-34a mimic (SEQ ID NO: 1/SEQ ID NO: 12) | 43% |
| luciferase control (SEQ ID NO: 27/SEQ ID NO: 28) | 5.7% |
| mock transfection | 2.2% |

As shown in Table 13, the miR-34a mimic duplex was more effective at inducing cell death than the natural miR-34a duplex, as determined by the percentage of cells in sub-G1 as measured by flow cytometry of transfected cells.

While not wishing to be bound by theory, it is believed that the presence of the mismatch in the asymmetric passenger strand destabilizes the duplex in that region and thereby facilitates entry into RISC of the strand mimicking mature miR-34. The duplex miR-34 mimetic sequence with the asymmetric passenger strand and natural guide strand is processed resulting in formation of the mature wild type miR-34 guide strand.

Summary:

This Example shows that an siRNA duplex mimetic sequence of miR-34a containing a natural guide strand annealed to a synthetic passenger strand that is complementary to the natural mature miR-34a, except for a single base mismatch four bases from the 3' end of the sequence, (referred to as "asymmetric passenger strand") was unexpectedly found to be more effective at inducing cell death when transfected into cells than the natural miR34 duplex.

EXAMPLE 11

This Example describes the validation of the hepatocyte growth factor receptor c-MET as a target of miR-34, and the use of exogenous miR-34 to inhibit proliferation of the c-MET dependent cell line EBC-1.

Methods:

Activation of c-MET has been implicated in growth, invasion and proliferation in many cancers including non-small cell lung carcinoma (NSCLC), gastric cancer, and a number of lung tumor lines including EBC-1 depend on c-MET for growth and survival (Lutterbach et al., 2007, *Cancer Res* 1 67(5):2081-8).

As shown in TABLE 9, after transfection of miR-34a, b, or c into HCT116 Dicer Ex5 cells, a set of genes including the hepatocyte growth factor receptor (c-MET) was downregulated. This observation was validated by western blotting (data not shown). Consistent with this observation, the human c-MET transcript contains two miR-34 target sites in its '3 UTR.

To determine the effect of introducing miR-34 into lung cancer cells that are dependent on c-MET for survival, EBC-1 cells (non-small cell lung cancer) were transfected with a normal synthetic miR-34a RNA duplex (WT) comprising a guide strand [SEQ ID NO:1] and a passenger strand [SEQ ID NO:12] or a seed region double mutant synthetic miR-34a(2, 3) RNA duplex comprising a guide strand [SEQ ID NO:13] and a passenger strand [SEQ ID NO:14]. 48 hours after transfection, the cells were harvested for cell cycle analysis by flow cytometry and Western blot analysis.

Results: EBC-1 cells transfected with normal synthetic miR-34a showed a substantial increase in sub-G1 population as compared to cells transfected with seed region mutant synthetic miR-34a or luciferase control. Protein lysates were analyzed by Western blot with antibodies for c-MET and cleaved PARP1, an indicator of apoptosis. Cells transfected with normal synthetic miR-34a showed a decrease in c-MET protein and an increase in cleaved PARP1 in comparison to the cells transfected with seed region mutant synthetic miR-34a or luciferase control. These results are consistent with the ability of miR-34a to silence c-MET and induce apoptosis in EBC-1 cells which are dependent on c-MET for survival.

Together, these results demonstrate that a miR-34a therapeutic agent could be used to inhibit growth and proliferation, and/or promote apoptosis of c-MET dependent tumors. The use of miR-34a duplexes can be readily tested in mouse tumor models and xenograft or spontaneous tumors that are c-MET dependent.

While illustrative embodiments have been illustrated and described, it will be appreciated that various changes can be made therein without departing from the spirit and scope of the invention.

The invention claimed is:

1. A method of inhibiting cell division of a mammalian cell comprising introducing into said cell an effective amount of a small interfering nucleic acid (siNA), wherein said siNA comprises a guide strand contiguous nucleotide sequence of 18 to 25 nucleotides and a passenger strand, wherein said guide strand comprises a seed region consisting of nucleotide positions 1 to 12, wherein position 1 represents the 5' end of said guide strand and wherein said seed region comprises a nucleotide sequence of at least six contiguous nucleotides that is identical to six contiguous nucleotides within a sequence selected from the group consisting of SEQ ID NO:3, SEQ ID NO:6, SEQ ID NO:9, and SEQ ID NO:31.

2. The method of claim 1, wherein said guide strand contiguous nucleotide sequence consists of 22 nucleotides and said seed region consists of nucleotide positions 1 to 10.

3. The method of claim 2, wherein said seed region comprises a nucleotide sequence that is identical to nucleotide positions 2 to 8 of SEQ ID NO:3, SEQ ID NO:6, or SEQ ID NO:9.

4. The method of claim 1, wherein said siNA further comprises a non-nucleotide moiety.

5. The method of claim 1, wherein the guide strand and the passenger strand are stabilized against nucleolytic degradation.

6. The method of claim 1, wherein said siNA further comprises at least one chemically modified nucleotide or non-nucleotide at the 5' end and/or 3' end of the guide strand and the 3' end of the passenger strand.

7. The method of claim 1, wherein said siNA further comprises one 3'-overhang wherein said 3'-overhang consists of 1 to 4 nucleotides.

8. The method of claim 1, wherein said siNA further comprises one 3'-overhang wherein said 3'-overhang consists of 2 nucleotides.

9. The method of claim 8, wherein said siNA further comprises a second 3'-overhang wherein said second 3'-overhang comprises from 1 to 4 nucleotides.

10. The method of claim 1, wherein said siNA further comprises a phosphorothioate at the first internucleotide linkage at the 5' end of the passenger strand and guide strand.

11. The method of claim 1, wherein said siNA further comprises a phosphorothioate at the first internucleotide linkage at the 3' end of the passenger strand and the guide strand.

12. The method of claim 1, wherein said siNA further comprises a phosphorothioate at the first internucleotide linkage at the 5' end of the guide strand and the passenger strand, and a phosphorothioate at the first internucleotide linkage at the 3' end of the guide strand and the passenger sequences.

13. The method of claim 1, wherein said siNA further comprises a 2'-modified nucleotide.

14. The method of claim 13, wherein the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

* * * * *

UNITED STATES PATENT AND TRADEMARK OFFICE
CERTIFICATE OF CORRECTION

PATENT NO.         : 8,399,248 B2                                        Page 1 of 1
APPLICATION NO.    : 12/598563
DATED              : March 19, 2013
INVENTOR(S)        : M. A. Cleary et al.

It is certified that error appears in the above-identified patent and that said Letters Patent is hereby corrected as shown below:

| COLUMN | LINE | ERROR |
|---|---|---|
| Item (73)<br>Title Pg. 1, col. 1 | Assignee | After "Merck Sharp & Dohme Corp., Rahway, NJ (US)" insert --Cold Spring Harbor Laboratory, Cold Spring Harbor, NY (US)-- |

Signed and Sealed this
Eleventh Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,399,248 B2                                                          Page 1 of 1
APPLICATION NO.   : 12/598563
DATED             : March 19, 2013
INVENTOR(S)       : Cleary et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 542 days.

Signed and Sealed this
First Day of September, 2015

Michelle K. Lee
*Director of the United States Patent and Trademark Office*

SEQUENCE LISTING

```
<160> NUMBER OF SEQ ID NOS: 38

<210> SEQ ID NO 1
<211> LENGTH: 22
<212> TYPE: RNA
<213> ORGANISM: Homo sapiens

<400> SEQUENCE: 1
uggcaguguc uuagcugguu gu                                              22

<210> SEQ ID NO 2
<211> LENGTH: 110
<212> TYPE: RNA
<213> ORGANISM: Homo sapiens

<400> SEQUENCE: 2
ggccagcugu gaguguuucu uuggcagugu cuuagcuggu uguugugagc aauaguaagg    60
aagcaaucag caaguauacu gcccuagaag ugcugcacgu ugugggccc                110

<210> SEQ ID NO 3
<211> LENGTH: 12
<212> TYPE: RNA
<213> ORGANISM: Homo sapiens

<400> SEQUENCE: 3
```

-continued

```
uggcaguguc uu                                                         12

<210> SEQ ID NO 4
<211> LENGTH: 22
<212> TYPE: RNA
<213> ORGANISM: Homo sapiens

<400> SEQUENCE: 4
aggcaguguc auuagcugau ug                                              22

<210> SEQ ID NO 5
<211> LENGTH: 84
<212> TYPE: RNA
<213> ORGANISM: Homo sapiens

<400> SEQUENCE: 5
gugcucgguu uguaggcagu gucauuagcu gauuguacug uggugguuac aaucacuaac     60
uccacugcca ucaaaacaag gcac                                            84

<210> SEQ ID NO 6
<211> LENGTH: 12
<212> TYPE: RNA
<213> ORGANISM: Homo sapiens

<400> SEQUENCE: 6
aggcaguguc au                                                         12

<210> SEQ ID NO 7
<211> LENGTH: 22
<212> TYPE: RNA
<213> ORGANISM: Homo sapiens

<400> SEQUENCE: 7
aggcagugua guuagcugau ug                                              22

<210> SEQ ID NO 8
<211> LENGTH: 77
<212> TYPE: RNA
<213> ORGANISM: Homo sapiens

<400> SEQUENCE: 8
agucuaguua cuaggcagug uaguuagcug auugcuaaua guaccaauca cuaaccacac     60
ggccagguaa aaagauu                                                    77

<210> SEQ ID NO 9
<211> LENGTH: 12
<212> TYPE: RNA
<213> ORGANISM: Homo sapiens

<400> SEQUENCE: 9
aggcagugua gu                                                         12

<210> SEQ ID NO 10
<211> LENGTH: 19
<212> TYPE: RNA
<213> ORGANISM: Artificial Sequence
<220> FEATURE:
<223> OTHER INFORMATION: TP53 shRNA core sequence

<400> SEQUENCE: 10
gacuccagug guaaucuac                                                  19
```

```
<210> SEQ ID NO 11
<211> LENGTH: 52
<212> TYPE: RNA
<213> ORGANISM: Artificial Sequence
<220> FEATURE:
<223> OTHER INFORMATION: Full shRNA hairpin sequence targeting TP53
      cloned into lentiviral vector

<400> SEQUENCE: 11
gacuccagug guaaucuacu ucaagagagu agauuaccac uggagucuuu uu          52

<210> SEQ ID NO 12
<211> LENGTH: 22
<212> TYPE: RNA
<213> ORGANISM: Homo sapiens

<400> SEQUENCE: 12
aaccagcuaa gacacugcga au                                          22

<210> SEQ ID NO 13
<211> LENGTH: 22
<212> TYPE: RNA
<213> ORGANISM: Artificial Sequence
<220> FEATURE:
<223> OTHER INFORMATION: Synthetic miR-34a seed region double mutant
      guide strand
<220> FEATURE:
<221> NAME/KEY: mutation
<222> LOCATION: (2)..(3)

<400> SEQUENCE: 13
ucccaguguc uuagcugguu gu                                          22

<210> SEQ ID NO 14
<211> LENGTH: 22
<212> TYPE: RNA
<213> ORGANISM: Artificial Sequence
<220> FEATURE:
<223> OTHER INFORMATION: Synthetic miR-34a seed region double mutant,
      passenger strand
<220> FEATURE:
<221> NAME/KEY: mutation
<222> LOCATION: (18)..(19)

<400> SEQUENCE: 14
aaccagcuaa gacacuggca au                                          22

<210> SEQ ID NO 15
<211> LENGTH: 22
<212> TYPE: RNA
<213> ORGANISM: Artificial Sequence
<220> FEATURE:
<223> OTHER INFORMATION: Synthetic miR-34a non-seed region double
      mutant, guide strand
<220> FEATURE:
<221> NAME/KEY: mutation
<222> LOCATION: (18)..(19)

<400> SEQUENCE: 15
uggcaguguc uuagcugcau gu                                          22

<210> SEQ ID NO 16
<211> LENGTH: 22
<212> TYPE: RNA
<213> ORGANISM: Artificial Sequence
<220> FEATURE:
<223> OTHER INFORMATION: Synthetic miR-34a non-seed region double
      mutant, passenger strand
<220> FEATURE:
<221> NAME/KEY: mutation
```

```
<222> LOCATION: (2)..(3)

<400> SEQUENCE: 16
augcagcuaa gacacugcga au                                                    22

<210> SEQ ID NO 17
<211> LENGTH: 22
<212> TYPE: RNA
<213> ORGANISM: Homo sapiens

<400> SEQUENCE: 17
aucagcuaau gacacugcgu au                                                    22

<210> SEQ ID NO 18
<211> LENGTH: 22
<212> TYPE: RNA
<213> ORGANISM: Artificial Sequence
<220> FEATURE:
<223> OTHER INFORMATION: Synthetic miR-34b seed region double mutant,
      guide strand
<220> FEATURE:
<221> NAME/KEY: mutation
<222> LOCATION: (2)..(3)

<400> SEQUENCE: 18
acccaguguc auuagcugau ug                                                    22

<210> SEQ ID NO 19
<211> LENGTH: 22
<212> TYPE: RNA
<213> ORGANISM: Artificial Sequence
<220> FEATURE:
<223> OTHER INFORMATION: Synthetic miR-34b seed region double mutant,
      passenger strand
<220> FEATURE:
<221> NAME/KEY: mutation
<222> LOCATION: (18)..(19)

<400> SEQUENCE: 19
aucagcuaau gacacuggcu au                                                    22

<210> SEQ ID NO 20
<211> LENGTH: 22
<212> TYPE: RNA
<213> ORGANISM: Artificial Sequence
<220> FEATURE:
<223> OTHER INFORMATION: Synthetic miR-34b non-seed region double
      mutant, guide strand
<220> FEATURE:
<221> NAME/KEY: mutation
<222> LOCATION: (18)..(19)

<400> SEQUENCE: 20
aggcaguguc auuagcucuu ug                                                    22

<210> SEQ ID NO 21
<211> LENGTH: 22
<212> TYPE: RNA
<213> ORGANISM: Artificial Sequence
<220> FEATURE:
<223> OTHER INFORMATION: Synthetic miR-34b non-seed region double
      mutant, passenger strand
<220> FEATURE:
<221> NAME/KEY: mutation
<222> LOCATION: (2)..(3)

<400> SEQUENCE: 21
aagagcuaau gacacugcgu au                                                    22
```

```
<210> SEQ ID NO 22
<211> LENGTH: 22
<212> TYPE: RNA
<213> ORGANISM: Homo Sapiens

<400> SEQUENCE: 22
aucagcuaac uacacugcgu au                                              22

<210> SEQ ID NO 23
<211> LENGTH: 22
<212> TYPE: RNA
<213> ORGANISM: Artificial Sequence
<220> FEATURE:
<223> OTHER INFORMATION: Synthetic miR-34c seed region double mutant,
      guide strand
<220> FEATURE:
<221> NAME/KEY: mutation
<222> LOCATION: (2)..(3)

<400> SEQUENCE: 23
acccagugua guuagcugau ug                                              22

<210> SEQ ID NO 24
<211> LENGTH: 22
<212> TYPE: RNA
<213> ORGANISM: Artificial Sequence
<220> FEATURE:
<223> OTHER INFORMATION: Synthetic miR-34c seed region double mutant,
      passenger strand
<220> FEATURE:
<221> NAME/KEY: mutation
<222> LOCATION: (18)..(19)

<400> SEQUENCE: 24
aucagcuaac uacacuggcu au                                              22

<210> SEQ ID NO 25
<211> LENGTH: 22
<212> TYPE: RNA
<213> ORGANISM: Artificial Sequence
<220> FEATURE:
<223> OTHER INFORMATION: Synthetic miR-34c non-seed region double
      mutant, guide strand
<220> FEATURE:
<221> NAME/KEY: mutation
<222> LOCATION: (18)..(19)

<400> SEQUENCE: 25
aggcagugua guuagcucuu ug                                              22

<210> SEQ ID NO 26
<211> LENGTH: 22
<212> TYPE: RNA
<213> ORGANISM: Artificial Sequence
<220> FEATURE:
<223> OTHER INFORMATION: Synthetic miR-34c non-seed region double
      mutant, passenger strand
<220> FEATURE:
<221> NAME/KEY: mutation
<222> LOCATION: (2)..(3)

<400> SEQUENCE: 26
aagagcuaac uacacugcgu au                                              22

<210> SEQ ID NO 27
<211> LENGTH: 21
<212> TYPE: DNA
<213> ORGANISM: Artificial Sequence
<220> FEATURE:
```

```
<223> OTHER INFORMATION: Guide strand of luciferase siRNA
<220> FEATURE:
<221> NAME/KEY: misc_feature
<222> LOCATION: (20)..(21)
<223> OTHER INFORMATION: Sequence is RNA/DNA hybrid, wherein N=T

<400> SEQUENCE: 27
cguacgcgga auacuucgan n                                              21

<210> SEQ ID NO 28
<211> LENGTH: 19
<212> TYPE: DNA
<213> ORGANISM: Artificial Sequence
<220> FEATURE:
<223> OTHER INFORMATION: Passenger stand of luciferase siRNA
<220> FEATURE:
<221> NAME/KEY: misc_feature
<222> LOCATION: (18)..(19)
<223> OTHER INFORMATION: Sequence is RNA/DNA hybrid, wherein N=T

<400> SEQUENCE: 28
ucgaaguauu ccguacgnn                                                 19

<210> SEQ ID NO 29
<211> LENGTH: 22
<212> TYPE: RNA
<213> ORGANISM: Homo Sapiens

<400> SEQUENCE: 29
uggcagugua uuguuagcug gu                                             22

<210> SEQ ID NO 30
<211> LENGTH: 91
<212> TYPE: RNA
<213> ORGANISM: Homo Sapiens

<400> SEQUENCE: 30
cuguguguga ugagcuggca guguauuguu agcugguuga auaugugaau ggcaucggcu    60
aacaugcaac ugcugucuua uugcauauac a                                   91

<210> SEQ ID NO 31
<211> LENGTH: 12
<212> TYPE: RNA
<213> ORGANISM: Homo Sapiens

<400> SEQUENCE: 31
uggcagugua uu                                                        12

<210> SEQ ID NO 32
<211> LENGTH: 22
<212> TYPE: RNA
<213> ORGANISM: Homo Sapiens

<400> SEQUENCE: 32
cagcuaacaa uacacuguua au                                             22

<210> SEQ ID NO 33
<211> LENGTH: 22
<212> TYPE: RNA
<213> ORGANISM: Homo Sapiens

<400> SEQUENCE: 33
ucccagugua uuguuagcug gu                                             22

<210> SEQ ID NO 34
```

```
<211> LENGTH: 22
<212> TYPE: RNA
<213> ORGANISM: Homo Sapiens

<400> SEQUENCE: 34
cagcuaacaa uacacuggca au                                              22

<210> SEQ ID NO 35
<211> LENGTH: 22
<212> TYPE: RNA
<213> ORGANISM: Homo Sapiens

<400> SEQUENCE: 35
caaucagcaa guauacugcc cu                                              22

<210> SEQ ID NO 36
<211> LENGTH: 22
<212> TYPE: RNA
<213> ORGANISM: Homo Sapiens

<400> SEQUENCE: 36
caaucacuaa cuccacugcc au                                              22

<210> SEQ ID NO 37
<211> LENGTH: 22
<212> TYPE: RNA
<213> ORGANISM: Homo Sapiens

<400> SEQUENCE: 37
aaucacuaac cacacggcca gg                                              22

<210> SEQ ID NO 38
<211> LENGTH: 22
<212> TYPE: RNA
<213> ORGANISM: Homo Sapiens

<400> SEQUENCE: 38
aucggcuaac augcaacugc ug                                              22
```